United States Patent
Yang et al.

(10) Patent No.: US 12,196,751 B2
(45) Date of Patent: *Jan. 14, 2025

(54) METHOD, SYSTEM, REAGENT KIT, AND DEVICE FOR DETERMINING HD-HOOK-EFFECT SAMPLE AND IMMUNOASSAY

(71) Applicant: Chemclin Diagnostics Co., Ltd., Beijing (CN)

(72) Inventors: Yang Yang, Shanhai (CN); Xianghui Zhang, Shanhai (CN); Zifu Lian, Shanghai (CN); Guidong Liu, Beijing (CN); Dongyang Wu, Beijing (CN); Weiguo Zhao, Shanghai (CN); Yuhui Liu, Beijing (CN); Lin Li, Beijing (CN)

(73) Assignee: Chemclin Diagnostics Co., Ltd., Beijing (CN)

( * ) Notice: Subject to any disclaimer, the term of this patent is extended or adjusted under 35 U.S.C. 154(b) by 643 days.

This patent is subject to a terminal disclaimer.

(21) Appl. No.: 16/462,968

(22) PCT Filed: Nov. 21, 2017

(86) PCT No.: PCT/CN2017/112145
§ 371 (c)(1),
(2) Date: May 22, 2019

(87) PCT Pub. No.: WO2018/095314
PCT Pub. Date: May 31, 2018

(65) Prior Publication Data
US 2019/0353664 A1 Nov. 21, 2019

(30) Foreign Application Priority Data

| Nov. 22, 2016 | (CN) | 201611026623.1 |
| Nov. 22, 2016 | (CN) | 201611034237.7 |
| Nov. 22, 2016 | (CN) | 201611034252.1 |
| Aug. 15, 2017 | (CN) | 201710695530.6 |

(51) Int. Cl.
*G01N 33/543* (2006.01)
*G01N 21/76* (2006.01)
*G16B 25/10* (2019.01)

(52) U.S. Cl.
CPC ....... *G01N 33/54393* (2013.01); *G01N 21/76* (2013.01); *G16B 25/10* (2019.02)

(58) Field of Classification Search
CPC .......... G01N 33/54393; G01N 21/76
See application file for complete search history.

(56) References Cited

U.S. PATENT DOCUMENTS

| 2008/0213797 A1 | 9/2008 | Konrath et al. |
| 2014/0186216 A1* | 7/2014 | Campbell ........ G01N 33/54393 422/69 |
| 2021/0208080 A1* | 7/2021 | Yang .................... G01N 33/582 |

FOREIGN PATENT DOCUMENTS

| CN | 101055272 A | 10/2007 |
| CN | 101326440 A | 12/2008 |
| CN | 101666801 A | 3/2010 |
| CN | 201532646 U | 7/2010 |
| CN | 102341706 A | 2/2012 |
| CN | 102944672 B | 5/2015 |
| CN | 104991056 A | 10/2015 |
| EP | 1219964 A1 | 7/2002 |
| EP | 2790019 A1 | 10/2014 |
| GB | 2203836 A | 10/1988 |
| JP | S6396557 A | 4/1988 |
| JP | H0510953 A | 1/1993 |
| JP | 2002214237 A | 7/2002 |
| JP | 2007536500 A | 12/2007 |
| WO | 9825143 A1 | 6/1998 |
| WO | 2005010489 A2 | 2/2005 |
| WO | 2009126336 A1 | 10/2009 |
| WO | 2009144507 A1 | 12/2009 |
| WO | 2011016326 A1 | 2/2011 |

OTHER PUBLICATIONS

Balke et al. (EP 2790019 A1) High Dose Hook Detection—machine translation.*
Li et al. (CN 104991056 A1) Method of serological test and quantitative analysis.*
Campbell et al. (CN 104969069) Apparatus and method for identifying dynamic range of hook-like effects and expanding timely on-site care immunoassay.*
International search report of PCT Patent Application No. PCT/CN2017/112145 issued on Feb. 24, 2018.
Hongwei Ma et al., Development of Serum Cardiac Troponin I Light Induced Chemiluminescent Immunoassay, Laboratory Medicine, Dec. 31, 2007, pp. 398-401, vol. 22, No. 4.
Amarasiri Fernando, S. et al.; "Studies of the 'hook' effect in the one-step sandwich immunoassay"; Journal of immunological Methods, vol. 151; Year: 1992; pp. 47-66.

* cited by examiner

*Primary Examiner* — Gailene Gabel
(74) *Attorney, Agent, or Firm* — NKL Law; Bin Lu

(57) ABSTRACT

Related to is the technical field of light initiated chemiluminescence technology, and in particular, to a method for determining HD-Hook-effect sample, a system, a reagent kit, and a device for determining HD-Hook effect in immunoassay, an immunoassay method, a system, a reagent kit, and a device for determining immunoassay.

5 Claims, 15 Drawing Sheets

METHOD, SYSTEM, REAGENT KIT, AND DEVICE FOR DETERMINING HD-HOOK-EFFECT SAMPLE AND IMMUNOASSAY

CROSS-REFERENCE TO RELATED APPLICATIONS

This application claims the priority of Chinese patent application CN 201611026623.1, entitled "Immunoassay method, and system and reagent kit for determining immunoassay" and filed on Nov. 22, 2016, the entirety of which is incorporated herein by reference.

This application claims the priority of Chinese patent application CN 201611034237.7, entitled "Immunoassay method, and system and reagent kit for determining immunoassay" and filed on Nov. 22, 2016, the entirety of which is incorporated herein by reference.

This application claims the priority of Chinese patent application CN 201611034252.1, entitled "Method for determining HD-Hook-effect sample, and system for determining HD-Hook effect in immunoassay" and filed on Nov. 22, 2016, the entirety of which is incorporated herein by reference.

This application claims the priority of Chinese patent application CN 201710695530.6, entitled "Immunoassay device" and filed on Aug. 15, 2017, the entirety of which is incorporated herein by reference.

FIELD OF THE INVENTION

The present disclosure relates to the technical field of light initiated chemiluminescence technology, and in particular, to a method for determining HD-Hook-effect sample, a system, a reagent kit, and a device for determining HD-Hook effect in immunoassay, an immunoassay method, a system, a reagent kit, and a device for determining immunoassay.

BACKGROUND OF THE INVENTION

An immunoassay relies on an antigen-antibody interaction. It is usually used to detect trace bioactive substances such as proteins, hormone, etc, because it is capable of using isotopes, enzymes, and chemiluminescent substances and so on to detect an analyte or to magnify a signal.

Chemiluminescent immunoassay is a non-radioactive immunoassay evolved rapidly in recent years. It uses chemiluminescent substance(s) to magnify a signal associated directly with the binding of an antibody to an antigen, thus to detect the binding process through the luminescent intensity of the chemiluminescent substance(s). Chemiluminescent immunoassay has become one of the most important techniques in the field of immunoassay.

Light initiated chemiluminescent assay is a common technique applied in the field of chemiluminescent immunoassay. It can be used to study the interactions of biomolecules.

Clinically, it is mostly utilized for the detection of diseases. Light initiated chemiluminescent assay utilizes and integrates the knowledge of many related fields especially macromolecular particles, organic synthesis, protein chemistry and clinical detection. In a light initiated chemiluminescent assay, light-sensitive and light-emitting particles bind to each other within certain range through an immuno-interaction, which enables the transferring of ionized oxygen energy to the light-emitting dye to emit the light, thus to detect the immuno-interaction or an analyte responsible for the immuno-interaction in a sample. The light-sensitive particles are filled with a light-sensitive compound, and the light-emitting particles are filled with a light-emitting compound and a lanthanide complex. The light-sensitive particles release high energy-state singlet oxygen ions (4 $\mu$S) after being activated with laser beam with specific wavelength (600-700 nm). A travelling distance of the ions is about 200 nm. When the light-sensitive particles and the light-emitting particles are close enough to each other, the singlet oxygen ions released by the light-sensitive particles are capable of reaching the light-emitting particles and emitting, after series of chemical reactions, high energy-level light of 520 nm to 620 nm, which is then detected by a device. In the aforesaid reaction system, the concentration of the particles is very small, and therefore there is very little chance that the particles can collide with one another, and the background signal is very weak. It is only when the light-sensitive particles and the light-emitting particles bind together after an immunoreaction that an apparent light can be emitted. The system is therefore highly sensitive. In diagnosis of diseases, a common assay usually requires three to four components: light-emitting particles coated with an antigen or an antibody, an antigen or antibody labeled with biotin or digoxin, light-sensitive particles coated with avidin or anti-digoxin, a neutralizing antigen or antibody, etc. These components bind an antigen to be detected or an antibody to be detected after more than two steps of incubation, and a sample to be detected is thus qualitatively or quantitatively assayed based on intensity of the chemiluminescence. Compared with traditional enzyme-linked immuno sorbent assay (ELISA), light initiated chemiluminescent assay is homogeneous, more sensitive, easier to operate and more automatic, and thus can found wide applications in the future.

In a double-antibody sandwich assay, when the concentration of an analyte reaches a certain value, no double-antibody sandwich complex can be formed, and a low signal is therefore observed. This phenomenon is called high dose hook effect (HD-Hook effect). In other words, HD-Hook effect refers to a phenomenon where in a double-site sandwich immunoassay, the linear orientation of a high dose section of a dose response curve does not rise indefinitely, but drops like a hook, resulting in false negatives.

HD-Hook effect occurs frequently in immunoassays, and its occurrence rate accounts for 30% of positive samples. Due to HD-Hook effect, one cannot tell whether a concentration of a sample to be detected has exceeded the linear range of the assay kit or the concentration of the sample is really the detected value. The occurrence rate of false negatives is thus increased.

Specifically, on the one hand, when a high concentration sample is detected, HD-Hook effect may lead to a low detection signal, and consequently it would be determined that the sample has a low concentration. A conventional approach to solve this problem is to add a component to the reagent, to dilute the sample to be detected or to use a two-step assay.

On the other hand, due to the HD-Hook effect, when the concentration of the sample is increased to a certain value, the signal cannot become higher and higher continuously. This limits the detection range. Conventionally, the detection range is expanded mainly by optimizing or increasing the antibody.

A conventional assay process comprises the following five steps: adding an analyte and a reagent into a reaction well to form a mixture; incubating the mixture for a first time; adding a general-purpose solution; incubating the mixture for a second time; and performing value reading.

The assay method of the present disclosure is based on the conventional assay process. During the assay of the present disclosure, values of a signal are read for multiple times during a reaction without interrupting the reaction. A real concentration of a sample is thus determined by observing variations of the signal.

SUMMARY OF THE INVENTION

In view of the defects of the existing techniques, the present disclosure has an object to provide an immunoassay method, according to which a detection range can be expanded by two times of value reading without interrupting a reaction, whether HOOK effect exists with a sample to be detected can be accurately determined, and a concentration of an analyte in the sample can be easily calculated.

In order to achieve the above object, the present disclosure adopts the following technical solutions.

The present disclosure, at one aspect, provides a method for determining an HD-Hook-effect sample. The method comprises steps of: subjecting a calibrator, a peak-value calibrator, and a sample to be detected containing a target antigen (or antibody) to be detected to a chemiluminescent immunoreaction; initiating chemiluminescence, recording a first-time-read-value and a second-time-read-value the chemiluminescence, and marking a growth rate A from a first-time-read-value to a second-time-read-value with respect to the peak-value calibrator as R0; and comparing a growth rate A' from the first-time-read-value to the second-time-read-value with respect to the sample to be detected with R0 to see whether the growth rate A' is larger than R0 or not, wherein if the growth rate A' is larger than R0, it is determined that HD-Hook effect is present in the sample, and if the growth rate A' is smaller than R0, it is determined that HD-Hook effect is not present in the sample.

It shall be noted that the growth rate with respect to the sample to be detected and the growth rate with respect to the peak-value calibrator are obtained trough reactions under same conditions and of same reaction time. According to one preferred embodiment of the present disclosure, the method comprises the following steps of:

(1) mixing the calibrator, the peak-value calibrator, and the sample to be detected containing the target antigen (or antibody) to be detected with light-emitting particles coated with a primary antibody (or antigen), and a secondary antibody (or antigen) labeled with a label to form a mixture, and incubating the mixture to obtain a mixed solution;

(2) performing a first-time-value-reading, which specifically comprises: adding light-sensitive particles labeled with a binding conjugate specific to the label of the secondary antibody (or antigen) into the mixed solution obtained in step (1); incubating the mixed solution; then irradiating the mixed solution and detecting the amount of light emitted by the mixed solution; and reading a value with a photon counter and marking the value as RLU1;

(3) performing a second-time-value-reading, which specifically comprises: incubating the mixed solution after the first-time-value-reading performed in step (2) again; then irradiating the mixed solution and detecting the amount of light emitted by the mixed solution; and reading a value with a photon counter and marking the value as RLU2;

(4) calculating the growth rate A' from a signal value obtained at the first-time-value-reading to a signal value obtained at the second-time-value-reading with respect to the sample based on equation A'=(RLU2/RLU1−1)×100%;

(5) marking a growth rate A from a first-time-read-value to a second-time-read-value with respect to the peak-value calibrator as R0; and (6) comparing the growth rate A' from the first-time-read-value to the second-time-read-value with respect to the sample to be detected with R0, wherein if the growth rate A' is larger than R0, it is determined that the sample is an HD-Hook-effect sample.

As used herein, the term "peak-value calibrator" refers to a sample containing an analyte of a certain concentration at which a linear direction of a high dose section of a dose response curve of the analyte starts to drop in a double-antibody sandwich immunoassay.

According to one preferred embodiment of the present disclosure, the growth rate A' from the first-time-read-value to the second-time-read-value with respect to the sample to be detected is compared with R0. If the growth rate A' is larger than R0, it is determined that the sample is an HD-Hook-effect sample and that the sample needs to be diluted; and if the growth rate A' is smaller than R0, a concentration of the sample is directly calculated using a calibration curve. The calibration curve is a curve plotted based on the first-time-read-value with respect to the calibrator and a concentration of the calibrator.

According to one preferred embodiment of the present disclosure, the light-emitting particles are macromolecules that are filled with a light-emitting compound and a lanthanide, and the light-sensitive particles are macromolecules that are filled with a light-sensitive compound, the light-sensitive particles being capable of generating singlet oxygen ions in response to the irradiation of a red laser beam.

According to one preferred embodiment of the present disclosure, in steps (2) and (3), the mixed solution is irradiated with a red laser beam of 600-700 nm, and the amount of light emitted by the mixed solution is detected. A wavelength that is detected of the light emitted is 520-620 nm.

According to one preferred embodiment of the present disclosure, the antigen refers to an immunogenic substance, the antibody refers to an immunoglobulin that is produced by an organism and is capable of recognizing a unique foreign substance; the primary antibody and the secondary antibody each refer to an antibody that is capable of specifically binding to the target antigen; and the primary antigen and the secondary antigen each refer to an antigen that is capable of specifically binding to the target antibody.

The present disclosure, at a second aspect, provides a system for determining HD-Hook effect in an immunoassay. The system comprises: an immunoreaction device, which is configured to conduct a chemiluminescent immunoreaction therein; a chemiluminescent-immunoreaction initiating and recording device, which is configured to initiate chemiluminescence and record a first-time-read-value and a second-time-read-value with respect to the chemiluminescence; and a processor, which is configured to determine the presence of an HD-Hook-effect sample based on a growth rate A' from a first-time-read-value to a second-time-read-value with respect to a sample to be detected.

According to one preferred embodiment of the present disclosure, the system comprises: an immunoreaction device, which is configured to conduct a chemiluminescent immunoreaction therein; a chemiluminescent-immunoreaction initiating and recording device, which is configured to initiate chemiluminescence and record a first-time-read-value and a second-time-read-value with respect to the chemiluminescence; and a processor, which is configured to compare a growth rate A' from a first-time-read-value to a second-time-read-value with respect to a sample to be detected with a growth rate R0 from a first-time-read-value to a second-time-read-value with respect to a peak calibration, to see whether the growth rate A' is larger than R0 or not. If the growth rate A' is larger than R0, it is determined that HD-Hook effect is present in the sample, and if the growth rate A' is smaller than R0, it is determined that HD-Hook effect is not present in the sample. The second-time-read-value with respect to the chemiluminescence is obtained by initiating and recording a same immunoreaction again after the immunoreaction proceeds for a period of time.

In one specific embodiment, a system for determining an immunoassay of the present disclosure comprises: an immunoreaction device which is, for example, a vessel for containing a solution; a chemiluminescent-immunoreaction initiating and recording device which is, for example, a photon counter module and a light-emitting diode; and a processor which is, for example, a computer, used to process values read and draw curves. Such a system for determining an immunoassay can be found, for example, in utility model CN201532646U filed by the applicant of the present disclosure, which is incorporated herein by reference.

According to a preferred embodiment of the present disclosure, a method of using the system comprises steps of:

(1) mixing a calibrator, a peak-value calibrator, and a sample to be detected containing a target antigen (or antibody) to be detected with light-emitting particles coated with a primary antibody (or antigen), and a secondary antibody (or antigen) labeled with a label to form a mixture, and incubating the mixture to obtain a mixed solution;

(2) performing a first-time-value-reading, which specifically comprises: adding light-sensitive particles labeled with a binding conjugate specific to the label of the secondary antibody (or antigen) into the mixed solution obtained in step (1); incubating the mixed solution; then irradiating the mixed solution and detecting the amount of light emitted by the mixed solution; and reading a value with a photon counter and marking the value as RLU1;

(3) performing a second-time-value-reading, which specifically comprises: incubating the mixed solution after the first-time-value-reading performed in step (2) again; then irradiating the mixed solution and detecting the amount of light emitted by the mixed solution; and reading a value with a photon counter and marking the value as RLU2;

(4) calculating a growth rate A' from a signal value obtained at the first-time-value-reading to a signal value obtained at the second-time-value-reading with respect to the sample to be detected based on equation $A'=(RLU2/RLU1-1)\times 100\%$;

(5) marking a growth rate A from a first-time-read-value to a second-time-read-value with respect to the peak-value calibrator as R0; and (6) comparing the growth rate A' from the first-time-read-value to the second-time-read-value with respect to the sample to be detected with R0, wherein if the growth rate A' is larger than R0, it is determined that the sample is an HD-Hook-effect sample.

According to the present disclosure, the growth rate A' from the first-time-read-value to the second-time-read-value with respect to the sample to be detected is compared with R0. If the growth rate A' is larger than R0, it is determined that the sample is an HD-Hook-effect sample and that the sample needs to be diluted; and if the growth rate A' is smaller than R0, a concentration of the sample is directly calculated using a calibration curve. The calibration curve is a curve plotted based on the first-time-read-value with respect to the calibrator and a concentration of the calibrator.

The present disclosure, at a third aspect, provides reagent kit comprising a calibrator, a peak-value calibrator, light-emitting particles coated with a primary antibody (or antigen), a secondary antibody (or antigen) labeled with a label, light-sensitive particles labeled with a binding conjugate specific to the label of the secondary antibody (or antigen). A method of using the reagent kit comprises steps of: subjecting the calibrator, the peak-value calibrator, and a sample to be detected containing a target antigen (or antibody) to be detected to a chemiluminescent immunoreaction; initiating chemiluminescence and recording a first-time-read-value and a second-time-read-value with respect to the chemiluminescence; and determining the presence of an HD-Hook-effect sample based on a growth rate A' from the first-time-read-value to the second-time-read-value with respect to the sample to be detected.

According to one preferred embodiment of the present disclosure, a method of using the reagent kit comprises steps of: subjecting the calibrator, the peak-value calibrator, and a sample to be detected containing a target antigen (or antibody) to be detected to a chemiluminescent immunoreaction; initiating chemiluminescence and recording a first-time-read-value and a second-time-read-value with respect to the chemiluminescence; and comparing a growth rate A' from the first-time-read-value to the second-time-read-value with respect to the sample to be detected with a growth rate R0 from a first-time-read-value to a second-time-read-value with respect to the peak-value calibrator, to see whether the growth rate A' is larger than R0 or not, wherein if the growth rate A' is larger than R0, it is determined that HD-Hook effect is present in the sample, and if the growth rate A' is smaller than R0, it is determined that HD-Hook effect is not present in the sample.

According to one preferred embodiment of the present disclosure, a method of using the reagent kit comprises steps of:

(1) mixing the calibrator, the peak-value calibrator, and a sample to be detected containing a target antigen (or antibody) to be detected with light-emitting particles coated with a primary antibody (or antigen), and a secondary antibody (or antigen) labeled with a label to form a mixture, and incubating the mixture to obtain a mixed solution;

(2) performing a first-time-value-reading, which specifically comprises: adding light-sensitive particles labeled with a binding conjugate specific to the label of the secondary antibody (or antigen) into the mixed solution obtained in step (1); incubating the mixed solution; then irradiating the mixed solution and detecting the amount of light emitted by the mixed solution; and reading a value with a photon counter and marking the value as RLU1;

(3) performing a second-time-value-reading, which specifically comprises: incubating the mixed solution after the first-time-value-reading performed in step (2) again; then irradiating the mixed solution and detecting the amount of light emitted by the mixed solution; and reading a value with a photon counter and marking the value as RLU2;

(4) calculating a growth rate A' from a signal value obtained at the first-time-value-reading to a signal value obtained at the second-time-value-reading with respect to the sample based on equation $A'=(RLU2/RLU1-1)\times 100\%$;

(5) marking a growth rate A from a first-time-read-value to a second-time-read-value with respect to the peak-value calibrator as R0; and (6) comparing the growth rate A' from the first-time-read-value to the second-time-read-value with respect to the sample to be detected with R0, wherein if the growth rate A' is larger than R0, it is determined that the sample is an HD-Hook-effect sample.

According to one preferred embodiment of the present disclosure, the growth rate A' from the first-time-read-value to the second-time-read-value with respect to the sample to be detected is compared with R0. If the growth rate A' is larger than R0, it is determined that the sample is an HD-Hook-effect sample and that the sample needs to be diluted; and if the growth rate A' is smaller than R0, a concentration of the sample is directly calculated using a calibration curve. The calibration curve is a curve plotted based on the first-time-read-value with respect to the calibrator and a concentration of the calibrator.

It shall be particularly noted that the above method are not for diagnosis of diseases, but for easy and rapid selection of HD-Hook-effect samples during a double-antibody sandwich immunoassay or double-antigen sandwich immunoassay, so as to avoid inaccurate detection of a high-concentration antigen (or antibody) sample as a low-concentration antigen (or antibody) sample.

Preferably, the antigen refers to an immunogenic substance such as proteins and polypeptides. Typical antigens include (but not limited to): cytokines, tumor makers, metalloproteins, cardiovascular disease and glycuresis related proteins.

The antigen refers to an immunoglobulin that is produced by an organism and is capable of recognizing a unique foreign substance.

In the embodiments of the present disclosure, the antigen or antibody is selected from epatitis B surface antigen (HBsAg), epatitis B surface antibody (HBsAb), cancer antigen 125 (CA125), ferritin, (Ferr), and C-peptide (CP).

Samples that can be detected by the method of the present disclosure are not limited herein. They can be any samples containing a target antigen (or antibody) to be detected. Typical examples of such samples include serum samples, urine samples, saliva samples, etc. Preferred samples used in the present disclosure are serum samples.

Preferably, the primary and secondary antibodies each are an antibody that can specifically bind to the antigen.

For a same antigen, corresponding primary and secondary antibodies can be the same or different, and can bind to the antigen simultaneously.

The primary and secondary antigens each are an antigen that can specifically bind to the target antibody.

For a same antibody, corresponding primary and secondary antigens can be the same or different, and can bind to the antibody simultaneously.

Preferably, the label and the binding conjugate specific to the label of the secondary antibody (or antigen) can specifically bind to each other.

More preferably, the label is biotin, and the binding conjugate specific to the label of the secondary antibody (or antigen) is streptavidin.

Preferably, the light-emitting particles are macromolecules that are filled with a light-emitting compound and a lanthanide compound. The light-emitting compound may be a derivative of dioxene or thioxene, and the lanthanide compound may be Eu(TTA)3/TOPO or Eu (TTA)3/Phen. The light-emitting particles are available on the market. A surface functional group of the light-emitting particles may be any group that can bind to a protein. Examples are known functional groups such as carboxyl group, aldehyde group, amidogen, epoxy ethyl, or halogen alkyl that can bind to a protein.

Preferably, the light-sensitive particles are macromolecules that are filled with a light-sensitive compound. The light-sensitive particles are capable of generating singlet oxygen ions in response to the irradiation of a red laser beam. When the light-sensitive particles are close enough to the light-emitting particles, the singlet oxygen ions travel to the light-emitting particles and react with the light-emitting compound within the light-emitting particles, and then the light-emitting compound emits ultraviolet light. The ultraviolet light then excites the lanthanide compound which then emits photons having a certain wavelength. The light-sensitive compound may be phthalocyanine and is available on the market.

Preferably, in steps (2) and (3), the mixed solution is irradiated with a red laser beam of 600-700 nm, and the amount of light emitted by the mixed solution is detected. A wavelength that is detected of the light emitted is 520-620 nm.

Further, when the red laser beam of 600-700 nm irradiates the light-sensitive particles, some of the singlet oxygen ions generated by the light-sensitive particles travel to the light-emitting particles and then the light-emitting particles emits emit high energy-state light of 520-620 nm.

In a detection range, the concentration of the target antigen to be detected is reflected by the number of the double-antibody sandwich complex and is in direct proportion to the number of the photons. When the concentration of the target antigen to be detected is too high, some of the antigens to be detected bind to a single antibody, as a consequence of which less double-antibody sandwich complexes are formed. This leads to a low light signal which cannot accurately reflect the real concentration of the target antigen to be detected.

Similarly, in the detection range, the concentration of the target antibody to be detected is reflected by the number of the double-antigen sandwich complex and is in direct proportion to the number of the photons. When the concentration of the target antibody to be detected is too high, some of the antibodies to be detected bind to a single antigen, as a consequence of which less double-antigen sandwich complexes are formed. This leads to a low light signal which cannot accurately reflect the real concentration of the target antibody to be detected.

The method of the present disclosure can expand the detection range and determine an HD-Hook effect sample by performing two times of value reading and then observing a growth rate from a first-time-read-value to a second-time-read-value. A difference between the first-time-read-value and the second-time-read-value is influenced by the following three aspects.

First, during the first-time-value-reading, some of the singlet oxygen ions generated by the light-sensitive particles in response to the irradiation of the red laser beam of 600-700 nm travel to the light-emitting particles and emit, after series of chemical reactions, high energy-level light of 520 nm to 620 nm. Other singlet oxygen ions react with the target antigen (or antibody) to be detected that is not bound by the antibody (or antigen), thereby reducing the concentration of the target antigen (or antibody) to be detected. For a low-concentration sample, after the concentration of the target antigen (or antibody) to be detected is reduced, less double-antibody sandwich complexes are formed, and therefore a signal value obtained at the second-time-value-reading is smaller. For a high-concentration HD-Hook-effect sample, after the concentration of the target antigen (or antibody) to be detected is reduced, more double-antibody sandwich complexes are formed, and therefore a signal value obtained at the second-time-value-reading is larger.

Second, for a low-concentration sample, during the first-time-value-reading, the light-emitting particles generate singlet oxygen ions when irradiated by the red laser beam (600-700 nm) and some energy thereof is consumed. That is why the signal value obtained at the second-time-value-reading is smaller.

Third, for a high-concentration HD-Hook-effect sample, during the first-time-value-reading, the antigen-antibody reaction does not reach equilibrium, and during an interval between the two times of value reading, the reaction keeps proceeding in a forward direction. That is why the signal value obtained at the second-time-value-reading is larger.

To summarize, in the present disclosure, on the one hand, when the reaction does not reach equilibrium, some of the singlet oxygen ions generated by the light-sensitive particles in response to the irradiation of the red laser beam travel to the light-emitting particles, and other singlet oxygen ions react with the target antigen (or antibody) to be detected that is not bound so that part of the target antigen (or antibody) to be detected is consumed. In this way, the equilibrium of the reaction is shifted in a reverse direction. On the other hand, when the light-sensitive particles undergo an irradiation, the energy thereof is consumed, and therefore the signal value with respect to the target antigen (or antibody) to be detected obtained at the second-time-value-reading is smaller. For a high-concentration sample, during the first-time-value-reading, the binding between the double-antibody sandwich complexes and the light-sensitive particles is far from equilibrium, and during the second-time-value-reading, the reaction shifts in the forward direction, and therefore the signal value is larger. As the concentration of the target antigen (or antibody) to be detected increases, the growth rate from the signal value obtained after the second irradiation to the signal value obtained after the first irradiation is also increased. The growth rate of the signal value is in a positive correlation to the concentration of the sample. By observing the growth rate with respect to two signal values, it can be determined that a sample having a small signal value but a large growth rate is an HD-Hook-effect sample.

The present disclosure, at a fourth aspect, provides an immunoassay device for determining an HD-Hook-effect sample, comprising: a reading unit, which is configured to record a chemiluminescent immunoreaction and perform multiple times of value reading with respect to an incubated mixed solution; and a processing unit, which is connected with the reading unit and is configured to determine presence of risk of HD-Hook effect in an immunoassay based on values read by the reading unit.

In some embodiments of the present disclosure, the immunoassay device further comprises a transferring mechanism, which is configured to transfer the incubated mixed solution to the reading unit for value reading.

In some embodiments of the present disclosure, the immunoassay device further comprises an incubator, which is configured to provide a suitable temperature for the chemiluminescent immunoreaction.

In some other embodiments of the present disclosure, the immunoassay device further comprises a returning mechanism, which is configured to return the mixed solution after value reading to the incubator for a second incubation.

In some specific embodiments of the present disclosure, the transferring mechanism is a pushing mechanism and the returning mechanism is a pushback mechanism, and the mixed solution is contained in a plate.

In some other specific embodiments of the present disclosure, the reading unit is configured to record the chemiluminescent immunoreaction and perform two times of value reading with respect to the incubated mixed solution.

In some specific embodiments of the present disclosure, the incubator comprises a first incubator and a second incubator. The pushing mechanism is configured to push the mixed solution incubated in the first incubator to the second incubator for incubation, and is further configured to push the mixed solution incubated in the second incubator to the reading unit for a first-time-value-reading. The pushback mechanism is configured to push the mixed solution after the first-time-value-reading back to the second incubator for a second incubation. The pushing mechanism is further configured to push the mixed solution incubated in the second incubator to the reading unit for a second-time-value-reading. When the processing unit detects that a growth rate A from a first-time-read-value to a second-time-read-value is larger than a maximum value of a standard curve, it is determined that HD-Hook-effect risk is present in the immunoassay.

In some other specific embodiments of the present disclosure, the pushback mechanism comprises: a base plate; a guide rail provided on the base plate; a moving-cup mechanism which is provided on the guide rail and is configured to accommodate plates; a drive device configured to drive the moving-cup mechanism to move along the guide rail; photoelectric sensors which are provided on both ends of the base plate and are configured to detect a position of the moving-cup mechanism; and a position adjustment mechanism which is connected with the photoelectric sensor and is configured to adjust the position of the moving-cup mechanism based on a position signal generated by the photoelectric sensor.

In some specific embodiments of the present disclosure, the guide rail is a straight rail or a variable rail.

In some specific embodiments of the present disclosure, the device further comprises: a sample-addition tray which is provided on one side of the incubator and where a sample to be detected and reagents are mixed; and a reagent-refrigerating area which is provided on another side of the incubator and is configured to store reagents.

In some other specific embodiments of the present disclosure, the device further comprises: a blank plate stacking and loading mechanism which is provided on a side of the sample-addition tray and is configured to push blank plates to the sample-addition tray.

In some specific embodiments of the present disclosure, the device further comprises a sample test-tube rack configured to hold sample test-tubes.

In some other specific embodiments of the present disclosure, the device further comprises: a dilution-plate oscillator which is provided on a side of the sample test-tube rack close to the blank plate stacking and loading mechanism and is configured to oscillate a pre-dilution plate.

In some specific embodiments of the present disclosure, the device further comprises a mechanical arm which is provided with a sampling probe. The mechanical arm comprises a first mechanic arm and a second mechanic arm. The first mechanic arm is configured to draw up a sample from the sample test-tube rack and to dispense the sample into a plate in the sample-addition tray. The second mechanic arm is configured to draw up a reagent from the reagent-refrigerating area and to dispense the reagent into a plate in the sample-addition tray.

In some other specific embodiments of the present disclosure, the device further comprises: a first cleaning mechanism and a second cleaning mechanism. The first cleaning mechanism is configured to clean a sampling probe on the first mechanical arm, and the second cleaning mechanism is configured to clean a sampling probe on the second mechanical arm.

Specifically, before being put into the incubator, the sample undergoes the following steps.

1. Blank plates are transferred by the blank plate stacking and loading mechanism to a position D0 of the sample-addition tray.

2. After the blank plates are transferred to the position D0 of the sample-addition tray, the blank plates are clockwise rotated with the sample-addition tray by 90 degree to a position D1 of the sample-addition tray. At this moment, the first mechanic arm draws up the sample from the sample test-tube rack and dispenses the sample to the blank plates.

3. After dispensing of the sample to the blank plates, the plates having the sample are clockwise rotated with the sample-addition tray by 90 degree to a position D2 of the sample-addition tray. No operation is conducted at this position.

4. The plates having the sample are then clockwise rotated with the sample-addition tray by 90 degree to a position D3 of the sample-addition tray. At this moment, the second mechanic arm draws up the reagent from the reagent-refrigerating area and dispenses the regent to the plates at this position.

After all the plates having the sample at the position D3 are added with the reagent and are transferred to the incubator (not shown in the FIGS.), the sample-addition tray is rotated from the position D3 to the position D0 (this should be conducted after the addition of sample to the blank plates at the position D1 is finished). The sample-addition tray thus finishes one cycle. When the sample-addition tray is operated at a full load, blank plates are loaded at the position D0; the sample is dispensed at the position D1; no operation is done at the position D2; and the reagent is dispensed at the position D3 from which the plates after reagent dispensing are transferred to the incubator. The rotation of the sample-addition tray is performed after operations at positions D0-D3 are all finished.

After the plates having the sample and reagent are incubated in the first incubator, the pushing mechanism pushes the plates to the second incubator, during which process light-sensitive particles labeled with a specific binding conjugate specific to the label of the secondary antibody (or antigen) are added to the plate having the sample and reagent to be detected. After that, the plates are incubated in the second incubator and then pushed by the pushing mechanism to the reading unit to undergo irradiation by a laser beam. The amount of light emitted is detected and a first-time-read-value is recorded. After the first-time-value-reading, the plates are pushed back by the pushback mechanism to the second incubator for a second incubation. After the second incubation, the plates are again pushed by the pushing mechanism to the reading unit to undergo irradiation by a laser beam. The amount of light emitted is detected and a second-time-read-value is recorded. After the two times of value reading are finished, the processing unit processes the first-time-read-value and the second-time-read-value. When a growth rate from the first-time-read-value to the second-time-read-value is larger than a maximum value of the standard curve, it is determined that HD-Hook effect is present in the immunoassay. One approach is to let the device give a qualitative reminder of HD-Hook effect, and an operator then dilutes the sample before detecting the sample. Another approach is to let the device give a quantitative result, but the result is much higher than the linear range.

Compared with existing technologies, the device provided by the present disclosure determines the presence of HD-Hook effect risk in an immunoassay by using the reading unit to conduct two or even more times of value readings with respect to the incubated mixed solution and by using the processing unit to process the values read by the reading unit. This helps to avoid the situation in which due to HD-Hook effect, one cannot tell whether a concentration of a sample to be detected has exceeded the linear range of an assay kit or the concentration of the sample is really the detected value. Inaccurate detection results are thus avoided.

The present disclosure, at a fifth aspect, provides an immunoassay method comprising steps of: (1) subjecting a sample to be detected containing a target antigen (or antibody) to be detected to a chemiluminescent immunoreaction, initiating chemiluminescence, recording a first-time-read-value and a second-time-read-value with respect to the chemiluminescence, and marking a growth rate from the first-time-read-value to the second-time-read-value as A; (2) plotting a standard curve based on growth rates A' from first-time-read-values to second-time-read-values with respect to a series of known standard substances containing the target antigen (or antibody), and/or making a standard based on a growth rate A" from a first-time-read-value to a second-time-read-value with respect to a known standard substance containing the target antigen (or antibody); and (3) comparing the growth rate A from the first-time-read-value to the second-time-read-value with respect to the sample to be detected containing the target antigen (or antibody) to be detected with the standard curve and/or the standard.

It shall be noted that the growth rate with respect to the sample to be detected and the growth rate with respect to the peak-value calibrator are obtained trough reactions under same conditions and of same reaction time.

In some embodiments of the present disclosure, the growth rate A from the first-time-read-value to the second-time-read-value with respect to the sample to be detected containing the target antigen (or antibody) to be detected is compared with the standard curve.

In some embodiments of the present disclosure, concentrations of the known standard substances are lower than a concentration at which HD-Hook effect occurs, and the known standard substances are used in a positive control.

In some other embodiments of the present disclosure, the method further comprises a step (4): diluting the sample to be detected before detection if the growth rate A from the first-time-read-value to the second-time-read-value with respect to the sample to be detected containing the target antigen (or antibody) to be detected is larger than a maximum value of the standard curve.

In some specific embodiments of the present disclosure, the method comprises steps of:

(a1) mixing the sample to be detected containing the target antigen (or antibody) to be detected with light-emitting particles coated with a primary antibody (or antigen), and a secondary antibody (or antigen) labeled with a label to form a mixture, and incubating the mixture to obtain a mixed solution;

(a2) performing a first-time-value-reading, which specifically comprises: adding light-sensitive particles labeled with a binding conjugate specific to the label of the secondary antibody (or antigen) into the mixed solution obtained in step (a1); incubating the mixed solution; then irradiating the mixed solution and detecting the amount of light emitted by the mixed solution; and reading a value with a photon counter and marking the value as RLU1;

(a3) performing a second-time-value-reading, which specifically comprises: incubating the mixed solution after the first-time-value-reading performed in step (a2) again; then irradiating the mixed solution and detecting the amount of light emitted by the mixed solution; and reading a value with a photon counter and marking the value as RLU2;

(a4) calculating a growth rate A from a signal value obtained at the first-time-value-reading to a signal value obtained at the second-time-value-reading with respect to the sample based on equation $A=(RLU2/RLU1-1)\times 100\%$;

(a5) plotting a standard curve based on the growth rates A' from the first-time-read-values to the second-time-read-values with respect to the series of known standard substances containing the target antigen (or antibody), wherein the concentrations of the standard substances are lower than the concentration at which HD-Hook effect occurs; and (a6) diluting the sample to be detected before detection if the growth rate A from the first-time-read-value to the second-time-read-value with respect to the sample to be detected containing the target antigen (or antibody) to be detected is larger than a maximum value of the standard curve.

In some embodiments of the present disclosure, the growth rate A from the first-time-read-value to the second-time-read-value with respect to the sample to be detected containing the target antigen (or antibody) to be detected is compared with the standard which is marked as a critical value, and/or the known substance is used as a positive control.

In some embodiments of the present disclosure, the method further comprises a step of: (4) determining that a concentration of the sample to be detected is larger than a concentration of the known standard substance if the growth rate A from the first-time-read-value to the second-time-read-value with respect to the sample to be detected containing the target antigen (or antibody) to be detected is larger than the critical value.

In some specific embodiments of the present disclosure, the method comprises steps of:

(c1) mixing the sample to be detected containing the target antigen (or antibody) to be detected with light-emitting particles coated with a primary antibody (or antigen), and a secondary antibody (or antigen) labeled with a label to form a mixture, and incubating the mixture to obtain a mixed solution;

(c2) performing a first-time-value-reading, which specifically comprises: adding light-sensitive particles labeled with a binding conjugate specific to the label of the secondary antibody (or antigen) into the mixed solution obtained in step (c1); incubating the mixed solution; then irradiating the mixed solution and detecting the amount of light emitted by the mixed solution; and reading a value with a photon counter and marking the value as RLU1;

(c3) performing a second-time-value-reading, which specifically comprises: incubating the mixed solution after the first-time-value-reading performed in step (c2) again; then irradiating the mixed solution and detecting the amount of light emitted by the mixed solution; and reading a value with a photon counter and marking the value as RLU2;

(c4) calculating a growth rate A from a signal value obtained at the first-time-value-reading to a signal value obtained at the second-time-value-reading with respect to the sample based on equation $A=(RLU2/RLU1-1)\times 100\%$;

(c5) setting the growth rate A" from the first-time-read-value to the second-time-read-value with respect to the known standard substance containing the target antigen (or antibody) as the critical value; and (c6) comparing the growth rate A from the first-time-read-value to the second-time-read-value with respect to the sample to be detected containing the target antigen (or antibody) to be detected with the critical value, wherein if the growth rate A is larger than the critical value, it is determined that the concentration of the sample to be detected is larger than the concentration of the known standard substance.

In some embodiments of the present disclosure, the method further comprises a step of: (4) diluting the sample to be detected before detection if the growth rate A from the first-time-read-value to the second-time-read-value with respect to the sample to be detected containing the target antigen (or antibody) to be detected is larger than the critical value and the first-time-read-value with respect to the sample to be detected is smaller than the first-time-read-value with respect to the known standard substance.

In some specific embodiments of the present disclosure, the method comprises steps of:

(d1) mixing the sample to be detected containing the target antigen (or antibody) to be detected with light-emitting particles coated with a primary antibody (or antigen), and a secondary antibody (or antigen) labeled with a label to form a mixture, and incubating the mixture to obtain a mixed solution;

(d2) performing a first-time-value-reading, which specifically comprises: adding light-sensitive particles labeled with a binding conjugate specific to the label of the secondary antibody (or antigen) into the mixed solution obtained in step (d1); incubating the mixed solution; then irradiating the mixed solution and detecting the amount of light emitted by the mixed solution; and reading a value with a photon counter and marking the value as RLU1;

(d3) performing a second-time-value-reading, which specifically comprises: incubating the mixed solution after the first-time-value-reading performed in step (d2) again; then irradiating the mixed solution and detecting the amount of light emitted by the mixed solution; and reading a value with a photon counter and marking the value as RLU2;

(d4) calculating a growth rate A from a signal value obtained at the first-time-value-reading to a signal value obtained at the second-time-value-reading with respect to the sample based on equation $A=(RLU2/RLU1-1)\times 100\%$;

(d5) setting the growth rate A" from the first-time-read-value to the second-time-read-value with respect to the known standard substance containing the target antigen (or antibody) as the critical value; and (d6) comparing the growth rate A from the first-time-read-value to the second-time-read-value with respect to the sample to be detected containing the target antigen (or antibody) to be detected with the critical value, wherein if the growth rate A is larger than the critical value and the first-time-read-value with respect to the sample to be detected is smaller than the first-time-read-value with respect to the known standard substance, the sample is diluted before being detected again.

In some specific embodiments of the present disclosure, the growth rate A from the first-time-read-value to the second-time-read-value with respect to the sample to be detected containing the target antigen (or antibody) is compared with the standard curve, and the method further comprises a step of: (4) determining a concentration of the sample.

In some specific embodiments of the present disclosure, the method comprises steps of:
- (b1) mixing the sample to be detected containing the target antigen (or antibody) to be detected with light-emitting particles coated with a primary antibody (or antigen), and a secondary antibody (or antigen) labeled with a label to form a mixture, and incubating the mixture to obtain a mixed solution;
- (b2) performing a first-time-value-reading, which specifically comprises: adding light-sensitive particles labeled with a binding conjugate specific to the label of the secondary antibody (or antigen) into the mixed solution obtained in step (b1); incubating the mixed solution; then irradiating the mixed solution and detecting the amount of light emitted by the mixed solution; and reading a value with a photon counter and marking the value as RLU1;
- (b3) performing a second-time-value-reading, which specifically comprises: incubating the mixed solution after the first-time-value-reading performed in step (b2) again; then irradiating the mixed solution and detecting the amount of light emitted by the mixed solution; and reading a value with a photon counter and marking the value as RLU2;
- (b4) calculating a growth rate A from a signal value obtained at the first-time-value-reading to a signal value obtained at the second-time-value-reading with respect to the sample based on equation $A=(RLU2/RLU1-1)\times 100\%$;
- (b5) plotting a standard curve based on the growth rates A' from the first-time-read-values to the second-time-read-values with respect to the series of known standard substances containing the target antigen (or antibody); and
- (b6) determining, based on the growth rate A, whether the concentration of the sample to be detected is located in a rising section or in a dropping section of the standard curve, and then calculating the concentration of the sample to be detected by putting the RLU1 of the sample to be detected in a corresponding calibration curve thereof.

According to the present disclosure, the light-emitting particles are macromolecules that are filled with a light-emitting compound and a lanthanide compound, and the light-sensitive particles are macromolecules that are filled with a light-sensitive compound. The light-sensitive particles are capable of generating singlet oxygen ions in response to the irradiation of a red laser beam.

According to the present disclosure, the mixed solution is irradiated with a red laser beam of 600-700 nm, and the amount of light emitted by the mixed solution is detected. A wavelength that is detected of the light emitted is 520-620 nm.

According to the present disclosure, the antigen refers to an immunogenic substance; the antibody refers to an immunoglobulin that is produced by an organism and is capable of recognizing a unique foreign substance; the primary antibody and the secondary antibody each refer to an antibody that is capable of specifically binding to the target antigen, and the primary antigen and the secondary antigen each refer to an antigen that is capable of specifically binding to the target antibody.

The present disclosure, at a sixth aspect, provides a system for determining an immunoassay. The system comprises: an immunoreaction device, which is configured to conduct a chemiluminescent immunoreaction therein; a chemiluminescent-immunoreaction initiating and recording device, which is configured to initiate chemiluminescence and record a first-time-read-value and a second-time-read-value with respect to the chemiluminescence, and to mark a growth rate from the first-time-read-value to the second-time-read-value as A; and a processor.

In a specific embodiment, the system for determining an immunoassay provided by the present disclosure comprises an immunoreaction device which is, for example, a vessel for containing a solution; a chemiluminescent-immunoreaction initiating and recording device which is, for example, a photon counter module and a light-emitting diode; and a processor which is, for example, a computer, used to process values read and draw curves. Such a system for determining an immunoassay can be found, for example, in utility model patent CN201532646U filed by the applicant of the present disclosure, which is incorporated herein by reference.

In some embodiments of the present disclosure, the processor is configured to plot a standard curve based on growth rates A from first-time-read-values to second-time-read-values with respect to a series of known standard substances containing a target antigen (or antibody). Concentrations of the standard substances are smaller than a concentration at which HD-Hook effect occurs. If a growth rate A from a first-time-read-value to a second-time-read-value with respect to a sample to be detected containing a target antigen (or antibody) is larger than a maximum value of the standard curve, the sample is diluted before being detected again.

In some embodiments of the present disclosure, a method of using the system comprises steps of:
- (1) mixing the sample to be detected containing a target antigen (or antibody) to be detected with light-emitting particles coated with a primary antibody (or antigen), and a secondary antibody (or antigen) labeled with a label to form a mixture, and incubating the mixture to obtain a mixed solution;
- (2) performing a first-time-value-reading, which specifically comprises: adding light-sensitive particles labeled with a binding conjugate specific to the label of the secondary antibody (or antigen) into the mixed solution obtained in step (1); incubating the mixed solution; then irradiating the mixed solution and detecting the amount of light emitted by the mixed solution; and reading a value with a photon counter and marking the value as RLU1;
- (3) performing a second-time-value-reading, which specifically comprises: incubating the mixed solution after the first-time-value-reading performed in step (2) again; then irradiating the mixed solution and detecting the amount of light emitted by the mixed solution; and reading a value with a photon counter and marking the value as RLU2;
- (4) calculating a growth rate A from a signal value obtained at the first-time-value-reading to a signal value obtained at the second-time-value-reading with respect to the sample based on equation A=(RLU2/RLU1−1)×100%;

(5) plotting the standard curve based on the growth rates A from the first-time-read-values to the second-time-read-values with respect to the series of known standard substances containing the target antigen (or antibody), wherein the concentrations of the standard substances are smaller than the concentration at which HD-Hook effect occurs; and (6) diluting the sample before detection if the growth rate A from the first-time-read-value to the second-time-read-value with respect to the sample to be detected containing the target antigen (or antibody) is larger than the maximum value of the standard curve.

In some embodiments of the present disclosure, the processor is configured to compare a growth rate A from a first-time-read-value to a second-time-read-value with respect to a sample to be detected containing a target antigen (or antibody) with a critical value. If the growth rate A from the first-time-read-value to the second-time-read-value with respect to the sample to be detected is larger than the critical value, it is determined that a concentration of the sample to be detected is larger than a concentration of a known standard substance.

In some specific embodiments of the present disclosure, a method of using the system comprises steps of:

(1) mixing the sample to be detected containing the target antigen (or antibody) to be detected with light-emitting particles coated with a primary antibody (or antigen), and a secondary antibody (or antigen) labeled with a label to form a mixture, and incubating the mixture to obtain a mixed solution;

(2) performing a first-time-value-reading, which specifically comprises: adding light-sensitive particles labeled with a binding conjugate specific to the label of the secondary antibody (or antigen) into the mixed solution obtained in step (1); incubating the mixed solution; then irradiating the mixed solution and detecting the amount of light emitted by the mixed solution; and reading a value with a photon counter and marking the value as RLU1;

(3) performing a second-time-value-reading, which specifically comprises: incubating the mixed solution after the first-time-value-reading performed in step (2) again; then irradiating the mixed solution and detecting the amount of light emitted by the mixed solution; and reading a value with a photon counter and marking the value as RLU2;

(4) calculating a growth rate A from a signal value obtained at the first-time-value-reading to a signal value obtained at the second-time-value-reading with respect to the sample based on equation A=(RLU2/RLU1−1)×100%;

(5) setting a growth rate A from a first-time-read-value to a second-time-read-value with respect to a known standard substance containing the target antigen (or antibody) as the critical value; and (6) comparing the growth rate A from the first-time-read-value to the second-time-read-value with respect to the sample to be detected containing a target antigen (or antibody) with the critical value, wherein if the growth rate A from the first-time-read-value to the second-time-read-value with respect to the sample to be detected is larger than the critical value, it is determined that the concentration of the sample to be detected is larger than the concentration of the known standard substance.

In some specific embodiments of the present disclosure, the processor is configured to compare a growth rate A from a first-time-read-value to a second-time-read-value with respect to a sample to be detected containing a target antigen (or antibody) with a critical value. If the growth rate A from the first-time-read-value to the second-time-read-value with respect to the sample to be detected is larger than the critical value and the first-time-read-value with respect to the sample to be detected is smaller than a first-time-read-value of a known standard substance, the sample is diluted before detection.

In some specific embodiments of the present disclosure, a method of using the system comprises steps of:

(1) mixing the sample to be detected containing the target antigen (or antibody) to be detected with light-emitting particles coated with a primary antibody (or antigen), and a secondary antibody (or antigen) labeled with a label to form a mixture, and incubating the mixture to obtain a mixed solution;

(2) performing a first-time-value-reading, which specifically comprises: adding light-sensitive particles labeled with a binding conjugate specific to the label of the secondary antibody (or antigen) into the mixed solution obtained in step (1); incubating the mixed solution; then irradiating the mixed solution and detecting the amount of light emitted by the mixed solution; and reading a value with a photon counter and marking the value as RLU1;

(3) performing a second-time-value-reading, which specifically comprises: incubating the mixed solution after the first-time-value-reading performed in step (2) again; then irradiating the mixed solution and detecting the amount of light emitted by the mixed solution; and reading a value with a photon counter and marking the value as RLU2;

(4) calculating a growth rate A from a signal value obtained at the first-time-value-reading to a signal value obtained at the second-time-value-reading with respect to the sample based on equation A=(RLU2/RLU1−1)×100%;

(5) setting a growth rate A from a first-time-read-value to a second-time-read-value with respect to the known standard substance containing the target antigen (or antibody) as the critical value; and (6) comparing the growth rate A from the first-time-read-value to the second-time-read-value with respect to the sample to be detected containing a target antigen (or antibody) with the critical value, wherein if the growth rate A from the first-time-read-value to the second-time-read-value with respect to the sample to be detected is larger than the critical value and the first-time-read-value with respect to the sample to be detected is smaller than the first-time-read-value of the known standard substance, the sample is diluted before detection.

In some embodiments of the present disclosure, the processor is configured to plot a calibration curve and a standard curve based on first-time-read-values with respect to a series of known standard substances containing a target antigen (or antibody) and growth rates A' from the first-time-read-values to second-time-read-values with respect to the series of known standard substances, respectively, and to compare a first-time-read-value with respect to a sample to be detected containing the target antigen (or antibody) to be detected and a growth rate A from the first-time-read-value to a second-time-read-value with respect to the sample to be detected containing the target antigen (or antibody) to be detected with the calibration curve and the standard curve, respectively, so as to determine a concentration of the sample.

In some specific embodiments of the present disclosure, a method of using the system comprises steps of:
(1) mixing the sample to be detected containing the target antigen (or antibody) to be detected with light-emitting particles coated with a primary antibody (or antigen), and a secondary antibody (or antigen) labeled with a label to form a mixture, and incubating the mixture to obtain a mixed solution;
(2) performing a first-time-value-reading, which specifically comprises: adding light-sensitive particles labeled with a binding conjugate specific to the label of the secondary antibody (or antigen) into the mixed solution obtained in step (1); incubating the mixed solution; then irradiating the mixed solution and detecting the amount of light emitted by the mixed solution; and reading a value with a photon counter and marking the value as RLU1;
(3) performing a second-time-value-reading, which specifically comprises: incubating the mixed solution after the first-time-value-reading performed in step (2) again; then irradiating the mixed solution and detecting the amount of light emitted by the mixed solution; and reading a value with a photon counter and marking the value as RLU2;
(4) calculating a growth rate A from a signal value obtained at the first-time-value-reading to a signal value obtained at the second-time-value-reading with respect to the sample based on equation $A=(RLU2/RLU1-1) \times 100\%$;
(5) plotting the standard curve based on the growth rates A' from the first-time-read-values to the second-time-read-values with respect to the series of known standard substances containing the target antigen (or antibody); and
(6) determining, based on the growth rate A, whether a concentration of the sample to be detected is located in a rising section or in a dropping section of the standard curve, and then calculating the concentration of the sample to be detected by putting the RLU1 of the sample to be detected in a corresponding calibration curve thereof.

The calibration curve is a curve plotted based on the first-time-read-values with respect to the series of known standard substances containing the target antigen (or antibody) as well as concentrations of the series of known standard substances.

According to the present disclosure, the light-emitting particles are macromolecules that are filled with a light-emitting compound and a lanthanide, and the light-sensitive particles are macromolecules that are filled with a light-sensitive compound, the light-sensitive particles being capable of generating singlet oxygen ions in response to the irradiation of a red laser beam.

According to the present disclosure, the mixed solution is irradiated with a red laser beam of 600-700 nm, and the amount of light emitted by the mixed solution is detected, wherein a wavelength that is detected of the light emitted is 520-620 nm.

According to the present disclosure, the antigen refers to an immunogenic substance; the antibody refers to an immunoglobulin that is produced by an organism and is capable of recognizing a unique foreign substance; the primary antibody and the secondary antibody each refer to an antibody that is capable of specifically binding to the target antigen; and the primary antigen and the secondary antigen each refer to an antigen that is capable of specifically binding to the target antibody.

The present disclosure, at a seventh aspect, provides a reagent kit comprising: light-emitting particles coated with a primary antibody (or antigen), a secondary antibody (or antigen) labeled with a label, and light-sensitive particles labeled with a binding conjugate specific to the label of the secondary antibody (or antigen). A method of using the reagent kit comprises steps of:
(1) subjecting a sample to be detected containing a target antigen (or antibody) to be detected to a chemiluminescent immunoreactions, initiating chemiluminescence and recording a first-time-read-value and a second-time-read-value with respect to the chemiluminescence, and marking a growth rate from the first-time-read-value to the second-time-read-value as A;
(2) plotting a standard curve based on growth rates A' from first-time-read-values to second-time-read-values with respect to a series of known standard substances containing the target antigen (or antibody), and/or making a standard based on a growth rate A" from a first-time-read-value to a second-time-read-value with respect to a known standard substance containing the target antigen (or antibody); and
(3) comparing the growth rate A from the first-time-read-value to the second-time-read-value with respect to the sample to be detected containing the target antigen (or antibody) to be detected with the standard curve and/or the standard.

In some embodiments of the present disclosure, the growth rate A from the first-time-read-value to the second-time-read-value with respect to the sample to be detected containing the target antigen (or antibody) to be detected is compared with the standard curve.

In some embodiments of the present disclosure, concentrations of the known standard substances are lower than a concentration at which HD-Hook effect occurs, and the known standard substances are used in a positive control.

In some other embodiments of the present disclosure, the method of using the reagent kit further comprises a step of: (4) diluting the sample to be detected before detection if the growth rate A from the first-time-read-value to the second-time-read-value with respect to the sample to be detected containing the target antigen (or antibody) to be detected is larger than a maximum value of the standard curve.

In some specific embodiments of the present disclosure, the method of using the reagent kit comprises steps of:
(a1) mixing the sample to be detected containing the target antigen (or antibody) to be detected with light-emitting particles coated with a primary antibody (or antigen), and a secondary antibody (or antigen) labeled with a label to form a mixture, and incubating the mixture to obtain a mixed solution;
(a2) performing a first-time-value-reading, which specifically comprises: adding light-sensitive particles labeled with a binding conjugate specific to the label of the secondary antibody (or antigen) into the mixed solution obtained in step (a1); incubating the mixed solution; then irradiating the mixed solution and detecting the amount of light emitted by the mixed solution; and reading a value with a photon counter and marking the value as RLU1;

(a3) performing a second-time-value-reading, which specifically comprises: incubating the mixed solution after the first-time-value-reading performed in step (a2) again; then irradiating the mixed solution and detecting the amount of light emitted by the mixed solution; and reading a value with a photon counter and marking the value as RLU2;

(a4) calculating a growth rate A from a signal value obtained at the first-time-value-reading to a signal value obtained at the second-time-value-reading with respect to the sample based on equation $A=(RLU2/RLU1-1)\times 100\%$;

(a5) plotting the standard curve based on the growth rates A' from the first-time-read-values to the second-time-read-values with respect to the series of known standard substances containing the target antigen (or antibody), wherein the concentrations of the standard substances are lower than the concentration at which HD-Hook effect occurs; and (a6) diluting the sample to be detected before detection if the growth rate A from the first-time-read-value to the second-time-read-value with respect to the sample to be detected containing the target antigen (or antibody) to be detected is larger than a maximum value of the standard curve.

In some embodiments of the present disclosure, the growth rate A from the first-time-read-value to the second-time-read-value with respect to the sample to be detected containing the target antigen (or antibody) to be detected is compared with the standard which is marked as a critical value, and/or the known substance is used as a positive control.

In some embodiments of the present disclosure, the method of using the reagent kit further comprises a step of: (4) determining that a concentration of the sample is larger than a concentration of the known standard substance if the growth rate A from the first-time-read-value to the second-time-read-value with respect to the sample to be detected containing the target antigen (or antibody) to be detected is larger than the critical value.

In some specific embodiments of the present disclosure, (c1) mixing the sample to be detected containing the target antigen (or antibody) to be detected with light-emitting particles coated with a primary antibody (or antigen), and a secondary antibody (or antigen) labeled with a label to form a mixture, and incubating the mixture to obtain a mixed solution;

(c2) performing a first-time-value-reading, which specifically comprises: adding light-sensitive particles labeled with a binding conjugate specific to the label of the secondary antibody (or antigen) into the mixed solution obtained in step (c1); incubating the mixed solution; then irradiating the mixed solution and detecting the amount of light emitted by the mixed solution; and reading a value with a photon counter and marking the value as RLU1;

(c3) performing a second-time-value-reading, which specifically comprises: incubating the mixed solution after the first-time-value-reading performed in step (c2) again; then irradiating the mixed solution and detecting the amount of light emitted by the mixed solution; and reading a value with a photon counter and marking the value as RLU2;

(c4) calculating a growth rate A from a signal value obtained at the first-time-value-reading to a signal value obtained at the second-time-value-reading with respect to the sample based on equation $A=(RLU2/RLU1-1)\times 100\%$;

(c5) setting the growth rate A" from the first-time-read-value to the second-time-read-value with respect to the known standard substance containing the target antigen (or antibody) as the critical value; and (c6) comparing the growth rate A from the first-time-read-value to the second-time-read-value with respect to the sample to be detected containing the target antigen (or antibody) to be detected with the critical value, wherein if the growth rate A is larger than the critical value, it is determined that the concentration of the sample to be detected is larger than the concentration of the known standard substance.

In some embodiments of the present disclosure, the method of using the reagent kit further comprises a step of: (4) diluting the sample to be detected before detection if the growth rate A from the first-time-read-value to the second-time-read-value with respect to the sample to be detected containing the target antigen (or antibody) to be detected is larger than the critical value and the first-time-read-value with respect to the sample to be detected is smaller than the first-time-read-value with respect to the known standard substance.

In some specific embodiments of the present disclosure, the method of using the reagent kit further comprises step of:

(d1) mixing the sample to be detected containing the target antigen (or antibody) to be detected with light-emitting particles coated with a primary antibody (or antigen), and a secondary antibody (or antigen) labeled with a label to form a mixture, and incubating the mixture to obtain a mixed solution;

(d2) performing a first-time-value-reading, which specifically comprises: adding light-sensitive particles labeled with a binding conjugate specific to the label of the secondary antibody (or antigen) into the mixed solution obtained in step (d1); incubating the mixed solution; then irradiating the mixed solution and detecting the amount of light emitted by the mixed solution; and reading a value with a photon counter and marking the value as RLU1;

(d3) performing a second-time-value-reading, which specifically comprises: incubating the mixed solution after the first-time-value-reading performed in step (d2) again; then irradiating the mixed solution and detecting the amount of light emitted by the mixed solution; and reading a value with a photon counter and marking the value as RLU2;

(d4) calculating a growth rate A from a signal value obtained at the first-time-value-reading to a signal value obtained at the second-time-value-reading with respect to the sample based on equation $A=(RLU2/RLU1-1)\times 100\%$;

(d5) setting the growth rate A" from the first-time-read-value to the second-time-read-value with respect to the known standard substance containing the target antigen (or antibody) as the critical value; and (d6) comparing the growth rate A from the first-time-read-value to the second-time-read-value with respect to the sample to be detected containing the target antigen (or antibody) to be detected with the critical value, wherein if the growth rate A is larger than the critical value and the first-time-read-value with respect to the sample to be detected is smaller than the firsttime-read-value with respect to the known standard substance, the sample is diluted before being detected again.

In some embodiments of the present disclosure, the method of using the reagent kit further comprises a step of: (4) determining a concentration of the sample by comparing the growth rate A from the first-time-read-value to the second-time-read-value with respect to the sample to be detected containing the target antigen (or antibody) to be detected with the standard curve.

In some specific embodiments of the present disclosure, the method of using the reagent kit further comprises step of:
- (b1) mixing the sample to be detected containing the target antigen (or antibody) to be detected with light-emitting particles coated with a primary antibody (or antigen), and a secondary antibody (or antigen) labeled with a label to form a mixture, and incubating the mixture to obtain a mixed solution;
- (b2) performing a first-time-value-reading, which specifically comprises: adding light-sensitive particles labeled with a binding conjugate specific to the label of the secondary antibody (or antigen) into the mixed solution obtained in step (b1); incubating the mixed solution; then irradiating the mixed solution and detecting the amount of light emitted by the mixed solution; and reading a value with a photon counter and marking the value as RLU1;
- (b3) performing a second-time-value-reading, which specifically comprises: incubating the mixed solution after the first-time-value-reading performed in step (b2) again; then irradiating the mixed solution and detecting the amount of light emitted by the mixed solution; and reading a value with a photon counter and marking the value as RLU2;
- (b4) calculating a growth rate A from a signal value obtained at the first-time-value-reading to a signal value obtained at the second-time-value-reading with respect to the sample based on equation $A=(RLU2/RLU1-1)\times100\%$;
- (b5) plotting a standard curve based on the growth rates A' from the first-time-read-values to the second-time-read-values with respect to the series of known standard substances containing the target antigen (or antibody); and
- (b6) determining, based on the growth rate A, whether the concentration of the sample to be detected is located in a rising section or in a dropping section of the standard curve, and then calculating the concentration of the sample to be detected by putting the RLU1 of the sample to be detected in a corresponding calibration curve thereof.

The calibration curve is a curve plotted based on the first-time-read-values with respect to the series of known standard substances containing the target antigen (or antibody) as well as concentrations of the series of known standard substances.

It shall be particularly noted that the above method are not for diagnosis of diseases, but for expansion of a detection range by two times of value reading, for accurate determining of presence of HD-Hook effect in a sample to be detected, and for easy and rapid calculation of a concentration of an analyte in the sample to be detected during a double-antibody sandwich immunoassay or double-antigen sandwich immunoassay.

Preferably, the antigen refers to an immunogenic substance such as proteins and polypeptides. Typical antigens include (but not limited to): cytokines, tumor makers, metalloproteins, cardiovascular disease and glycuresis related proteins.

The antigen refers to an immunoglobulin that is produced by an organism and is capable of recognizing a unique foreign substance.

In the embodiments of the present disclosure, the antigen or antibody is selected from insulin (INS), epatitis B surface antibody (HBsAb), alpha fetoprotein (AFP), thyroid stimulating hormone (TSH), etc.

Samples that can be detected by the method of the present disclosure are not limited herein. They can be any samples containing a target antigen (or antibody) to be detected. Typical examples of such samples include serum samples, urine samples, saliva samples, etc. Preferred samples used in the present disclosure are serum samples.

Preferably, the primary and secondary antibodies each are an antibody that can specifically bind to the antigen.

For a same antigen, corresponding primary and secondary antibodies can be the same or different, and can bind to the antigen simultaneously.

The primary and secondary antigens each are an antigen that can specifically bind to the target antibody.

For a same antibody, corresponding primary and secondary antigens can be the same or different, and can bind to the antibody simultaneously.

Preferably, the label and the binding conjugate specific to the label of the secondary antibody (or antigen) can specifically bind to each other.

More preferably, the label is biotin, and the binding conjugate specific to the label of the secondary antibody (or antigen) is streptavidin.

Preferably, the light-emitting particles are macromolecules that are filled with a light-emitting compound and a lanthanide compound. The light-emitting compound may be a derivative of dioxene or thioxene, and the lanthanide 1 compound may be Eu(TTA)3/TOPO or Eu (TTA)3/Phen. The light-emitting particles are available on the market. A surface functional group of the light-emitting particles may be any group that can bind to a protein. Examples are known functional groups such as carboxyl group, aldehyde group, amidogen, epoxy ethyl, or halogen alkyl that can bind to a protein.

Preferably, the light-sensitive particles are macromolecules that are filled with a light-sensitive compound. The light-sensitive particles are capable of generating singlet oxygen ions in response to the irradiation of a red laser beam. When the light-sensitive particles are close enough to the light-emitting particles, the singlet oxygen ions travel to the light-emitting particles and react with the light-emitting compound within the light-emitting particles, and then the light-emitting compound emits ultraviolet light. The ultraviolet light then excites the lanthanide compound which then emits photons having a certain wavelength. The light-sensitive compound may be phthalocyanine and is available on the market.

Preferably, the mixed solution is irradiated with a red laser beam of 600-700 nm, and the amount of light emitted by the mixed solution is detected. A wavelength that is detected of the light emitted is 520-620 nm.

Further, when the red laser beam of 600-700 nm irradiates the light-sensitive particles, some of the singlet oxygen ions generated by the light-sensitive particles travel to the light-emitting particles and then the light-emitting particles emit high energy-state light of 520-620 nm.

In a detection range, the concentration of the target antigen to be detected is reflected by the number of the double-antibody sandwich complex and is in direct proportion to the number of the photons. When the concentration of the target antigen to be detected is too high, some of the antigens to be detected bind to a single antibody, as a consequence of which less double-antibody sandwich complexes are formed. This leads to a low light signal which cannot accurately reflect the real concentration of the target antigen to be detected.

Similarly, in the detection range, the concentration of the target antibody to be detected is reflected by the number of the double-antigen sandwich complex and is in direct proportion to the number of the photons. When the concentration of the target antibody to be detected is too high, some of the antibodies to be detected bind to a single antigen, as a consequence of which less double-antigen sandwich complexes are formed. This leads to a low light signal which cannot accurately reflect the real concentration of the target antibody to be detected.

The method of the present disclosure can expand the detection range by performing two times of value reading and then observing a growth rate from a first-time-read-value to a second-time-read-value. A difference between the first-time-read-value and the second-time-read-value is influenced by the following three aspects.

First, during the first-time-value-reading, some of the singlet oxygen ions generated by the light-sensitive particles in response to the irradiation of the red laser beam of 600-700 nm travel to the light-emitting particles and emit, after series of chemical reactions, high energy-level light of 520 nm to 620 nm. Other singlet oxygen ions react with the target antigen (or antibody) to be detected that is not bound by the antibody (or antigen), thereby reducing the concentration of the target antigen (or antibody) to be detected. For a low-concentration sample, after the concentration of the target antigen (or antibody) to be detected is reduced, less double-antibody sandwich complexes are formed, and therefore a signal value obtained at the second-time-value-reading is smaller. For a high-concentration sample, after the concentration of the target antigen (or antibody) to be detected is reduced, more double-antibody sandwich complexes are formed, and therefore a signal value obtained at the second-time-value-reading is larger.

Second, for a low-concentration sample, during the first-time-value-reading, the light-emitting particles generate singlet oxygen ions when irradiated by the red laser beam (600-700 nm) and some energy thereof is consumed. That is why the signal value obtained at the second-time-value-reading is smaller.

Third, for a high-concentration HD-Hook-effect sample, during the first-time-value-reading, the antigen-antibody reaction does not reach equilibrium, and during an interval between the two times of value reading, the reaction keeps proceeding in a forward direction. That is why the signal value obtained at the second-time-value-reading is larger.

To summarize, in the present disclosure, on the one hand, when the reaction does not reach equilibrium, some of the singlet oxygen ions generated by the light-sensitive particles in response to the irradiation of the red laser beam travel to the light-emitting particles, and other singlet oxygen ions react with the target antigen (or antibody) to be detected that is not bound so that part of the target antigen (or antibody) to be detected is consumed. In this way, the equilibrium of the reaction is shifted in a reverse direction. On the other hand, when the light-sensitive particles undergo an irradiation, the energy thereof is consumed, and therefore the signal value with respect to the target antigen (or antibody) to be detected obtained at the second-time-value-reading is smaller. For a high-concentration sample, during the first-time-value-reading, the binding between the double-antibody sandwich complexes and the light-sensitive particles is far from equilibrium, and during the second-time-value-reading, the reaction shifts in the forward direction, and therefore the signal value is larger. As the concentration of the target antigen (or antibody) to be detected increases, the growth rate from the signal value obtained after the second irradiation to the signal value obtained after the first irradiation is also increased. The growth rate of the signal value is in a positive correlation to the concentration of the sample. By observing the growth rate with respect to two signal values, the detection range can be expanded so that the concentration of the sample can be easily calculated during the detection process.

Compared with the existing technologies, the method of present disclosure, based on washing-free property and reaction uniformity of light initiated chemiluminescence platform (light-emitting oxygen channel), realizes detection of signals of a reaction for multiple times without interrupting the immunoreactions. By detecting light signals emitted at two different reaction times and by comparing the values of the two signals, it can be determined whether a sample is an HD-Hook-effect sample. The method is not limited to a detection range, and the detection range is increased effectively by more than 100 times. In the meanwhile, the method of the present disclosure is capable of 100% accurately determining an HD-Hook-effect sample in a double-antibody sandwich assay, and therefore can distinctly improve accuracy of double-antibody sandwich assays and reduce false negatives thereof. In addition, the method of the present disclosure is easy to operate and is able to expand a detection range by two times of value reading and realize easy and rapid calculation of a concentration of an analyte during a detection process.

The present disclosure, at an eighth aspect, provides an immunoassay device. The immunoassay device comprises a reading unit, which is configured to record a chemiluminescent immunoreaction and perform multiple times of value reading with respect to an incubated mixed solution; and a processing unit, which is connected with the reading unit and is configured to determine presence of risk of HD-Hook effect in an immunoassay based on values read by the reading unit.

In some embodiments of the present disclosure, the immunoassay device further comprises a transferring mechanism, which is configured to transfer the incubated mixed solution to the reading unit for value reading.

In some other embodiments of the present disclosure, the immunoassay device further comprises an incubator, which is configured to provide a suitable temperature for the chemiluminescent immunoreaction.

In some embodiments of the present disclosure, the immunoassay device further comprises a returning mechanism, which is configured to return the mixed solution after value reading to the incubator for a second incubation.

In some specific embodiments of the present disclosure, the transferring mechanism is a pushing mechanism and the returning mechanism is a pushback mechanism, and the mixed solution is contained in a plate.

In some other specific embodiments of the present disclosure, the reading unit is configured to record the chemiluminescent immunoreaction and perform two times of value reading with respect to the incubated mixed solution.

In some specific embodiments of the present disclosure, the incubator comprises a first incubator and a second incubator. The pushing mechanism is configured to push the mixed solution incubated in the first incubator to the second incubator for incubation, and is further configured to push the mixed solution incubated in the second incubator to the reading unit for a first-time-value-reading. The pushback mechanism is configured to push the mixed solution after the first-time-value-reading back to the second incubator for a second incubation. The pushing mechanism is further configured to push the mixed solution incubated in the second incubator to the reading unit for a second-time-value-reading. The processing unit detects that a growth rate A from a first-time-read-value to a second-time-read-value is larger than a maximum value of a standard curve, it is determined that HD-Hook-effect risk is present in the immunoassay.

In some other specific embodiments of the present disclosure, the pushback mechanism comprises: a base plate; a guide rail provided on the base plate; a moving-cup mechanism which is provided on the guide rail and is configured to accommodate plates; a drive device configured to drive the moving-cup mechanism to move along the guide rail; photoelectric sensors which are provided on both ends of the base plate and are configured to detect a position of the moving-cup mechanism; and a position adjustment mechanism which is connected with the photoelectric sensor and is configured to adjust the position of the moving-cup mechanism based on a position signal generated by the photoelectric sensor.

In some specific embodiments of the present disclosure, the guide rail is a straight rail or a variable rail.

In some other specific embodiments of the present disclosure, the immunoassay device further comprises: a sample-addition tray which is provided on one side of the incubator and where a sample to be detected and reagents are mixed; and a reagent-refrigerating area which is provided on another side of the incubator and is configured to store reagents.

In some other specific embodiments of the present disclosure, the immunoassay device further comprises a blank plate stacking and loading mechanism which is provided on a side of the sample-addition tray and is configured to push blank plates to the sample-addition tray.

In some specific embodiments of the present disclosure, the immunoassay device further comprises a sample test-tube rack configured to hold sample test-tubes.

In some other specific embodiments of the present disclosure, the immunoassay device further comprises a dilution-plate oscillator which is provided on a side of the sample test-tube rack close to the blank plate stacking and loading mechanism and is configured to oscillate a pre-dilution plate.

In some specific embodiments of the present disclosure, the immunoassay device further comprises a mechanical arm which is provided with a sampling probe. The mechanical arm comprises a first mechanic arm and a second mechanic arm. The first mechanic arm is configured to draw up a sample from the sample test-tube rack and to dispense the sample into a plate in the sample-addition tray. The second mechanic arm is configured to draw up a reagent from the reagent-refrigerating area and to dispense the reagent into a plate in the sample-addition tray.

In some other specific embodiments of the present disclosure, the immunoassay device further comprises a first cleaning mechanism and a second cleaning mechanism. The first cleaning mechanism is configured to clean a sampling probe on the first mechanical arm, and the second cleaning mechanism is configured to clean a sampling probe on the second mechanical arm.

Specifically, before being put into the incubator, the sample undergoes the following steps.

1. Blank plates are transferred by the blank plate stacking and loading mechanism to a position D0 of the sample-addition tray.
2. After the blank plates are transferred to the position D0 of the sample-addition tray, the blank plates are clockwise rotated with the sample-addition tray by 90 degree to a position D1 of the sample-addition tray. At this moment, the first mechanic arm draws up the sample from the sample test-tube rack and dispenses the sample to the blank plates.
3. After dispensing of the sample to the blank plates, the plates having the sample are clockwise rotated with the sample-addition tray by 90 degree to a position D2 of the sample-addition tray. No operation is conducted at this position.
4. The plates having the sample are then clockwise rotated with the sample-addition tray by 90 degree to a position D3 of the sample-addition tray. At this moment, the second mechanic arm draws up the reagent from the reagent-refrigerating area and dispenses the regent to the plates at this position.

After all the plates having the sample at the position D3 are added with the reagent and are transferred to the incubator (not shown in the FIGS.), the sample-addition tray is rotated from the position D3 to the position D0 (this should be conducted after the addition of sample to the blank plates at the position D1 is finished). The sample-addition tray thus finishes one cycle. When the sample-addition tray is operated at a full load, blank plates are loaded at the position D0; the sample is dispensed at the position D1; no operation is done at the position D2; and the reagent is dispensed at the position D3 from which the plates after reagent dispensing are transferred to the incubator 1.

After the plates having the sample and reagent are incubated in the first incubator, the pushing mechanism pushes the plates to the second incubator, during which process light-sensitive particles labeled with a specific binding conjugate specific to the label of the secondary antibody (or antigen) are added to the plate having the sample and reagent to be detected. After that, the plates are incubated in the second incubator and then pushed by the pushing mechanism to the reading unit to undergo irradiation by a laser beam. The amount of light emitted is detected and a first-time-read-value is recorded. After the first-time-value-reading, the plates are pushed back by the pushback mechanism to the second incubator for a second incubation. After the second incubation, the plates are again pushed by the pushing mechanism to the reading unit to undergo irradiation by a laser beam. The amount of light emitted is detected and a second-time-read-value is recorded. After the two times of value reading are finished, the processing unit processes the first-time-read-value and the second-time-read-value. When a growth rate from the first-time-read-value to the second-time-read-value is larger than a maximum value of the standard curve, it is determined that HD-Hook effect is present in the immunoassay. One approach is to let the device give a qualitative reminder of HD-Hook effect, and an operator then dilutes the sample before detecting the sample. Another approach is to let the device give a quantitative result, but the result is much higher than the linear range.

Compared with existing technologies, the present disclosure has the following beneficial advantages. The device provided by the present disclosure determines the presence of HD-Hook effect risk in an immunoassay by using the reading unit to conduct two or even more times of value readings with respect to the incubated mixed solution and by using the processing unit to process the values read by the reading unit. This helps to avoid the situation in which due to HD-Hook effect, one cannot tell whether a concentration of a sample to be detected has exceeded the linear range of an assay kit or the concentration of the sample is really the detected value. Inaccurate detection results are thus avoided.

BRIEF DESCRIPTION OF THE DRAWINGS

The present disclosure will be illustrated below in a more detailed way with reference to the drawings, in which.

In the accompanying drawings, same components are designated by same reference numerals. The drawings are not drawn to actual scale.

DETAILED DESCRIPTION OF THE EMBODIMENTS

Figure 1:
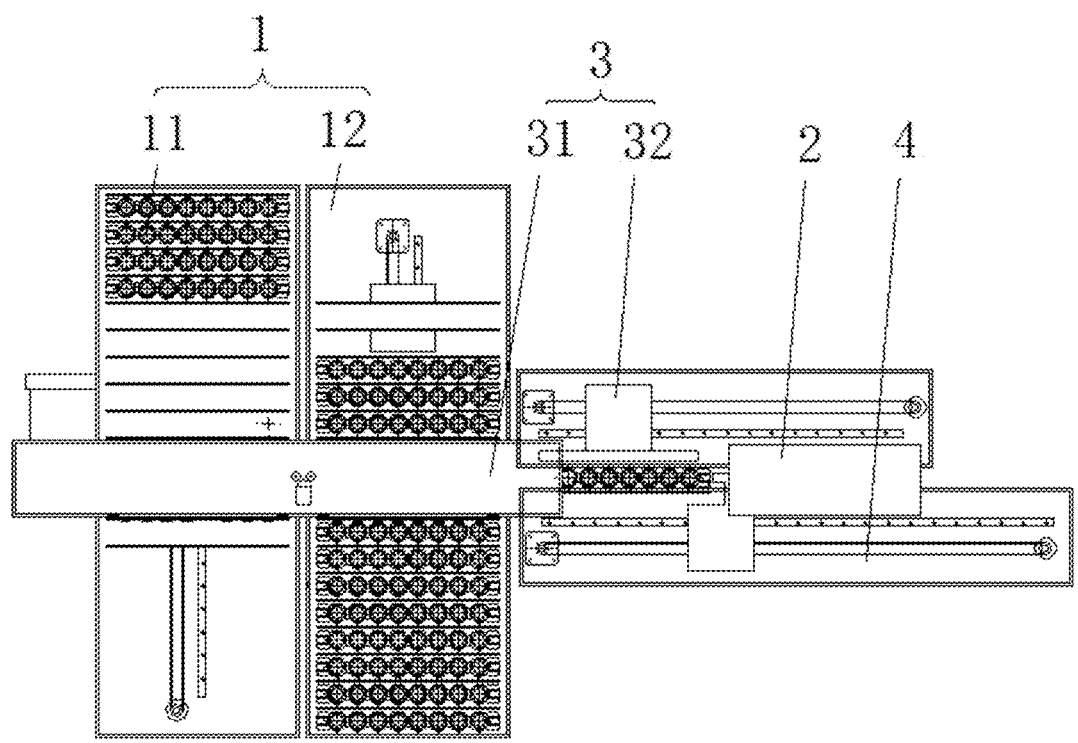
FIG. 1 schematically shows a structure inside a casing of a device for determining HD-Hook-effect sample and for immunoassay provided by the present disclosure.

It shall be appreciated that the protection scope of the present disclosure is not limited to the following specific embodiments, and that the terms used herein in the embodiments are for description of the specific embodiments, rather than limiting the protection scope of the present disclosure.

When a numerical value scope is provided in an embodiment, it shall be appreciated that, unless otherwise noted, one can select and use any of numerical values within the scope, including the two values at two ends of the scope and the values between the two ends of the scope. Unless otherwise noted, the techniques and scientific terms used herein have same meanings as those understood by one skilled in the art. In addition to the specific methods, devices, and materials adopted in the specific embodiments, one may also employ any other methods, devices, and materials in the existing techniques that are similar to or equivalent to those adopted in the embodiments of the present disclosure to implement the present disclosure according to one skilled in the art's knowledge of the existing techniques and the recitation of the present disclosure.

Unless otherwise noted, the experiment method, assay method, and preparation method all adopt commonly used techniques in the art, for example, commonly used techniques of molecular biology, biochemistry, chromatin structure and analysis, analytic chemistry, cell culturing, recombinant DNA technology, and other common techniques used in related fields. These techniques have been detailed in existing literature. Reference can be made to: Sambrook et al, MOLECULAR CLONING: A LABORATORY MANUAL, Second edition, Cold Spring Harbor Laboratory Press, 1989 and Third edition, 2001; Ausubel et al, CURRENT PROTOCOLS IN MOLECULAR BIOLOGY, John Wiley & Sons, New York, 1987 and periodic updates; the series METHODS IN ENZYMOLOGY, Academic Press, San Diego; Wolfe, CHROMATIN STRUCTURE AND FUNCTION, Third edition, Academic Press, San Diego, 1998; METHODS IN ENZYMOLOGY, Vol. 304, Chromatin (P. M. Wassarman and A. P. Wolfe, eds.), Academic Press, San Diego, 1999; METHODS IN MOLECULAR BIOLOGY, Vol. 119, Chromatin Protocols (P. B. Becker, ed.), Humana Press, Totowa, 1999, etc.

The inventor of the present disclosure found through wide and in-depth researches that whether a sample needs to be diluted or not before an assay can be determined by: performing two times of value reading without interrupting the reaction and then comparing a growth rate A from the first-time-read-value to the second-time-read-value with a critical value; or establishing interrelationship between the growth rate A and a concentration of the sample and expanding a detection range by way of the two values, so that the concentration of the sample can be easily calculated during the detection process; or analyzing a relationship between the growth rate A and a fact whether the sample is an HD-Hook-effect sample, so that a false negative caused by HD-Hook effect in a double-antibody sandwich immunoassay can be excluded easily and effectively, thus improving accuracy of double-antibody sandwich immunoassay. The inventor of the present disclosure further provides an assay device, which can achieve two or more times of value reading of the incubated mixed solution. The device can be used to implement the aforementioned method for determining an HD-Hook-effect sample and the immunoassay method.

Figure 2:
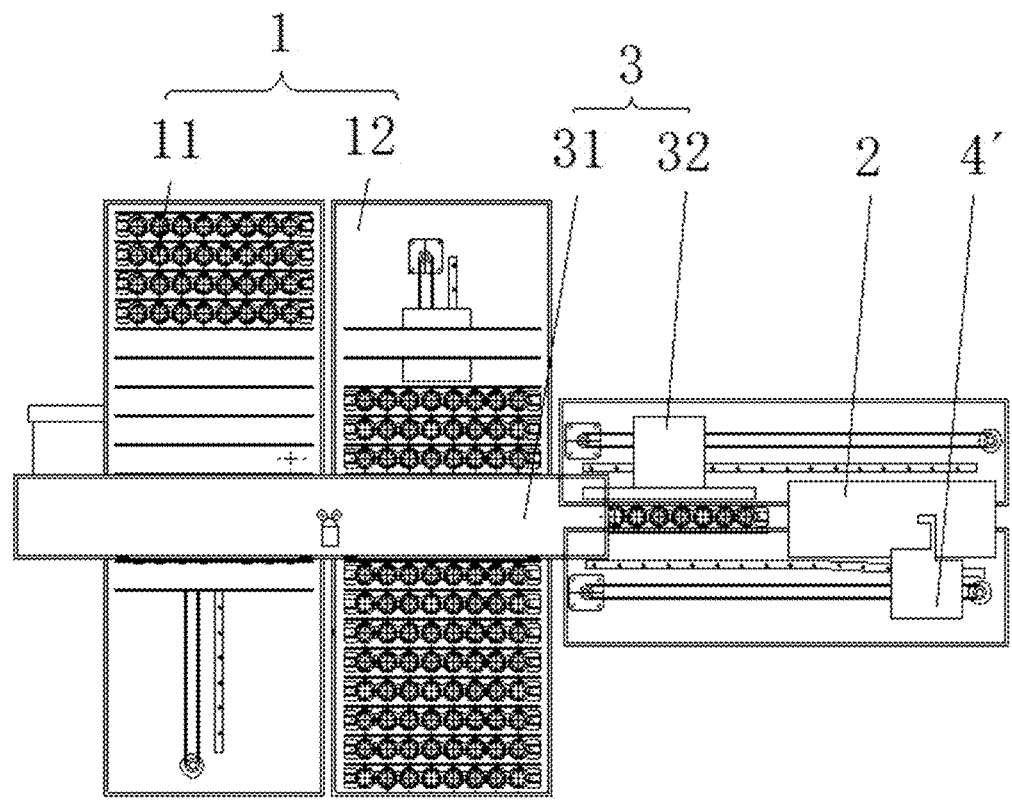
FIG. 2 schematically shows another structure inside the casing of the device for determining HD-Hook-effect sample and for immunoassay provided by the present disclosure.

FIGS. 1 and 2 schematically show structure inside a casing of a device for determining HD-Hook-effect sample and for immunoassay.

The device comprises an incubator 1 which is configured to provide a suitable temperature for a chemiluminescent immunoreaction. The incubator 1 includes a first incubator 11 and a second incubator 12.

The device further comprises a reading unit 2 which is configured to record the chemiluminescent immunoreaction and to read values of an incubated mixed solution twice. The reading unit 2 may be a photomultiplier or a laser exciter.

The device further comprises a pushing mechanism 3 which is arranged between the incubator 1 and the reading unit 2. The pushing mechanism includes a first pushing mechanism 31 and a second pushing mechanism 32. The first pushing mechanism 31 horizontally runs through the incubator 1. The second pushing mechanism 32 is connected to an end of the first pushing mechanism 31 and is located inside a casing of the device.

The first pushing mechanism 31 and the second pushing mechanism 32 are configured to work together to push a plate incubated in the first incubator 11 to the reading unit 2 for a first-time-value-reading, and to push a plate incubated in the second incubator 12 to the reading unit 2 for a second-time-value-reading.

The plate contains a mixture solution containing: a sample to be detected that contains a target antigen (or antibody) to be detected; light-emitting particles coated with a primary antibody (or antigen); and a second antibody (or antigen) labeled with a label. The mixture solution further contains light-sensitive particles labeled with a specific binding conjugate specific to the label of the secondary antibody (or antigen).

Figure 3:
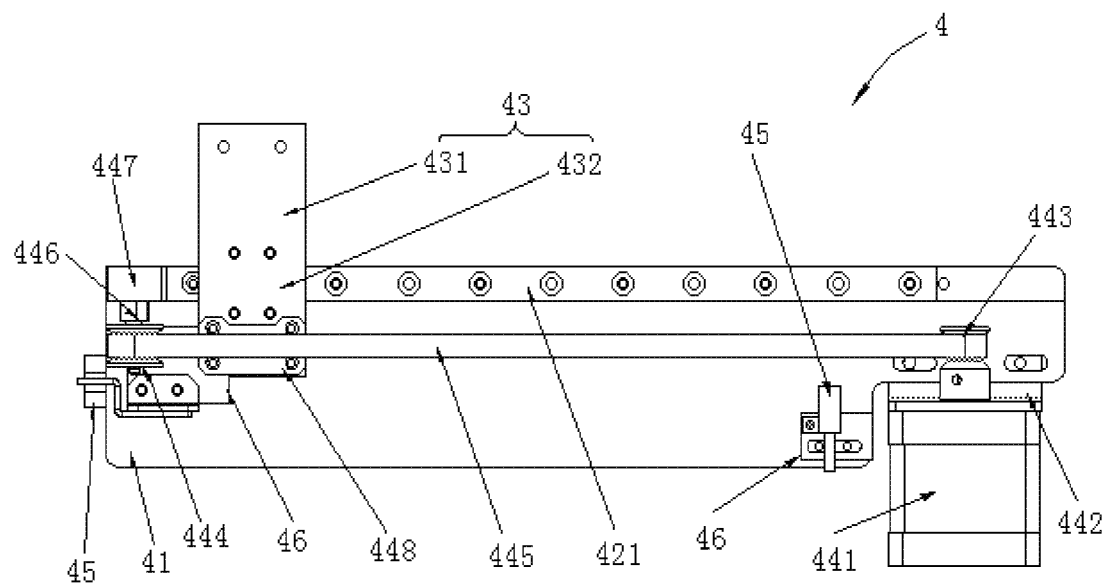
FIG. 3 schematically shows a structure of a pushback mechanism of the device for determining HD-Hook-effect sample and for immunoassay provided by the present disclosure.
Figure 4:
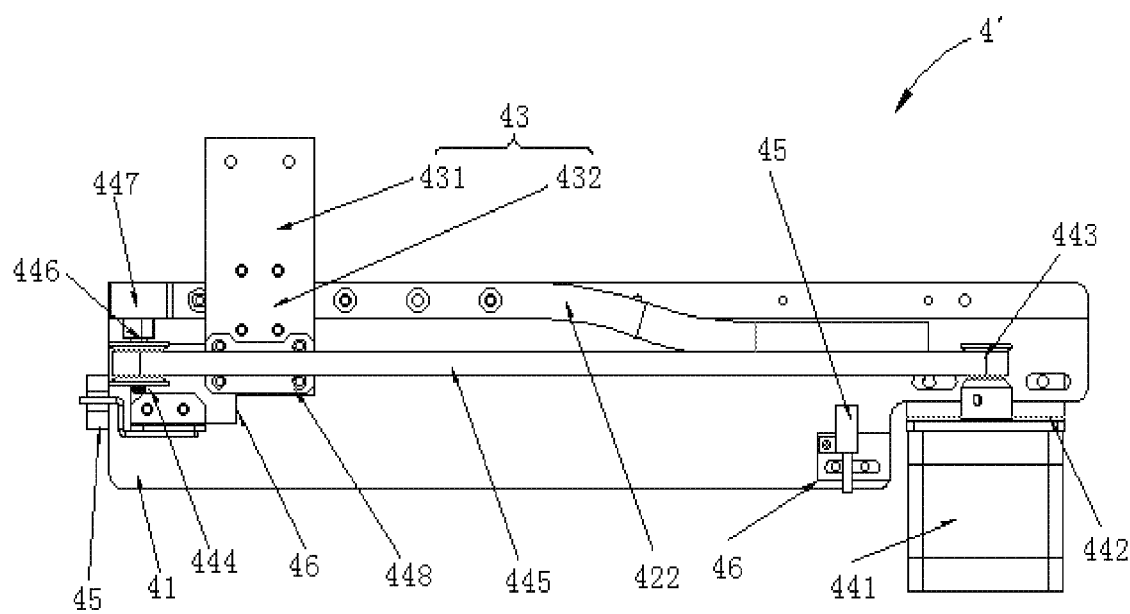
FIG. 4 schematically shows another structure of the pushback mechanism of the device for determining HD-Hook-effect sample and for immunoassay provided by the present disclosure.

The device further comprises a pushback mechanism which is arranged between the reading unit 2 and the second incubator 12. The pushback mechanism is a straight-rail pushback mechanism 4 as shown in FIG. 3 or a variable-rail pushback mechanism 4' as shown in FIG. 4. Both types of pushback mechanisms can be used to push the plate after the first reading back to the second incubator 12 for a second incubation.

When the first reading is carried on, the incubated plate is irradiated with a laser beam and the amount of light emitted is detected. When the second reading is carried on, the plate incubated again is irradiated with a laser beam and the amount of light emitted is detected.

The device further comprises a processing unit (not shown in the FIGS.). When a growth rate from a first-time-read-value to a second-time-read-value is larger than a maximum value of a standard curve, the plate is diluted before it is detected. The standard curve is plotted according to a growth rate from a first-time-read-value to a second-time-read-value with respect to a series of known standard substances containing the target antigen or antibody to be detected. The standard substances each have a concentration lower than a concentration thereof which can cause HOOK effect. The processing unit may be a computer that processes the values read and draws curves.

It shall be appreciated that the design that the incubator comprises the first incubator and the second incubator is made to facilitate the mechanical implementation of the immunoassay device, and the present disclosure is not limited thereto.

It shall also be appreciated that the pushing mechanism may be a mechanical grasping arm and that the pushback mechanism may also be a mechanical grasping arm, and the present disclosure is not limited thereto.

In some specific embodiments of the present disclosure, the pushback mechanism comprises a base plate 41 and a guide rail provided on the base plate 41. The guide rail is a straight rail 421 as shown in FIG. 3. The guide rail may also be a variable rail 422 as shown in FIG. 4.

The pushback mechanism further comprises a drive device which is configured to drive a moving-cup mechanism 43 to move along the guide rail. Specifically, the drive device comprises a stepping motor 441 which is fixed on an end of the guide rail 421/422 via a motor securing plate 442. The stepping motor 441 is provided on an output end thereof with a synchronous pulley 443. The other end of the guide rail 421/422 is provided with an idle pulley 444. The synchronous pulley 443 and the idle pulley 444 are sleeved by a synchronous belt 445. The idle pulley 444 is provided with an idle pulley axle 446 which runs through an axis of the idle pulley 444. The idle pulley axle 446 is fixed on an idle pulley plate 447.

The pushback mechanism further comprises a moving-cup mechanism 43 which is provided on the guide rail. The moving-cup mechanism 43 is used to accommodate plates. The moving-cup mechanism 43 comprises a moving-cup drag chain plate 431 and a moving-cup connection plate 432 which is connected with the moving-cup drag chain plate 431. The moving-cup connection plate 432 is connected with the synchronous belt 445 through a synchronous belt press plate 448.

The pushback mechanism further comprises photoelectric sensors 45 provided on both ends of the base plate 41. The photoelectric sensors 45 are connected with a sensor blocking plate 46 by means of which the photoelectric sensors 45 detect a position of the moving-cup mechanism 43.

The pushback mechanism further comprises a position adjustment mechanism connected with the photoelectric sensors 45. The position adjustment mechanism is able to adjust the position of the moving-cup mechanism 43 based on a position signal generated by the photoelectric sensor 45. Specifically, the position adjustment mechanism comprises a position adjustment plate 46 and a controller (not shown in the FIGS.). The controller is connected with the position adjustment plate 46 and the photoelectric sensors 45, respectively. The controller, based on the position signal received from the photoelectric sensors 45, controls the position adjustment plate 46 to adjust the position of the moving-cup mechanism 43. In general, the position adjustment mechanism is used for slight adjustment. That is to say, it is used to conduct slight adjustment when the moving-cup mechanism 43 fails to reach a predetermined position or slightly deviates from the predetermined position.

Figure 5:
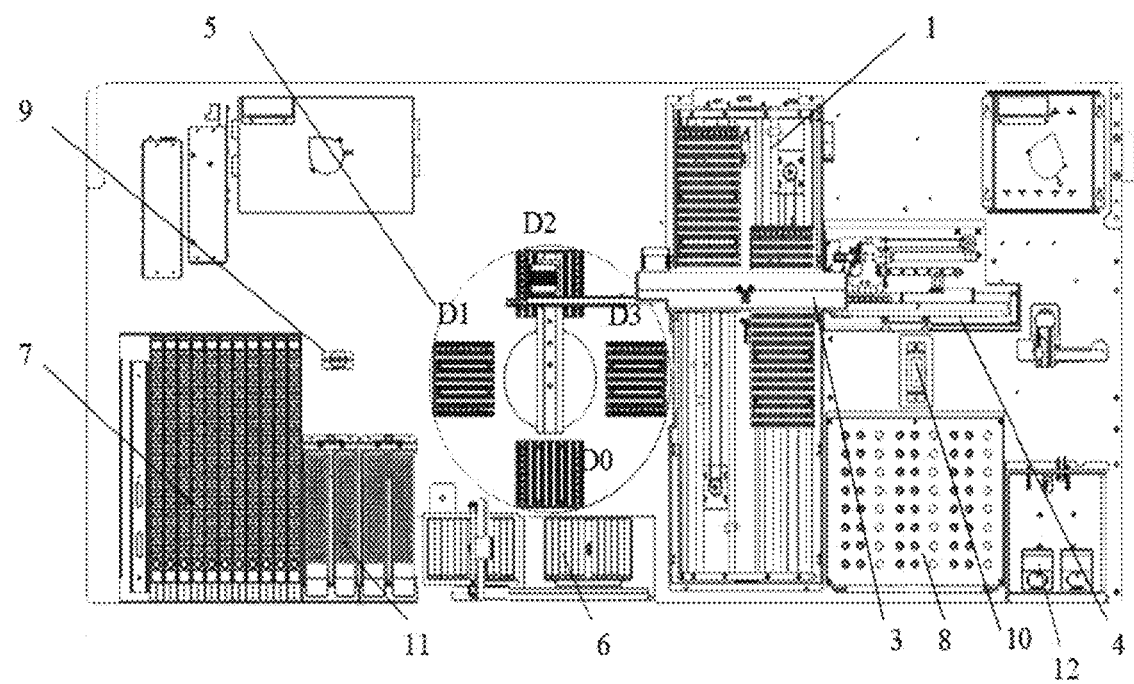
FIG. 5 schematically shows a structure of the device for determining HD-Hook-effect sample and for immunoassay provided by the present disclosure.

In some other specific embodiments of the present disclosure, as shown in FIG. 5, the device further comprises a rotatable sample-addition tray 5 which is provided on one side of the incubator 1 and where a sample to be detected and a reagent are mixed in a blank plate. The sample contains a target antigen (or antibody) to be detected, and the reagent is light-emitting particles coated with a primary antibody (or antigen) and a second antibody (or antigen) labeled with a label.

In some specific embodiments of the present disclosure, the device further comprises a reagent-refrigerating area 8 provided on another side of the incubator 1, for storage of the reagent.

In some other specific embodiments of the present disclosure, the device further comprises a blank plate stacking and loading mechanism 6 provided on a side of the sample-addition tray 5, for transferring blank plates to the sample-addition tray 5.

In some specific embodiments of the present disclosure, the device further comprises a sample test-tube rack for holding sample test-tubes.

In some other specific embodiments of the present disclosure, the device further comprises a mechanic arm (not shown in the FIGS.) which is provided with a sampling probe.

The mechanic arm includes a first mechanic arm and a second mechanic arm. The first mechanic arm is used to take a sample from the sample test-tube rack, and the second mechanic arm is used to take a reagent from the reagent-refrigerating area.

In some specific embodiments of the present disclosure, the device further comprises a first cleaning mechanism 9 and a second cleaning mechanism 10. The first cleaning mechanism 9 is used to clean a sampling probe on the first mechanical arm, and the second cleaning mechanism 10 is used to clean a sampling probe on the second mechanical arm.

Figure 6:
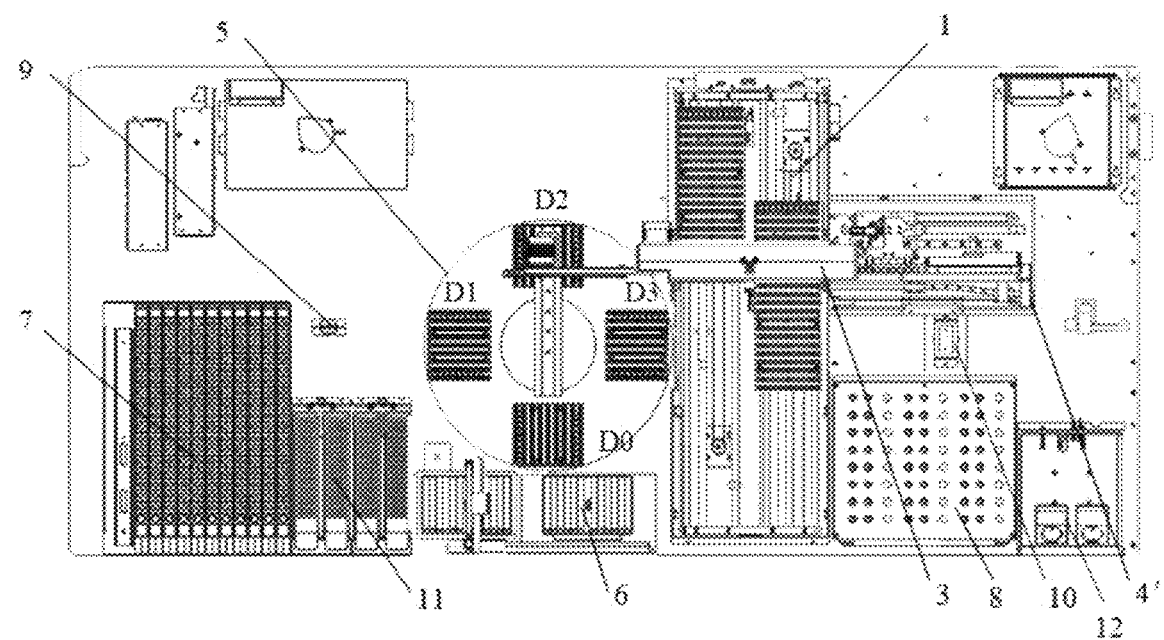
FIG. 6 schematically shows another structure of the device for determining HD-Hook-effect sample and for immunoassay provided by the present disclosure.

If the straight guide rail 421 is adopted, the module is increased in length, which enables the casing (namely the entire construction shown in FIGS. 1 and 2) and a pump 11 to be arranged closely to each other (as shown in FIG. 5), thereby rendering the mounting and dismounting of the device complex. If the variable guide rail 422 is adopted (as one implementing method, the variable guide rail 422 can be designed as a curved guide rail), the module is increased in width, which enables the casing and the second cleaning mechanism 10 to be arranged closely to each other (as shown in FIG. 6), but does not affect the mounting and dismounting of the device.

Specifically, before being put into the incubator 1, the sample undergoes the following steps.

1. Blank plates are transferred by the blank plate stacking and loading mechanism 6 to a position D0 of the sample-addition tray 5.

2. After the blank plates are transferred to the position D0 of the sample-addition tray 5, the blank plates are clockwise rotated with the sample-addition tray 5 by 90 degree to a position D1 of the sample-addition tray 5. At this moment, the first mechanic arm draws up the sample from the sample test-tube rack 7 and dispenses the sample to the blank plates.

3. After dispensing of the sample to the blank plates, the plates having the sample are clockwise rotated with the sample-addition tray 5 by 90 degree to a position D2 of the sample-addition tray 5. No operation is conducted at this position.

4. The plates having the sample are then clockwise rotated with the sample-addition tray 5 by 90 degree to a position D3 of the sample-addition tray 5. At this moment, the second mechanic arm draws up the reagent from the reagent-refrigerating area 8 and dispenses the regent to the plates at this position.

After all the plates having the sample at the position D3 are added with the reagent and are transferred to the incubator 1, the sample-addition tray 5 is rotated from the position D3 to the position D0 (this should be conducted after the addition of sample to the blank plates at the position D1 is finished). The sample-addition tray 5 thus finishes one cycle. When the sample-addition tray 5 is operated at a full load, blank plates are loaded at the position D0; the sample is dispensed at the position D1; no operation is done at the position D2; and the reagent is dispensed at the position D3 from which the plates after reagent dispensing are transferred to the incubator 1. The rotation of the sample-addition tray 5 is performed after operations at positions D0-D3 are all finished.

After the plates having the sample and reagent are incubated in the first incubator 11, the pushing mechanism 3 pushes the plates to the second incubator, during which process light-sensitive particles labeled with a specific binding conjugate specific to the label of the secondary antibody (or antigen) are added. After that, the plates are incubated in the second incubator and then pushed by the pushing mechanism 3 to the reading unit 2 to undergo irradiation by a laser beam. The amount of light emitted is detected and a firsttime-read-value is recorded. After the first-time-value-reading, the plates are pushed back by the straight-rail pushback mechanism 4 or the variable-rail pushback mechanism 4' to the second incubator for a second incubation. After the second incubation, the plates are again pushed by the pushing mechanism 3 to the reading unit 2 to undergo irradiation by a laser beam. The amount of light emitted is detected and a second-time-read-value is recorded.

Figure 7:
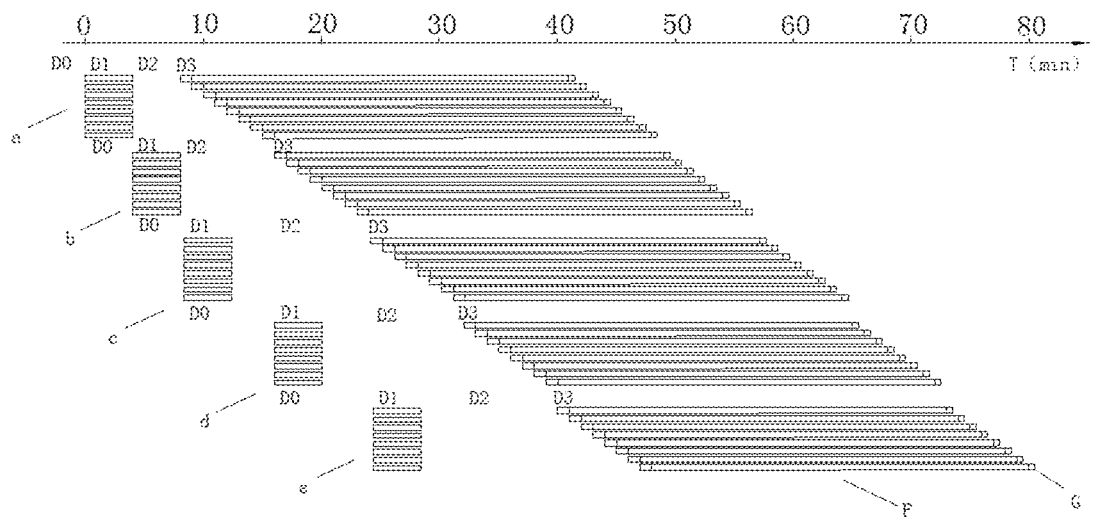
FIG. 7 shows a time sequence of complete detection process of the device for determining HD-Hook-effect sample and for immunoassay provided by the present disclosure.

After the two times of value reading are finished, the processing unit processes the first-time-read-value and the second-time-read-value. When a growth rate from the first-time-read-value to the second-time-read-value is larger than a maximum value of the standard curve and when the first-time-read-value with respect to the sample to be detected is smaller than a value with respect to the known standard substance, there are two approaches to deal with this situation. One approach is to let the device give a qualitative reminder of HOOK effect, and an operator then dilutes the sample before detecting the sample. Another approach is to let the device give a quantitative result, but the result is much higher than the linear range. FIG. 7 shows a complete time sequence of the assay process which does not involve a dilution step. In FIG. 7, a, b, c, d, and e represent a first batch of plates, a second batch of plates, a third batch of plates, a fourth batch of plates, and a fifth batch of plates, respectively.

1) Supposing 8 blank plates are pushed into the sample-addition tray 5 each time from the blank plate stacking and loading mechanism 6, this process takes about 20 seconds which is neglected in FIG. 7.

2) Time used to rotate the sample-addition tray 5 is also neglected.

3) When the blank plates are rotated to the position D1, the sample is dispensed to the plates at the position D1. As shown the position D1 in FIG. 7, supposing the sample drawn up each time is dispensed to 8 plates, and each operation to dispense the sample into one plate takes 30 seconds, then to dispense the sample into the 8 plates takes totally 240 seconds.

4) The reagent is dispensed to the plates at the position D3. As shown in the position D3 in FIG. 7, supposing the reagent drawn up each time is dispensed to 8 plates, and dispensing of an reagent R1 is followed immediately by dispensing of an reagent R2, and supposing each operation to dispensing the reagent to one plate takes 30 seconds, then to dispense the two reagents into the 8 plates takes totally 480 seconds.

5) Time used to transfer the plates from the position D3 to the first incubator 11 is neglected, and this step can be performed when the second mechanical arm cleans the sampling probe.

6) In FIG. 7, F represents a time period of the first incubation.

7) In FIG. 7, time used for dispensing the light-sensitive particles to each of the plates is neglected. A general-purpose-liquid adding area 12 is shown in FIGS. 5 and 6.

8) In FIG. 7, F represents a time period of the second incubation.

9) In FIG. 7, G represents a time period during which the reading unit reads one plate (including time used to move and discard the plate by the mechanical arm).

During the above process, two reagents are dispensed in the reagent dispensing procedure. It should be appreciated that three reagents R1, R2, R3 can be dispensed. Supposing R1, R2, R3 are all added after dispensing of the sample, for example, if the antibody to be detected is HBeAb, R3 can be 50 μl of a neutralizing e antigen, operations are similar to the situation where there are only R1 and R2. The only difference is that one more reagent is added. The sequence of dispensing R1, R2, and R3 is arbitrary.

It should also be appreciated that one of the reagents R1, R2, and R3 can be added before dispensing of the sample. For example, if the antibody to be detected is CA19-9, R3 is 15 μl of sample dilution solution. At the position D1, the reagent is dispensed by the second mechanical arm and then the sample is dispensed by the first mechanical arm. Other operations are the same as the situation where there are only R1 and R2.

It should also be appreciated that among R1, R2, and R3, R3 is a dilution solution, and a pre-dilution plate is needed. For example, if the antibody to be detected is HCV, 10 μl of sample is mixed with 100 μl of dilution solution to form a diluted sample. Then 25 μl of the diluted sample is taken to be used in the assay. After the blank plates are rotated to the position D1, the second mechanical arm dispenses the dilution solution R3 to the pre-dilution plate, and then the first mechanical arm dispenses the sample to the pre-dilution plate. If necessary, repeated pipetting up and down can be done. During the process of dispensing the dilution solution, the dilution solution drawn up each time can be dispensed into multiple plates, for example, into five plates. The solution dispensed into one of the five plates requires pre-dilution, and the solution dispensed into four other plates do not require pre-dilution. Thus, the first mechanical arm draws up the sample and dispenses one part of the sample into the pre-dilution plate, and dispenses four other parts into four blank plates respectively. After that, the pre-dilution plate is oscillated. Referring to FIGS. 5 and 6, a dilution-plate oscillator 11 for oscillating the pre-dilution plate is provided on a side of the sample test-tube rack 7 close to the blank plate stacking and loading mechanism 6. After the pre-dilution plate oscillated, the first mechanical arm dispenses the diluted sample to the plate. Operations to be followed are the same as the situation where there are only R1 and R2, and therefore will not be described herein in detail.

As used herein in the present disclosure, the terms "primary antibody" and "secondary antibody" each refer to an antibody that can specifically bind a certain antigen (e.g., a tumor marker). For a same antigen (e.g., a tumor marker), corresponding primary and secondary antibodies thereof can be different or the same and can simultaneously bind the antigen. The terms "primary antigen" and "secondary antigen" each refer to an antigen that can specifically bind a certain antibody (e.g., a Hepatitis B surface antibody). For a same antibody (e.g., a Hepatitis B surface antibody), corresponding primary and secondary antigens thereof can be different or the same and can simultaneously bind the antibody.

As used herein in the present disclosure, the term "antigen" refers to an immunogenic substance such as proteins and polypeptides. Typical antigens include (but not limited to): cytokines, tumor makers, metalloproteins, cardiovascular disease and glycuresis related proteins.

As used herein in the present disclosure, the term "tumor marker" refers to a substance that is produced directly by a tumor or by other cells of the body in response to the tumor during the development or proliferation of the tumor. It is indicative of the presence and growth of the tumor. Typical tumor markers in the art include (but not limited to): alpha fetoprotein (AFP), cancer antigen 125 (CA125), etc.

Basic principles of double-antibody sandwich assay:

Basic principles of double-antibody sandwich assay are well-known to those skilled in the art. A conventional process of a double-antibody sandwich assay is as follows. A primary antibody is bound to a solid-phase carrier. The primary antibody is enabled to react first with an antigen and then with a labeled second antibody. A signal is finally detected by way of chemiluminescent reaction or enzyme-linked immune sorbent assay.

Basic principles of light initiated chemiluminescence:

Basic principles of light initiated chemiluminescence are well-known to those skilled in the art, and a conventional process thereof is as follows. In a light initiated chemiluminescent assay, light-sensitive particles and light-emitting particles bind to each other within certain range, which enables the transferring of ionized oxygen energy to the light-emitting dye to emit light, thus to detect the immuno-interaction or an analyte responsible for the immuno-interaction in a sample. The light-sensitive particles are filled with a light-sensitive compound, and the light-emitting particles are filled with a light-emitting compound and a lanthanide complex. The light-sensitive particles release high energy-state singlet oxygen ions (4 μS) after being activated with red laser beam with specific wavelength (600-700 nm). A travelling distance of the ions is about 200 nm. When the light-sensitive particles and the light-emitting particles are close enough to each other, the singlet oxygen ions released by the light-sensitive particles are capable of reaching the light-emitting particles and emitting, after series of chemical reactions, high energy-level light of 520 nm to 620 nm, which is then detected by a device.

In a preferred embodiment of the present disclosure, the feature that a primary antibody is bound to light-emitting particles is utilized, and a biotin-labeled secondary antibody and streptavidin-labeled light-sensitive particles are used. A serum sample or an antigen standard quality control solution, the light-emitting particles coated with the primary antibody, and the biotin-labeled secondary antibody are added successively or simultaneously into a reactor, followed by addition of the streptavidin-labeled light-sensitive particles, so as to cause the following reactions.

(1) The primary antibody on the light-emitting particles binds a corresponding antigen from the serum sample or from the antigen standard quality control solution to form a ternary complex of "antigen-primary antibody-light-emitting particle".

(2) The secondary antibody binds a corresponding antigen from the serum sample or from the antigen standard quality control solution to form a double-antibody sandwich complex of "secondary antibody-antigen-primary antibody-light-emitting particle".

The biotin and the streptavidin bind to each other specifically, leading to binding of the double-antibody sandwich complex and the light-sensitive particles.

At this moment, a distance between the light-sensitive particles and the light-emitting particles is smaller than 200 nm. When irradiated by a red laser beam (600-700 nm), the light-sensitive particles release singlet oxygen ions which are received by the light-emitting particles. After a series of chemical reactions, high energy-level light of 520 nm to 620 nm is emitted by the light-emitting particles, and the sample is then qualitatively or quantitatively assayed according to intensity of the emitted light.

In another preferred embodiment of the present disclosure, the feature that a primary antigen is bound to light-emitting particles is utilized, and a biotin-labeled secondary antigen and streptavidin-labeled light-sensitive particles are used. A serum sample or an antigen standard quality control solution, the light-emitting particles coated with the primary antigen, and the biotin-labeled secondary antigen are added successively or simultaneously into a reactor, followed by addition of the streptavidin-labeled light-sensitive particles, so as to cause the following reactions.

(1) The primary antigen on the light-emitting particles binds a corresponding antibody from the serum sample or from the antigen standard quality control solution to form a ternary complex of "antibody-primary antigen-light-emitting particle".

(2) The secondary antigen binds a corresponding antibody from the serum sample or from the antigen standard quality control solution to form a double-antigen sandwich complex of "secondary antigen-antibody-primary antigen-light-emitting particle".

The biotin and the streptavidin bind to each other specifically, leading to binding of the double-antigen sandwich complex and the light-sensitive particles.

At this moment, a distance between the light-sensitive particles and the light-emitting particles is smaller than 200 nm. When irradiated by a red laser beam (600-700 nm), the light-sensitive particles release singlet oxygen ions which are received by the light-emitting particles. After a series of chemical reactions, high energy-level light of 520 nm to 620 nm is emitted by the light-emitting particles, and the sample is then qualitatively or quantitatively assayed according to intensity of the emitted light.

Operating details of the present disclosure will be described further below.

(1) The light-emitting particles coated with the primary antibody (or antigen) are referred to as a reagent 1, which can be purchased from Beyond Biotech Co., Ltd.

(2) The secondary antibody (antigen) can be labeled with a known label in the art or a conjugate system thereof. Preferably, the secondary antibody (antigen) is labeled with a biotin-avidin system. The biotin-labeled secondary antibody (or antigen) is referred to as a reagent 2, which can be purchased from Beyond Biotech Co., Ltd.

(3) The light-sensitive particles coated with the streptavidin are referred to as a general-purpose solution, which can be purchased from Beyond Biotech Co., Ltd.

(4) Calibrator:

A solution of a known standard substance having a concentration within a certain range (a concentration of a peak-value calibrator equaled to an HD-Hook-effect concentration) was prepared using an antigen (or antibody) to be detected. The calibrator, the reagent 1, and the reagent 2 were mixed and incubated, followed by addition of LicA general-purpose solution. After the obtained mixture was incubated for a period of time, a first-time-read-value (RLU1) was acquired. The mixture was incubated again for a period of time, and then a second-time-read-value (RLU2) was obtained. A growth rate A from the first-time-read-value to the second-time-read-value was calculated based on equation $A=(RLU2/RLU1-1)\times 100\%$. A calibration curve and a standard curve were plotted respectively based on RLU1 of the calibrator and a concentration of the calibrator and based on the growth rate A and the concentration of the calibrator. The calibration curve of the RLU1 and the concentration of the calibrator showed that during a non-HD-Hook-effect period, the RLU1 increased with the increase of the concentration, and this period was marked as a rising period of the RLU1; and when the concentration increased to a level when HD-Hook effect occurs, the RLU1 started to decrease with the increase of the concentration, and this period was marked as a dropping period of the RLU1. The standard curve of the growth rate A and the concentration showed that the growth rate increased with the increase of the concentration, and was not affected by the HD-Hook effect.

The concentration range of the solution of the known standard substance may, if required, span the HD-Hook-effect concentration or be lower than the HD-Hook-effect concentration.

(5) Detection of sample:

Samples that can be detected by the method of the present disclosure are not specifically limited, and can be any samples containing an antigen (or antibody). Typical examples of these samples may include: serum samples, urine sample, saliva samples, etc. Preferred samples are serum samples.

(6) Calculation of sample concentration:

A growth rate A from a first-time-read-value to a second-time-read-value with respect to the sample to be detected is compared with the growth rate A with respect to the calibrator. If the growth rate A with respect to the sample to be detected is larger than the growth rate A with respect to the calibrator, it indicates that the concentration of the sample is larger than the concentration of the calibrator, and if at the same time RLU1 of the sample is smaller than the RLU1 of the calibrator, it indicates that the low RLU1 of the sample is caused by the HD-Hook effect, and that the sample has to be diluted before being detected.

Alternatively, the growth rate A from the first-time-read-value to the second-time-read-value with respect to the sample to be detected is put into the standard curve of the growth rate A and the concentration of the calibrator, and then it is determined whether the concentration of the sample to be detected is located in the rising section of the RLU1 or in the dropping section of the RLU1. After that, the RLU1 of the sample to be detected is put into the determined section of the calibration curve of the RLU1 of the calibrator and the concentration of the calibrator to calculate the concentration of the sample to be detected.

Optionally, the growth rate A from the first-time-read-value to the second-time-read-value with respect to the sample to be detected is compared with a critical value R0 of the HD-Hook effect. If the growth rate A is smaller than R0, it is judged that the sample is not an HD-Hook-effect sample, and then the RLU1 of the sample to be detected is put into the calibration curve of RLU1 of the calibrator and the concentration of the calibrator to calculate the concentration of the sample to be detected; if the growth rate A is larger than R0, it is determined that the sample is an HD-Hook-effect sample and needs to be diluted before detection.

Example 1: Detection of Human Chorionic Gonadotropin and β Subunit (HCG+β) in Human Serum Samples Human chorionic gonadotropin and β subunit (HCG+β) detection reagent kit (chemiluminescence) purchased from Shanghai Beyond Biotech Co., Ltd was used to measure a concentration of human chorionic gonadotropin and β subunit (HCG+β) in a human serum sample. The reagent kit included: calibrators 1 to 6 (namely a series of known standard substances), a reagent 1 (which was a light-emitting antibody, namely light-emitting particles coated with an antibody), and a reagent 2 (which was a biotin-labeled antibody, namely an antibody labeled with biotin).

Calibrators 1 to 6: samples from routine reagent kits each with a known concentration that was much smaller than a concentration of an HD-Hook-effect sample. The calibrators were used to plot a calibration curve for calculation of a concentration of an analyte.

Other components used: LiCA general-purpose solution (light-sensitive particles labeled with streptavidin) which is an auxiliary reagent produced by Beyond Biotech Co., Ltd for a light initiated chemiluminescent assay system, and was used together with an apparatus and a corresponding light initiated chemiluminescence detection reagent kit to detect an antigen or antibody.

Serum samples of 18 patients whose HCG+β concentrations had been measured by Roche detection (samples exceeding a detection range were diluted before being detected) were subjected to detections by a conventional method and by a method provided by the present disclosure, respectively.

Detection by the Conventional Method:

A sample to be detected or a calibrator, a reagent 1 (which was a light-emitting antibody, namely light-emitting particles coated with a mouse monoclonal antibody), and a reagent 2 (a biotin-labeled antibody, namely a mouse monoclonal antibody labeled with biotin) were added into a reaction vessel to form a mixture. The mixture was then incubated at 37° C. for 15 min, followed by addition of a general-purpose solution (light-sensitive particles labeled with streptavidin) and incubation at 37° C. for 10 min. A photon counter was used to read a signal value which was marked as RLU and a concentration of the sample was calculated. Results were shown in Table 1.

Detection by a two-time-value-reading method of the present disclosure:

A sample to be detected or a calibrator, a reagent 1 (which was a light-emitting antibody, namely light-emitting particles coated with a mouse monoclonal antibody), and a reagent 2 (a biotin-labeled antibody, namely a mouse monoclonal antibody labeled with biotin) were added into a reaction vessel to form a mixture. The mixture was then incubated at 37° C. for 15 min, followed by addition of a general-purpose solution (light-sensitive particles labeled with streptavidin) and incubation at 37° C. for 3 min, and a signal value RLU1 was read. After that, the mixture was incubated again at 37° C. for 7 min, and a signal value RLU2 was read. A growth rate from the first-time-read-value RLU1 to the second-time-read-value RLU2 was calculated based on equation $A = (RLU2/RLU1 - 1) \times 100\%$. Results were shown in Table 1.

TABLE 1

Results of conventional detection and detection by the method of the present disclosure

| | | Roche detection results | Conventional detection results | | Detection results by method of the present discolsure | | | |
|---|---|---|---|---|---|---|---|---|
| | | Concentration | | | | | Growth | Concentration |
| | Samples | mIU/ml | RLU | concentration mIU/ml | RLU1 | RLU2 | rate A | mIU/ml |
| Calibrators | Calibrator 1 | / | 1983 | 0 | 1993 | 1651 | −17.2% | 0 |
| | Calibrator 2 | / | 11170 | 100 | 9873 | 6124 | −38.0% | 100 |
| | Calibrator 3 | / | 73186 | 500 | 56006 | 39442 | −29.6% | 500 |
| | Calibrator 4 | / | 171343 | 1000 | 153737 | 115945 | −24.6% | 1000 |

TABLE 1-continued

Results of conventional detection and detection by the method of the present disclosure

| | | Roche detection results | | | Detection results by method of the present discolsure | | | |
|---|---|---|---|---|---|---|---|---|
| | | Concentration | Conventional detection results | | | | Growth | Concentration |
| | Samples | mIU/ml | RLU | concentrationmIU/ml | RLU1 | RLU2 | rate A | mIU/ml |
| | Calibrator 5 | / | 872648 | 5000 | 798510 | 834788 | 4.5% | 5000 |
| | Calibrator 6 | / | 1445378 | 10000 | 1351347 | 1501961 | 11.1% | 10000 |
| Sample | Sample 1 | 147.7 | 14571 | 131.18 | 14390 | 9338 | −35.1% | 151.44 |
| to be | Sample 2 | 543.4 | 77284 | 521.85 | 69597 | 50276 | −27.8% | 582.05 |
| detected | Sample 3 | 1595 | 263783 | 1467.77 | 257403 | 223194 | −13.3% | 1510.45 |
| | Sample 4 | 2640 | 524358 | 2858.55 | 449878 | 434405 | −3.4% | 2576.9 |
| | Sample 5 | 3392 | 624970 | 3434.34 | 546275 | 543257 | −0.6% | 3179.16 |
| | Sample 6 | 5423 | 990911 | 5860.18 | 847724 | 901290 | 6.3% | 5394.53 |
| | Sample 7 | 7148 | 1093690 | 6683.92 | 939086 | 1014240 | 8.0% | 6157.43 |
| | Sample 8 | 7333 | 1112952 | 6846.58 | 998022 | 1090288 | 9.2% | 6670.19 |
| | Sample 9 | 9989 | 1381284 | 9356.74 | 1311265 | 1441974 | 10.0% | 9609.36 |
| | Sample 10 | 18179 | 1763185 | >10000.00 | 1548022 | 1738768 | 12.3% | >10000.00 |
| | Sample 11 | 27644 | 2132171 | >10000.00 | 1931997 | 2200548 | 13.9% | >10000.00 |
| | Sample 12 | 40992 | 2245202 | >10000.00 | 2012723 | 2297704 | 14.2% | >10000.00 |
| | Sample 13 | 54531 | 2346216 | >10000.00 | 2224037 | 2543796 | 14.4% | >10000.00 |
| | Sample 14 | 85660 | 2278130 | >10000.00 | 2067277 | 2366320 | 14.5% | >10000.00 |
| | Sample 15 | 92038 | 2179811 | >10000.00 | 1994236 | 2300927 | 15.4% | >10000.00 |
| | Sample 16 | 183338 | 1754015 | >10000.00 | 1725072 | 2015247 | 16.8% | >10000.00 |
| | Sample 17 | 207682 | 1649920 | >10000.00 | 1589155 | 1868936 | 17.6% | >10000.00 |
| | Sample 18 | 423574 | 1316175 | 8713.02 | 1273437 | 1518189 | 19.2% | >10000.00 |

Note:
A concentration range of HCG+β detected by a conventional method is 0-10000 mIU/ml, and if the concentration exceeds an upper limit of detection, it is shown that a concentration of the sample is larger than 10000 mIU/ml.

Figure 8:
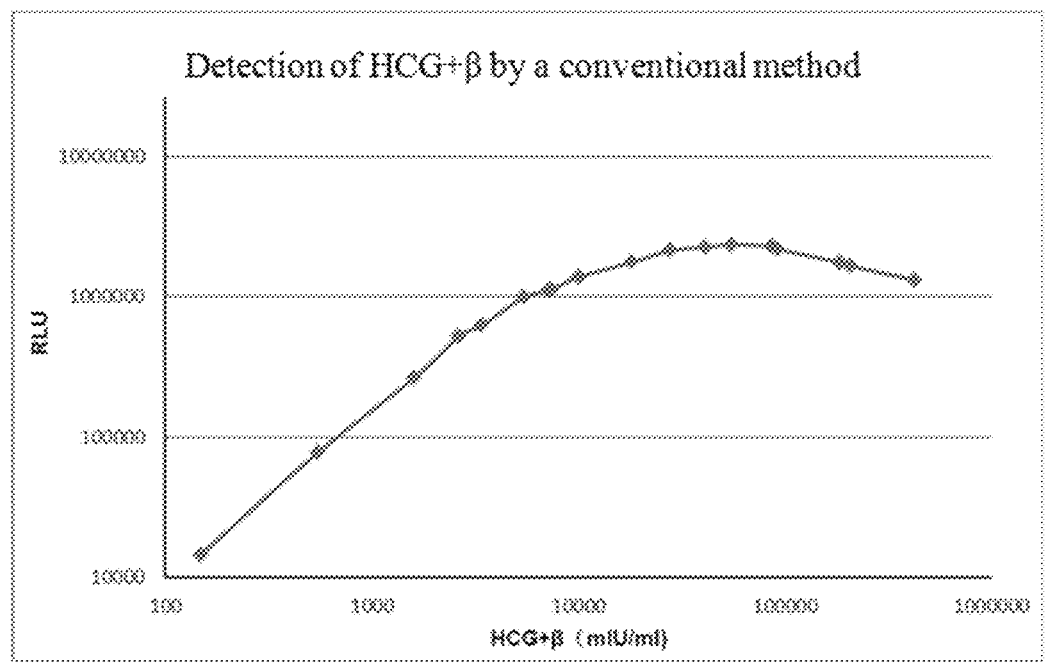
FIG. 8 is a curve showing a relationship between a signal value and a sample concentration in detection of HCG+β by a conventional method.

The concentration measured by Roche detection is considered as a real concentration. As shown in Table 1 and FIG. 8, in the conventional detection, before the concentration increases to 54531 mIU/ml, the signal value increases with the increase of the concentration; when the concentration continues to increase, the signal value decreases with the increase of the concentration of HCG+β. That was to say, HD-Hook effect occurs when the concentration is larger than 4531 mIU/ml. In the conventional detection, a concentration range detected is 0-10000 mIU/ml, and if the concentration exceeds an upper limit of detection, it is shown that the concentration of the sample is larger than 10000 mIU/ml. When the concentration of the HD-Hook-effect sample continues to increase and the signal value continues to decrease, a sample with a super high concentration would be detected as a sample with a low concentration, an example of which is sample 18. Therefore, in a conventional detection, it cannot be tell whether a result of the detected sample is a real concentration or a detected inaccurate low concentration caused by an effect of HD-Hook effect on the sample's super high concentration.

Figure 9:
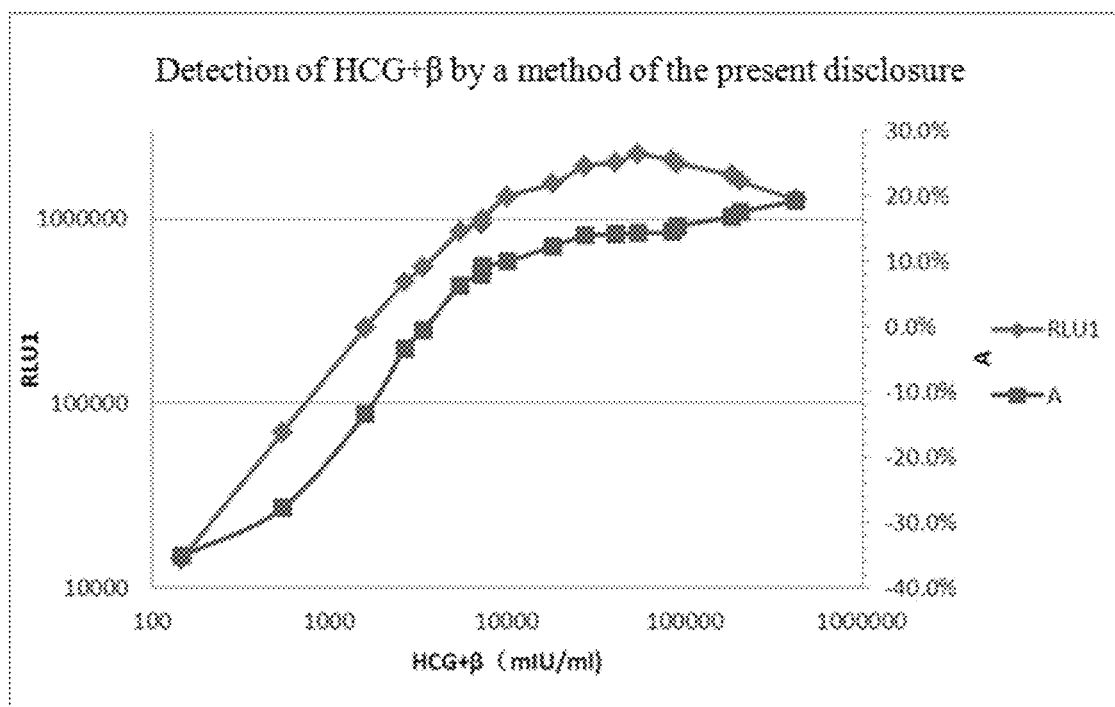
FIG. 9 is a curve showing a relationship between a signal value and a sample concentration and a relationship between a growth rate A and the sample concentration in detection of HCG+β by a method of the present disclosure.

The method of the present disclosure, by means of two times of value reading, determines a sample detected with a low concentration due to HD-Hook effect. Each sample is detected for two times to obtain two signal values RLU1 and RLU2. A growth rate A from the first-time-read-value to the second-time-read-value calculated based on the equation A=(RLU2/RLU1−1)×100% is used as an index for determining the concentration of the sample. As can be seen from Table 1 and FIG. 9, the signal value increases with the increase of the concentration before the concentration increases to 54531 mIU/ml, and after that, the signal value decreases with the increase of the concentration but the growth rate A continues to increase with the increase of the concentration. The concentration of the sample and the concentration of the calibrator can therefore be compared with each other by directly comparing the growth rate A with respect to the sample and the growth rate A with respect to the calibrator. Growth rates A with respect to samples 10 to 18 are all larger than the growth rate with respect calibrator 6 (11.1%), and the growth rates A show a continuously increasing trend. This shows that concentrations of HCG+β in samples 10 to 18 are all larger than 10000 mIU/ml and exhibit a continuously increasing trend, which result is consistent with the result of Roche detection. The signal value of sample 18 is smaller than that of calibrator 6, and a concentration of sample 18 detected by the conventional method is 8713.02 mIU/ml. It is determined by the method of the present disclosure that sample 18 is an HD-Hook-effect sample and needs to be diluted before detection.

Example 2: Detection of Ferritin (Ferr) in Samples

Ferr detection reagent kit (chemiluminescence) purchased from Shanghai Beyond Biotech Co., Ltd was used to measure a concentration of ferr (purchased from Fitzgerald, Catalog No: 30-AF10) in a sample. The reagent kit included: calibrators 1 to 6 (namely a series of known standard substances), a reagent 1 (which was a light-emitting antibody, namely light-emitting particles coated with an antibody), and a reagent 2 (which was a biotin-labeled antibody, namely an antibody labeled with biotin).

Calibrators 1 to 6: samples from routine reagent kits each with a known concentration that was much smaller than a concentration of an HD-Hook-effect sample. The calibrators were used to plot a calibration curve for calculation of a concentration of an analyte.

Other components used: LiCA general-purpose solution (light-sensitive particles labeled with streptavidin) which is an auxiliary reagent produced by Beyond Biotech Co., Ltd for a light initiated chemiluminescent assay system, and was used together with an apparatus and a corresponding light initiated chemiluminescence detection reagent kit to detect an antigen or antibody.

Gradient dilution was performed on a high-concentration ferr antigen. Concentrations of samples having different concentrations of ferr were detected by a conventional method and by a method of the present disclosure, respectively.

Detection by the Conventional Method:

Calibrators 1 to 6 or samples to be detected 1 to 15, a reagent 1 (which was a light-emitting antibody, namely light-emitting particles coated with a mouse monoclonal antibody), and a reagent 2 (a biotin-labeled antibody, namely a mouse monoclonal antibody labeled with biotin) were added into a reaction vessel to form a mixture. The mixture was then incubated at 37° C. for 15 min, followed by addition of a general-purpose solution (light-sensitive particles labeled with streptavidin) and incubation at 37° C. for 10 min. A photon counter was used to read a signal value which was marked as RLU. Results were shown in Table 2.

Detection by a two-time-value-reading method of the present disclosure:

Calibrators 1 to 6 or samples to be detected 1 to 15, a reagent 1 (which was a light-emitting antibody, namely light-emitting particles coated with a mouse monoclonal antibody), and a reagent 2 (a biotin-labeled antibody, namely a mouse monoclonal antibody labeled with biotin) were added into a reaction vessel to form a mixture. The mixture was then incubated at 37° C. for 15 min, followed by addition of a general-purpose solution (light-sensitive particles labeled with streptavidin) and incubation at 37° C. for 3 min, and a signal value RLU1 was read. After that, the mixture was incubated again at 37° C. for 7 min, and a signal value RLU2 was read. A growth rate from the first-time-read-value RLU1 to the second-time-read-value RLU2 was calculated based on equation $A=(RLU2/RLU1-1)\times 100\%$. Results were shown in Table 2.

tration; when the concentration continues to increase, the signal value decreases with the increase of the concentration of ferr. A concentration range detected by the conventional detection is 0-2000 ng/ml, and if the concentration exceeds an upper limit of detection, it is shown that the concentration of the sample is larger than 2000 ng/ml. When the concentration of the HD-Hook-effect sample continues to increase and increases to 2550000 ng/ml, and the signal value drops to a signal value smaller than that of calibrator 6, a sample with a super high concentration would be detected as a sample with a low concentration, an example of which is sample 15. Therefore, in a conventional detection, it cannot be tell whether a result of the detected sample is a real concentration or a detected inaccurate low concentration caused by an effect of HD-Hook effect on the sample's super high concentration.

The method of the present disclosure, by means of two times of value reading, determines a sample detected with a low concentration due to HD-Hook effect. Each sample is detected for two times to obtain two signal values RLU1 and RLU2. A growth rate A from the first-time-read-value to the second-time-read-value calculated based on the equation $A=(RLU2/RLU1-1)\times 100\%$ is used as an index for determining the concentration of the sample. As can be seen from Table 2 and FIG. 10, the signal value increases with the increase of the concentration before the concentration increases to 51000 ng/ml, and after that, the signal value decreases with the increase of the concentration but the growth rate A continues to increase with the increase of the concentration. The concentration of the sample and the concentration of the calibrator can therefore be compared with each other by directly comparing the growth rate A with respect to the sample and the growth rate A with respect to the calibrator. Growth rates A with respect to samples 4 to

TABLE 2

Results of conventional detection and detection by the method of the present disclosure

| | Samples | Real concentration Concentration ng/ml | Conventional detection results RLU | Conventional detection results Concentration ng/ml | Detection results by method of the present discolsure RLU1 | Detection results by method of the present discolsure RLU2 | Detection results by method of the present discolsure Growth rate A | Detection results by method of the present discolsure Concentration ng/ml |
|---|---|---|---|---|---|---|---|---|
| Calibrators | Calibrator 1 | 0 | 1504 | 0 | 1301 | 982 | −24.5% | 0 |
| | Calibrator 2 | 19.91 | 9470 | 19.91 | 8419 | 5699 | −32.3% | 19.91 |
| | Calibrator 3 | 101.02 | 46702 | 101.02 | 39701 | 31854 | −19.8% | 101.02 |
| | Calibrator 4 | 502.74 | 201992 | 502.74 | 177904 | 152780 | −14.1% | 502.74 |
| | Calibrator 5 | 994.36 | 382044 | 994.36 | 336189 | 299061 | −11.0% | 994.36 |
| | Calibrator 6 | 2232.94 | 745316 | 2232.94 | 701657 | 662840 | −5.5% | 2232.94 |
| Sample to be detected | Sample 1 | 20 | 10008 | 21.21 | 9010 | 6256 | −30.6% | 21.53 |
| | Sample 2 | 200 | 83614 | 184.44 | 75542 | 63340 | −16.2% | 196.81 |
| | Sample 3 | 2000 | 688675 | >2000 | 635950 | 595131 | −6.4% | >2000 |
| | Sample 4 | 5100 | 1131402 | >2000 | 1083169 | 1077907 | −0.5% | >2000 |
| | Sample 5 | 10200 | 1684984 | >2000 | 1448123 | 1526161 | 5.4% | >2000 |
| | Sample 6 | 15300 | 1966033 | >2000 | 1776540 | 1926924 | 8.5% | >2000 |
| | Sample 7 | 20400 | 2132659 | >2000 | 1907869 | 2132148 | 11.8% | >2000 |
| | Sample 8 | 25500 | 2288952 | >2000 | 1999686 | 2251677 | 12.6% | >2000 |
| | Sample 9 | 51000 | 2378260 | >2000 | 2113558 | 2407210 | 13.9% | >2000 |
| | Sample 10 | 102000 | 2304238 | >2000 | 2094861 | 2392541 | 14.2% | >2000 |
| | Sample 11 | 153000 | 2163232 | >2000 | 1903523 | 2210245 | 16.1% | >2000 |
| | Sample 12 | 204000 | 1958628 | >2000 | 1740069 | 2031467 | 16.7% | >2000 |
| | Sample 13 | 255000 | 1777808 | >2000 | 1615030 | 1899252 | 17.6% | >2000 |
| | Sample 14 | 510000 | 1401282 | >2000 | 1162934 | 1398233 | 20.2% | >2000 |
| | Sample 15 | 2550000 | 646266 | 1860.97 | 538637 | 668007 | 24.0% | >2000 |

Note:
A concentration range of ferr detected by a conventional method is 0-2000 ng/ml, and if the concentration exceeds an upper limit of detection, it is shown that a concentration of the sample is larger than 2000 ng/ml.

Figure 10:
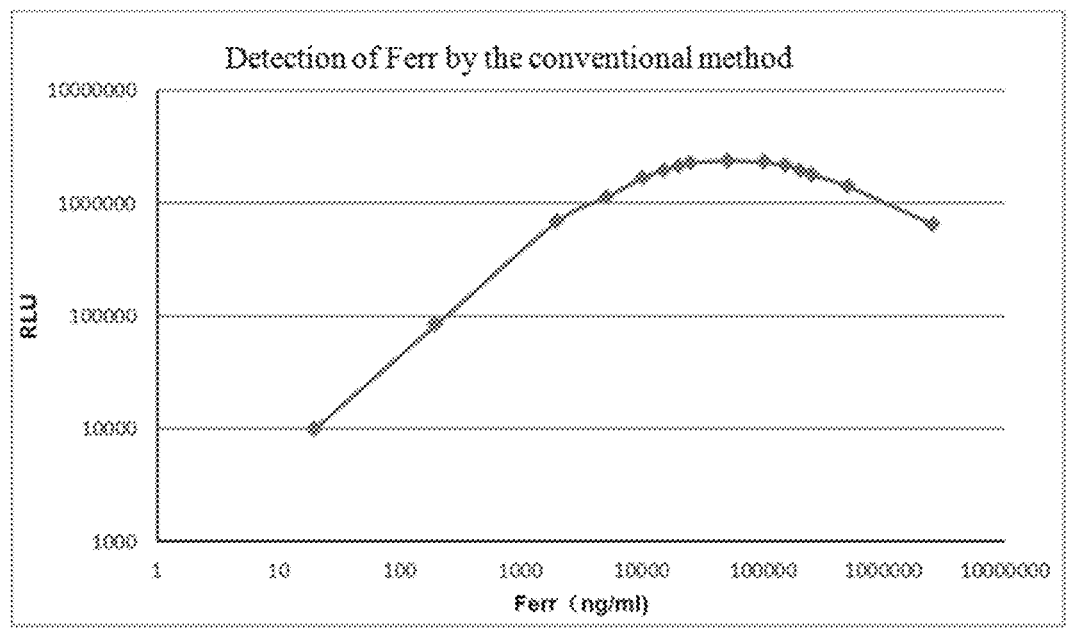
FIG. 10 is a curve showing a relationship between a signal value and a sample concentration in detection of Ferr by a conventional method.
Figure 11:
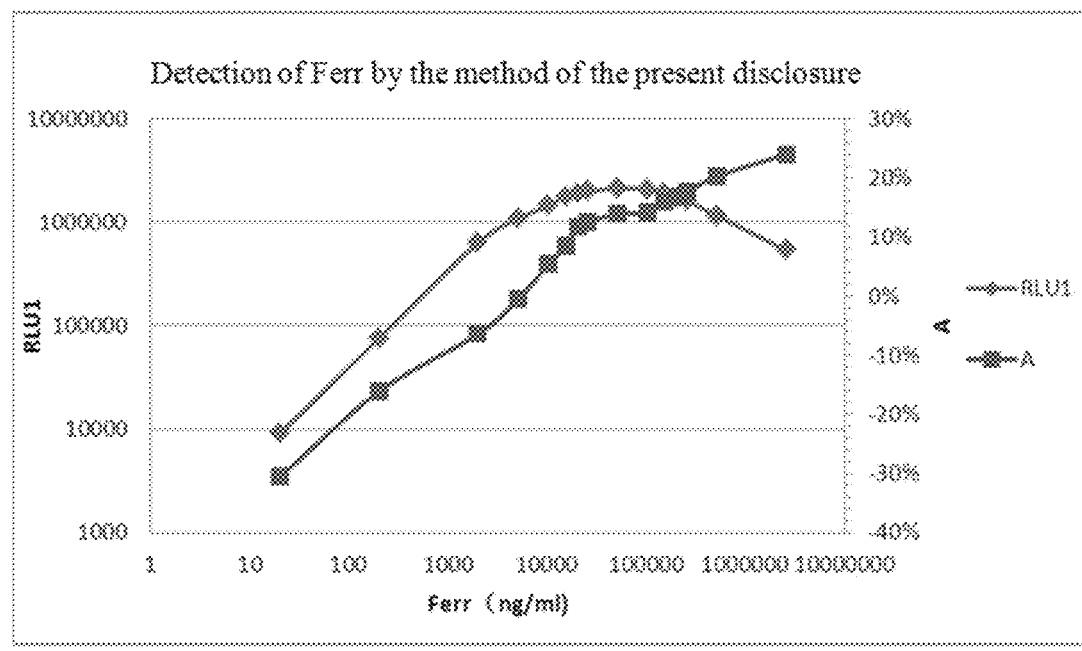
FIG. 11 is a curve showing a relationship between a signal value and a sample concentration and a relationship between a growth rate A and the sample concentration in detection of Ferr by a method of the present disclosure.

In the conventional detection, as shown in Table 2 and FIG. 10, before the concentration increases to 51000 ng/ml, the signal value increases with the increase of the concen- 15 are all larger than the growth rate with respect calibrator 6 (−5.5%). This shows that concentrations of ferr in samples 4 to 15 are all larger than 2000 ng/ml, which result is consistent with the real concentrations. The signal value of sample 15 is smaller than that of calibrator 6, and a concentration of sample 15 detected by the conventional method is 1860.97 ng/ml. It is determined by the method of the present disclosure that sample 15 is a sample with a concentration that exceeds the detection range and needs to be diluted before detection.

Example 3: Detection of C-Peptide (CP) in Samples

C-Peptide (CP) detection reagent kit (chemiluminescence) purchased from Shanghai Beyond Biotech Co., Ltd was used to measure a concentration of CP (purchased from Fitzgerald, Catalog No: 30-AC96) in a sample. The reagent kit included: calibrators 1 to 6 (namely a series of known standard substances), a reagent 1 (which was a light-emitting antibody, namely light-emitting particles coated with an antibody), and a reagent 2 (which was a biotin-labeled antibody, namely an antibody labeled with biotin).

Calibrators 1 to 6: samples from routine reagent kits each with a known concentration that was much smaller than a concentration of an HD-Hook-effect sample. The calibrators were used to plot a calibration curve for calculation of a concentration of an analyte.

Other components used: LiCA general-purpose solution (light-sensitive particles labeled with streptavidin) which is an auxiliary reagent produced by Beyond Biotech Co., Ltd for a light initiated chemiluminescent assay system, and was used together with an apparatus and a corresponding light initiated chemiluminescence detection reagent kit to detect an antigen or antibody.

Gradient dilution was performed on a high-concentration CP antigen. Concentrations of samples having different concentrations of CP were detected by a conventional method and by a method of the present disclosure, respectively.

Detection by the Conventional Method:

Calibrators 1 to 6 or samples to be detected 1 to 17, a reagent 1 (which was a light-emitting antibody, namely light-emitting particles coated with a mouse monoclonal antibody), and a reagent 2 (a biotin-labeled antibody, namely a mouse monoclonal antibody labeled with biotin) were added into a reaction vessel to form a mixture. The mixture was then incubated at 37° C. for 15 min, followed by addition of a general-purpose solution (light-sensitive particles labeled with streptavidin) and incubation at 37° C. for 10 min. A photon counter was used to read a signal value which was marked as RLU. Results were shown in Table 3.

Detection by a two-time-value-reading method of the present disclosure:

Calibrators 1 to 6 or samples to be detected 1 to 17, a reagent 1 (which was a light-emitting antibody, namely light-emitting particles coated with a mouse monoclonal antibody), and a reagent 2 (a biotin-labeled antibody, namely a mouse monoclonal antibody labeled with biotin) were added into a reaction vessel to form a mixture. The mixture was then incubated at 37° C. for 15 min, followed by addition of a general-purpose solution (light-sensitive particles labeled with streptavidin) and incubation at 37° C. for 3 min, and a signal value RLU1 was read. After that, the mixture was incubated again at 37° C. for 7 min, and a signal value RLU2 was read. A growth rate from the first-time-read-value RLU1 to the second-time-read-value RLU2 was calculated based on equation $A=(RLU2/RLU1-1)\times 100\%$. Results were shown in Table 3.

TABLE 3

Results of conventional detection and detection by the method of the present disclosure

| | Samples | Real concentration Concentration ng/ml | Conventional detection results RLU | Concentration ng/ml | Detection results by method of the present discolsure RLU1 | RLU2 | Growth rate A | Concentration ng/ml |
|---|---|---|---|---|---|---|---|---|
| Calibrators | Calibrator 1 | 0 | 304 | 0 | 302 | 331 | 9.6% | 0 |
| | Calibrator 2 | 0.59 | 2035 | 0.59 | 1778 | 1308 | −26.4% | 0.59 |
| | Calibrator 3 | 0.85 | 2539 | 0.85 | 2625 | 2016 | −23.2% | 0.85 |
| | Calibrator 4 | 6.02 | 11619 | 6.02 | 9717 | 8017 | −17.5% | 6.02 |
| | Calibrator 5 | 12.05 | 23261 | 12.05 | 21432 | 18465 | −13.8% | 12.05 |
| | Calibrator 6 | 33.31 | 55424 | 33.31 | 47809 | 45456 | −4.9% | 33.31 |
| Samples to be detected | Sample 1 | 1 | 2912 | 1.06 | 2900 | 2251 | −22.4% | 0.93 |
| | Sample 2 | 3 | 6499 | 3.12 | 5729 | 4545 | −20.7% | 2.37 |
| | Sample 3 | 10 | 20345 | 10.54 | 16747 | 13986 | −16.5% | 10.13 |
| | Sample 4 | 33 | 56700 | >30 | 44852 | 42492 | −5.3% | >30 |
| | Sample 5 | 100 | 162356 | >30 | 132253 | 139349 | 5.4% | >30 |
| | Sample 6 | 335 | 435784 | >30 | 359060 | 409421 | 14.0% | >30 |
| | Sample 7 | 1000 | 1458246 | >30 | 1147167 | 1367003 | 19.2% | >30 |
| | Sample 8 | 3350 | 2610397 | >30 | 2305534 | 2785700 | 20.8% | >30 |
| | Sample 9 | 10000 | 3170807 | >30 | 2669419 | 3292270 | 23.3% | >30 |
| | Sample 10 | 33500 | 2998354 | >30 | 2376362 | 2986650 | 25.7% | >30 |
| | Sample 11 | 100000 | 2165769 | >30 | 1717649 | 2233121 | 30.0% | >30 |
| | Sample 12 | 335000 | 946947 | >30 | 742994 | 981144 | 32.1% | >30 |
| | Sample 13 | 1000000 | 363059 | >30 | 297572 | 398779 | 34.0% | >30 |
| | Sample 14 | 3350000 | 162871 | >30 | 135756 | 184090 | 35.6% | >30 |
| | Sample 15 | 10000000 | 58143 | >30 | 46580 | 64473 | 38.4% | >30 |
| | Sample 16 | 33500000 | 15674 | 8.15 | 12274 | 17359 | 41.4% | >30 |
| | Sample 17 | 100000000 | 2379 | 0.76 | 1902 | 2693 | 41.6% | >30 |

Note:
A concentration range of CP detected by a conventional method is 0-30 ng/ml, and if the concentration exceeds an upper limit of detection, it is shown that a concentration of the sample is larger than 30 ng/ml.

Figure 12:
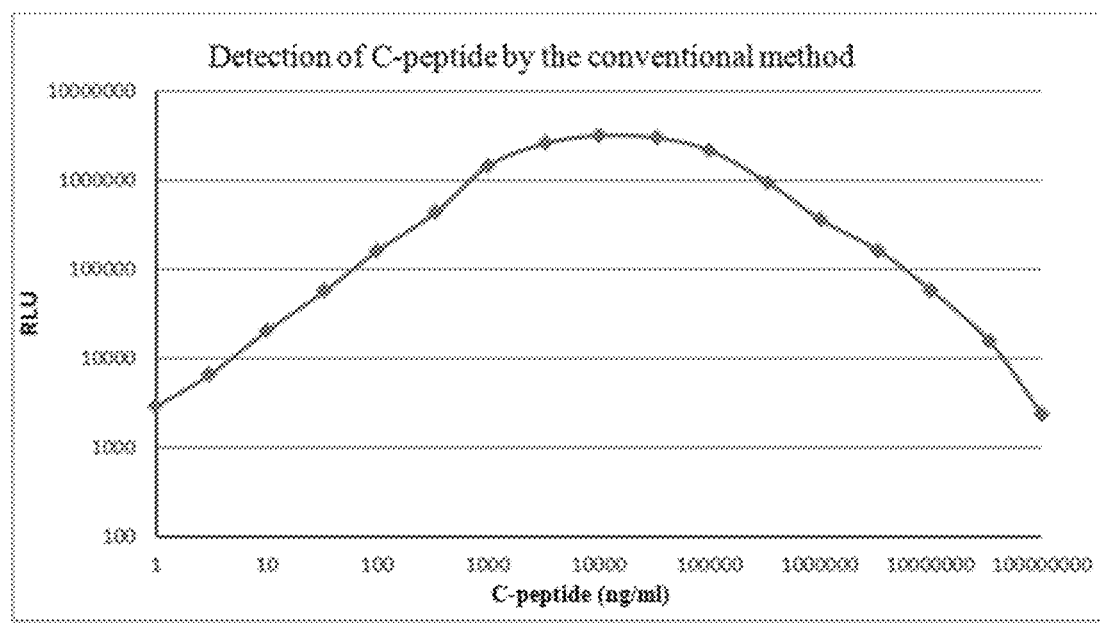
FIG. 12 is a curve showing a relationship between a signal value and a sample concentration in detection of C-peptide by a conventional method.

In the conventional detection, as shown in Table 3 and FIG. 12, before the concentration increases to 10000 ng/ml, the signal value increases with the increase of the concentration; when the concentration continues to increase, the signal value decreases with the increase of the concentration of CP. A concentration range detected by the conventional detection is 0-30 ng/ml, and if the concentration exceeds an upper limit of detection, it is shown that the concentration of the sample is larger than 30 ng/ml. When the concentration increases to 33500000 ng/ml, and the signal value drops to a signal value smaller than that of calibrator 6, a sample with a super high concentration would be detected as a sample with a low concentration, examples of which are samples 16 and 17. Therefore, in a conventional detection, it cannot be tell whether a result of the detected sample is a real concentration or a detected inaccurate low concentration caused by an effect of HD-Hook effect on the sample's super high concentration.

Figure 13:
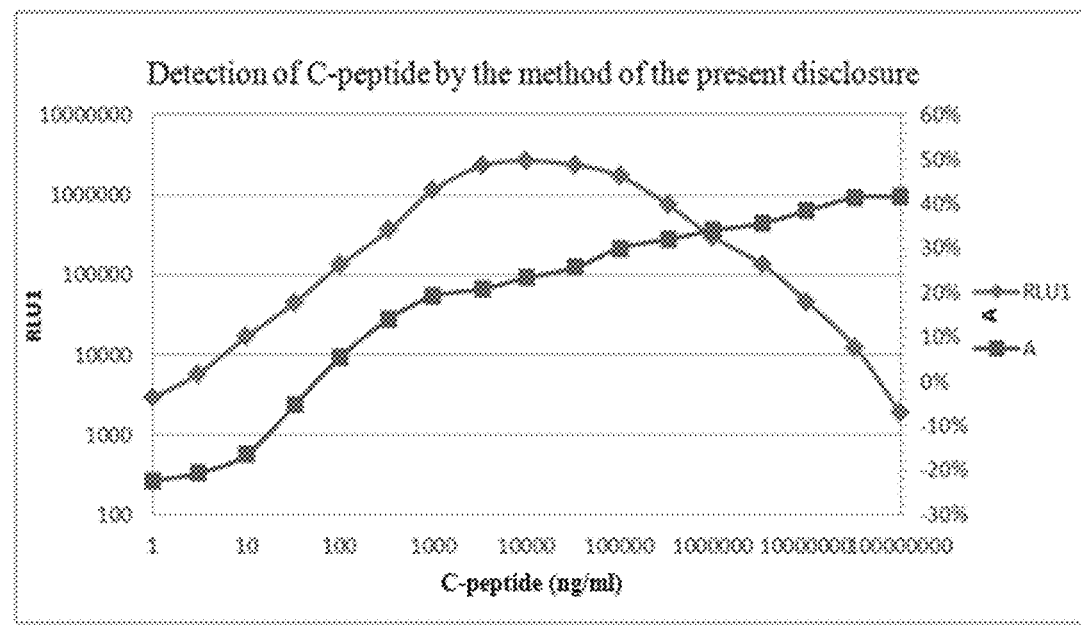
FIG. 13 is a curve showing a relationship between a signal value and a sample concentration and a relationship between a growth rate A and the sample concentration in detection of C-peptide by a method of the present disclosure.

The method of the present disclosure, by means of two times of value reading, determines a sample detected with a low concentration due to HD-Hook effect. Each sample is detected for two times to obtain two signal values RLU1 and RLU2. A growth rate A from the first-time-read-value to the second-time-read-value calculated based on the equation $A=(RLU2/RLU1-1)\times 100\%$ is used as an index for determining the concentration of the sample. As can be seen from Table 3 and FIG. 13, the signal value increases with the increase of the concentration before the concentration increases to 10000 ng/ml, and after that, the signal value decreases with the increase of the concentration but the growth rate A continues to increase with the increase of the concentration. The concentration of the sample and the concentration of the calibrator can therefore be compared with each other by directly comparing the growth rate A with respect to the sample and the growth rate A with respect to the calibrator. Growth rates A with respect to samples 5 to 17 are all larger than the growth rate with respect calibrator 6 (−4.9%). This shows that concentrations of CP in samples 5 to 17 are all larger than 30 ng/ml, i.e. exceeds the upper limit of the detection, which result is consistent with real concentrations. The signal values with respect to samples 16 and 17 are smaller than that of calibrator 6, and concentrations of samples 16 and 17 detected by the conventional method are 8.15 ng/ml and 0.76 ng/ml, respectively. It is determined by the method of the present disclosure that samples 16 and 17 are samples with concentrations that exceed the upper limit of the detection and needs to be diluted before detection.

Example 4: Detection of Hepatitis B Virus Surface Antigen (HBsAg) in Human Serum Samples Hepatitis B Virus Surface Antigen (HBsAg) detection reagent kit (chemiluminescence) purchased from Shanghai Beyond Biotech Co., Ltd was used to measure a concentration of HBsAg in a sample. The reagent kit included: calibrators 1 to 6 (namely a series of known standard substances), a reagent 1 (which was a light-emitting antibody, namely light-emitting particles coated with an antibody), and a reagent 2 (which was a biotin-labeled antibody, namely an antibody labeled with biotin).

Calibrators 1 to 6: samples from routine reagent kits each with a known concentration that was much smaller than a concentration of an HD-Hook-effect sample. The calibrators were used to plot a calibration curve for calculation of a concentration of an analyte.

Other components used: LiCA general-purpose solution (light-sensitive particles labeled with streptavidin) which is an auxiliary reagent produced by Beyond Biotech Co., Ltd for a light initiated chemiluminescent assay system, and was used together with an apparatus and a corresponding light initiated chemiluminescence detection reagent kit to detect an antigen or antibody.

Calibrators 1 to 6 and samples 1 to 15 to be detected were detected using the method of the present disclosure. Specifically, an analyte, a reagent 1 (light-emitting particles coated with an antibody), and a reagent 2 (a biotin-labeled antibody) were added into a reaction vessel to form a mixture. The mixture was then incubated at 37° C. for 15 min, followed by addition of a general-purpose solution (light-sensitive particles labeled with streptavidin) and incubation at 37° C. for 3 min, and a signal value RLU1 was read. After that, the mixture was incubated again at 37° C. for 7 min, and a signal value RLU2 was read. A growth rate from the first-time-read-value RLU1 to the second-time-read-value RLU2 was calculated based on equation $A=(RLU2/RLU1-1)\times 100\%$. Results were shown in Table 4.

TABLE 4

Results by the detection method of the present discolsure

| | Samples | RLU1 | RLU2 | Growth rate A | Concentration IU/ml |
|---|---|---|---|---|---|
| Calibrators | Calibrator 1 | 422 | 480 | 14% | 0 |
| | Calibrator 2 | 837 | 963 | 15% | 0.1 |
| | Calibrator 3 | 1810 | 2178 | 20% | 0.9 |
| | Calibrator 4 | 36396 | 45223 | 24% | 27.56 |
| | Calibrator 5 | 200089 | 250799 | 25% | 156.46 |
| | Calibrator 6 | 396371 | 502928 | 27% | 336.56 |
| Samples to be detected | Sample 1 | 144451 | 202472 | 40% | >336.56 |
| | Sample 2 | 145010 | 206857 | 43% | >336.56 |
| | Sample 3 | 232678 | 318684 | 37% | >336.56 |
| | Sample 4 | 415121 | 534674 | 29% | >336.56 |
| | Sample 5 | 349098 | 468840 | 34% | >336.56 |
| | Sample 6 | 83799 | 123879 | 48% | >336.56 |
| | Sample 7 | 171530 | 211953 | 24% | 137.07 |
| | Sample 8 | 199010 | 251351 | 26% | 159.34 |
| | Sample 9 | 375057 | 498512 | 33% | >336.56 |
| | Sample 10 | 325790 | 409503 | 26% | 250.82 |
| | Sample 11 | 225486 | 282838 | 25% | 188.59 |
| | Sample 12 | 97703 | 141949 | 45% | >336.56 |
| | Sample 13 | 103552 | 150462 | 45% | >336.56 |
| | Sample 14 | 193000 | 263358 | 36% | >336.56 |
| | Sample 15 | 280822 | 370651 | 32% | >336.56 |

Concentrations of samples 1 to 15 detected by the method of the present disclosure were shown in Table 4. Samples with concentrations exceeding an upper limit of detection (336.56 IU/mL) were firstly determined by comparing growth rates with respect to these samples with a growth rate with respect to calibrator 6. In other words, samples each with a growth rate A that was larger than 27% were determined as HD-Hook-effect samples which should be diluted before detection. Samples each with a growth rate A that was smaller than 27% were samples with concentrations within the detection range, and concentrations thereof could be calculated using a calibration curve.

Reliability of the above results was verified by gradiently diluting the samples and then detecting concentrations thereof. Specifically, two-fold dilution and four-fold dilution were performed on samples 1 to 15, and then a conventional detection method was used to detect the undiluted original samples, the samples after two-fold dilution, and the samples after four-fold dilution. By observing variations of the concentrations of the samples, it was determined whether a sample was an HD-Hook-effect sample or not. If a sample had an increased concentration after it was diluted, it was determined that the sample was an HD-Hook-effect sample. If a sample had a decreased concentration after it was diluted, it was determined that the sample was not an HD-Hook-effect sample. Results were shown in Table 5.

TABLE 5

Verification results after sample dilution

| Samples diluted and verified | Detected concentrations | | | |
|---|---|---|---|---|
| | Undiluted original samples | Samples after two-fold dilution | Samples after four-fold dilution | Concentrations IU/mL |
| Sample 1 | 128.79 | 262.17 | 474.22 | HOOK |
| Sample 2 | 135.81 | 249.87 | 417.08 | HOOK |
| Sample 3 | 228.96 | 388.23 | 642.69 | HOOK |
| Sample 4 | 369.11 | 222.22 | 124.14 | 369.11 |
| Sample 5 | 353.47 | 618.94 | 886.34 | HOOK |
| Sample 6 | 74.52 | 132.14 | 226.20 | HOOK |
| Sample 7 | 134.44 | 60.89 | 31.22 | 134.44 |
| Sample 8 | 154.76 | 72.45 | 36.50 | 154.76 |
| Sample 9 | 331.50 | 546.11 | 881.46 | HOOK |
| Sample 10 | 260.78 | 104.97 | 49.26 | 260.78 |
| Sample 11 | 174.00 | 97.86 | 51.41 | 174.00 |
| Sample 12 | 82.80 | 176.16 | 328.03 | HOOK |
| Sample 13 | 94.92 | 192.47 | 367.37 | HOOK |
| Sample 14 | 158.96 | 277.50 | 434.39 | HOOK |
| Sample 15 | 269.64 | 480.82 | 814.12 | HOOK |

As can be seen from Table 5, serum samples 1, 2, 3, 5, 6, 9, 12, 13, 14, and 15 are detected to have increased concentrations after they are diluted. This shows that these samples are HD-Hook-effect samples and have concentrations larger than 336.56 IU/mL. Serum samples 4, 7, 8, 10, and 11 are detected to have reduced concentrations after they are diluted, which shows that these samples are not HD-Hook-effect samples. These results are consistent with those detected by the method of the present disclosure.

Example 5: Detection of CA125 in Human Serum Samples

Carbohydrate antigen 125 (CA125) detection reagent kit (chemiluminescence) purchased from Shanghai Beyond Biotech Co., Ltd was used to measure a concentration of CA125 in a sample. The reagent kit included: calibrators 1 to 6 (namely a series of known standard substances), a reagent 1 (which was a light-emitting antibody, namely light-emitting particles coated with an antibody), and a reagent 2 (which was a biotin-labeled antibody, namely an antibody labeled with biotin).

Calibrators 1 to 6: samples from routine reagent kits each with a known concentration that was much smaller than a concentration of an HD-Hook-effect sample. The calibrators were used to plot a calibration curve for calculation of a concentration of an analyte.

Other components used: LiCA general-purpose solution (light-sensitive particles labeled with streptavidin) which is an auxiliary reagent produced by Beyond Biotech Co., Ltd for a light initiated chemiluminescent assay system, and was used together with an apparatus and a corresponding light initiated chemiluminescence detection reagent kit to detect an antigen or antibody.

Calibrators 1 to 6 and samples 1 to 18 to be detected were detected using the method of the present disclosure. Specifically, an analyte, a reagent 1 (light-emitting particles coated with an antibody), and a reagent 2 (a biotin-labeled antibody) were added into a reaction vessel to form a mixture. The mixture was then incubated at 37° C. for 15 min, followed by addition of a general-purpose solution (light-sensitive particles labeled with streptavidin) and incubation at 37° C. for 3 min, and a signal value RLU1 was read. After that, the mixture was incubated again at 37° C. for 7 min, and a signal value RLU2 was read. A growth rate from the first-time-read-value RLU1 to the second-time-read-value RLU2 was calculated based on equation $A=(RLU2/RLU1-1)\times 100\%$. Results were shown in Table 6.

TABLE 6

Results by the detection method of the present disclosure

| | Samples | RLU1 | RLU2 | Growth rate A | Concentration U/ml |
|---|---|---|---|---|---|
| Calibrators | Calibrator 1 | 999 | 744 | −25.5% | 0 |
| | Calibrator 2 | 10857 | 8248 | −24.0% | 9.17 |
| | Calibrator 3 | 21563 | 17508 | −18.8% | 19.11 |
| | Calibrator 4 | 102708 | 88869 | −13.5% | 87.53 |
| | Calibrator 5 | 271593 | 259355 | −4.5% | 251.58 |
| | Calibrator 6 | 794718 | 853603 | 7.4% | 1043.74 |
| Samples to be detected | Sample 1 | 9665 | 7217 | −25.3% | 8.06 |
| | Sample 2 | 16130 | 12287 | −23.8% | 14.09 |
| | Sample 3 | 51059 | 42166 | −17.4% | 44.79 |
| | Sample 4 | 71055 | 59021 | −16.9% | 61.36 |
| | Sample 5 | 92952 | 80019 | −13.9% | 79.39 |
| | Sample 6 | 196716 | 178735 | −9.1% | 173.32 |
| | Sample 7 | 225436 | 213141 | −5.5% | 202.34 |
| | Sample 8 | 290252 | 281001 | −3.2% | 272.3 |
| | Sample 9 | 340529 | 345889 | 1.6% | 330.44 |
| | Sample 10 | 465955 | 478028 | 2.6% | 492.14 |
| | Sample 11 | 513321 | 530012 | 3.3% | 560.23 |
| | Sample 12 | 711508 | 760017 | 6.8% | 889.7 |
| | Sample 13 | 908842 | 973276 | 7.1% | >1000.00 |
| | Sample 14 | 1845773 | 2103378 | 14.0% | >1000.00 |
| | Sample 15 | 2390350 | 2772269 | 16.0% | >1000.00 |
| | Sample 16 | 688606 | 859340 | 24.8% | >1000.00 |
| | Sample 17 | 560058 | 709209 | 26.6% | >1000.00 |
| | Sample 18 | 453979 | 584179 | 28.7% | >1000.00 |

Concentrations of samples 1 to 18 detected by the method of the present disclosure were shown in Table 6. Samples with concentrations exceeding an upper limit of detection were firstly determined by comparing growth rates with respect to these samples with a growth rate with respect to calibrator 6. In other words, samples each with a growth rate A that was larger than 7.4% were determined as samples with concentrations exceeding the upper limit of the detection. These samples should be diluted before being detected. Samples each with a growth rate A that was smaller than 7.4% were not HD-Hook-effect samples, and concentrations thereof could be directly calculated using a calibration curve.

Reliability of the above results was verified by gradiently diluting the samples and then detecting concentrations thereof. Specifically, two-fold dilution and four-fold dilution were performed on samples 1 to 18, and then a conventional detection method was used to detect the undiluted original samples, the samples after two-fold dilution, and the samples after four-fold dilution. By observing variations of the concentrations of the samples, it was determined whether a sample was an HD-Hook-effect sample or not. If a sample had an increased concentration after it was diluted, it was determined that the sample was an HD-Hook-effect sample. If a sample had a decreased concentration after it was diluted, it was determined that the sample was not an HD-Hook-effect sample. Results were shown in Table 7.

TABLE 7

Verification results after sample dilution

| Samples diluted and verified | Detected concentrations | | | Concentrations U/mL |
|---|---|---|---|---|
| | Undiluted original samples | Samples after two-fold dilution | Samples after four-fold dilution | |
| Sample 1 | 8.02 | 4.36 | 2.26 | 8.02 |
| Sample 2 | 13.42 | 7.21 | 3.32 | 13.42 |
| Sample 3 | 47.14 | 25.17 | 11.8 | 47.14 |
| Sample 4 | 66.49 | 30.09 | 16.19 | 66.49 |
| Sample 5 | 80.84 | 44.42 | 20.86 | 80.84 |
| Sample 6 | 167.73 | 81.77 | 41.22 | 167.73 |
| Sample 7 | 192.31 | 101.89 | 49.65 | 192.31 |
| Sample 8 | 300.92 | 154.39 | 78.77 | 300.92 |
| Sample 9 | 352.65 | 170.05 | 87.05 | 352.65 |
| Sample 10 | 528.74 | 260.36 | 127.31 | 528.74 |
| Sample 11 | 612.44 | 299.05 | 141.28 | 612.44 |
| Sample 12 | 901.35 | 447.07 | 213.5 | 901.35 |
| Sample 13 | >1000.00 | 559.3 | 258.1 | >1000.00 |
| Sample 14 | >1000.00 | >1000.00 | 551.3 | >1000.00 |
| Sample 15 | >1000.00 | >1000.00 | 771.9 | >1000.00 |
| Sample 16 | 830.97 | 992.82 | >1000.00 | HOOK |
| Sample 17 | 734.25 | 934.91 | >1000.00 | HOOK |
| Sample 18 | 550.42 | 778.12 | >1000.00 | HOOK |

As can be seen from Table 7, serum samples 16, 17, and 18 are detected to have increased concentrations after they are diluted. This shows that these samples are HD-Hook-effect samples. Serum samples 1 to 15 are detected to have reduced concentrations after they are diluted, which shows that these samples are not HD-Hook-effect samples. These results are consistent with those detected by the method of the present disclosure. In the case that the samples are not diluted and are detected with the conventional method, the serum samples 16, 17, and 18 would be inaccurately detected each with a low concentration because of HD-Hook effect.

Example 6: Detection of Hepatitis B Virus Surface Antibody (HBsAb) in Samples

Hepatitis B Virus Surface Antibody (HBsAb) detection reagent kit HBsAbHBsAb (chemiluminescence) purchased from Shanghai Beyond Biotech Co., Ltd was used to measure a concentration of HBsAb (purchased from Beijing Genstars Biotech Co., Ltd, Clone No: M2201) in a sample. The reagent kit included: calibrators 1 to 6 (namely a series of known standard substances), a reagent 1 (which was a light-emitting antibody, namely light-emitting particles coated with an antibody), and a reagent 2 (which was a biotin-labeled antibody, namely an antibody labeled with biotin).

Calibrators 1 to 6: samples from routine reagent kits each with a known concentration that was much smaller than a concentration of an HD-Hook-effect sample. The calibrators were used to plot a calibration curve for calculation of a concentration of an analyte.

Other components used: LiCA general-purpose solution (light-sensitive particles labeled with streptavidin) which is an auxiliary reagent produced by Beyond Biotech Co., Ltd for a light initiated chemiluminescent assay system, and was used together with an apparatus and a corresponding light initiated chemiluminescence detection reagent kit to detect an antigen or antibody.

Gradient dilution was performed on a high-concentration HBsAb. Concentrations of samples having different concentrations of HBsAb were detected by a conventional method and by a method of the present disclosure, respectively.

Detection by the Conventional Method:

Calibrators 1 to 6 or samples to be detected 1 to 14, a reagent 1 (light-emitting particles coated with HBsAg), and a reagent 2 (biotin-labeled HBsAg) were added into a reaction vessel to form a mixture. The mixture was then incubated at 37° C. for 15 min, followed by addition of a general-purpose solution (light-sensitive particles labeled with streptavidin) and incubation at 37° C. for 10 min. A photon counter was used to read a signal value which was marked as RLU. Results were shown in Table 8.

Detection by a two-time-value-reading method of the present disclosure:

Calibrators 1 to 6 or samples to be detected 1 to 14, a reagent 1 (light-emitting particles coated with HBsAg), and a reagent 2 (biotin-labeled HBsAg) were added into a reaction vessel to form a mixture. The mixture was then incubated at 37° C. for 15 min, followed by addition of a general-purpose solution (light-sensitive particles labeled with streptavidin) and incubation at 37° C. for 3 min, and a signal value RLU1 was read. After that, the mixture was incubated again at 37° C. for 7 min, and a signal value RLU2 was read. A growth rate from the first-time-read-value RLU1 to the second-time-read-value RLU2 was calculated based on equation A=(RLU2/RLU1−1)×100%. Results were shown in Table 8.

TABLE 8

Results of conventional detection and detection by the method of the present disclosure

| | Samples | Real concentration Concentration mIU/ml | Conventional detection results | | Detection results by method of the present discolsure | | | |
|---|---|---|---|---|---|---|---|---|
| | | | RLU | Concentration mIU/ml | RLU1 | RLU2 | Growth rate A | Concentration mIU/ml |
| Calibrators | Calibrator 1 | 0 | 524 | 0 | 498 | 523 | 5.0% | 0 |
| | Calibrator 2 | 10.23 | 3548 | 10.23 | 3188 | 4049 | 27.0% | 10.23 |
| | Calibrator 3 | 71.95 | 21493 | 71.95 | 17403 | 22854 | 31.3% | 71.95 |
| | Calibrator 4 | 213.65 | 64993 | 213.65 | 50526 | 67526 | 33.6% | 213.65 |
| | Calibrator 5 | 584.26 | 181544 | 584.26 | 133863 | 180954 | 35.2% | 584.26 |
| | Calibrator 6 | 1026.18 | 342125 | 1026.18 | 255651 | 347371 | 35.9% | 1026.18 |
| Samples to be detected | Sample 1 | 1 | 703 | 0.6 | 652 | 737 | 13.0% | 0.58 |
| | Sample 2 | 3 | 1257 | 2.48 | 1182 | 1424 | 20.5% | 2.58 |
| | Sample 3 | 10 | 3443 | 9.87 | 2876 | 3592 | 24.9% | 9.02 |
| | Sample 4 | 33 | 9387 | 30.24 | 7743 | 10124 | 30.8% | 28.78 |
| | Sample 5 | 100 | 31033 | 103.93 | 25555 | 33721 | 32.0% | 107.83 |
| | Sample 6 | 335 | 101781 | 332.87 | 79257 | 106917 | 34.9% | 341.56 |
| | Sample 7 | 1,000 | 341483 | >1000 | 259926 | 352344 | 35.6% | >1000 |

TABLE 8-continued

Results of conventional detection and detection by the method of the present disclosure

| | Real concentration | Conventional detection results | | Detection results by method of the present discolsure | | | |
|---|---|---|---|---|---|---|---|
| Samples | Concentration mIU/ml | RLU | Concentration mIU/ml | RLU1 | RLU2 | Growth rate A | Concentration mIU/ml |
| Sample 8  | 3,350     | 757906  | >1000  | 570542 | 781231  | 36.9% | >1000 |
| Sample 9  | 10,000    | 1050237 | >1000  | 775542 | 1066620 | 37.5% | >1000 |
| Sample 10 | 33,500    | 985422  | >1000  | 753452 | 1039798 | 38.0% | >1000 |
| Sample 11 | 100,000   | 576535  | >1000  | 415949 | 577782  | 38.9% | >1000 |
| Sample 12 | 335,000   | 258461  | 802.57 | 184878 | 259170  | 40.2% | >1000 |
| Sample 13 | 1,000,000 | 107739  | 352.22 | 75811  | 109111  | 43.9% | >1000 |
| Sample 14 | 3,350,000 | 44514   | 147.9  | 33501  | 48374   | 44.4% | >1000 |

Note:
A concentration range of HBsAb detected by a conventional method is 0-1000 mIU/ml, and if the concentration exceeds an upper limit of detection, it is shown that a concentration of the sample is larger than 1000 mIU/ml.

Figure 14:
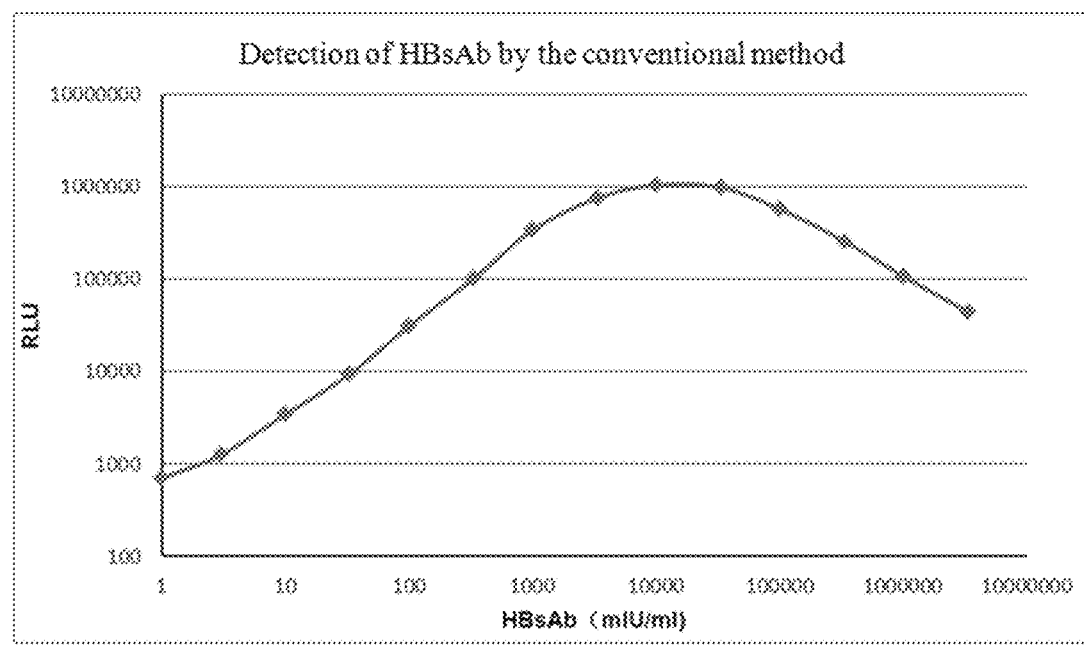
FIG. 14 is a curve showing a relationship between a signal value and a sample concentration in detection of HBsAb by a conventional method.

In the conventional detection, as shown in Table 8 and FIG. 14, before the concentration increases to 10000 mIU/ml, the signal value increases with the increase of the concentration; when the concentration continues to increase, the signal value decreases with the increase of the concentration of HBsAb. A concentration range detected by the conventional detection is 0-1000 mIU/ml, and if the concentration exceeds an upper limit of detection, it is shown that the concentration of the sample is larger than 1000 mIU/ml. When the concentration increases to 335000 mIU/ml, and the signal value drops to a signal value smaller than that of calibrator 6, a sample with a super high concentration would be detected as a sample with a low concentration, examples of which are samples 12, 13 and 14. Therefore, in a conventional detection, it cannot be tell whether a result of the detected sample is a real concentration or a detected inaccurate low concentration caused by an effect of HD-Hook effect on the sample's super high concentration.

Figure 15:
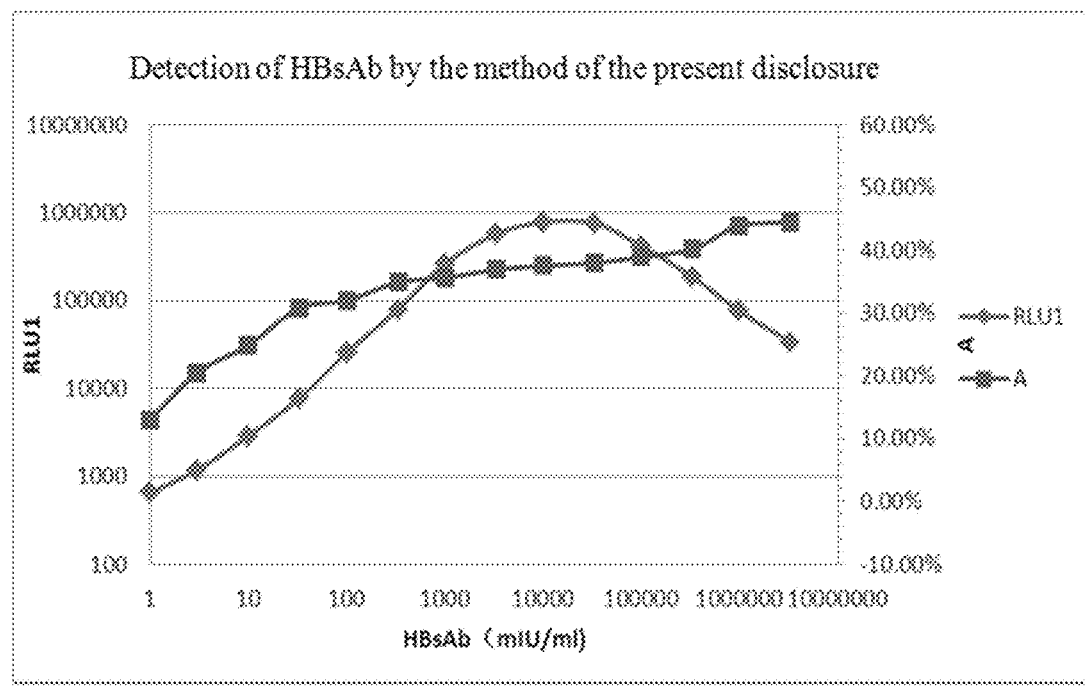
FIG. 15 is a curve showing a relationship between a signal value and a sample concentration and a relationship between a growth rate A and the sample concentration in detection of HBsAb by a method of the present disclosure.

The method of the present disclosure, by means of two times of value reading, determines a sample detected with a low concentration due to HD-Hook effect. Each sample is detected for two times to obtain two signal values RLU1 and RLU2. A growth rate A from the first-time-read-value to the second-time-read-value calculated based on the equation A=(RLU2/RLU1−1)×100% is used as an index for determining the concentration of the sample. As can be seen from Table 8 and FIG. 15, the signal value increases with the increase of the concentration before the concentration increases to 10000 mIU/ml, and after that, the signal value decreases with the increase of the concentration but the growth rate A continues to increase with the increase of the concentration. The concentration of the sample and the concentration of the calibrator can therefore be compared with each other by directly comparing the growth rate A with respect to the sample and the growth rate A with respect to the calibrator. Growth rates A with respect to samples 8 to 14 are all larger than the growth rate with respect calibrator 6 (35.9%). This shows that concentrations of HBsAb in samples 8 to 14 are all larger than 1000 mIU/ml, i.e. exceeds the upper limit of the detection, which result is consistent with real concentrations. The signal values with respect to samples 12, 13, and 14 are smaller than that with respect to calibrator 6, and concentrations of samples 12, 13, and 14 detected by the conventional method are 802.57 mIU/ml, 352.22 mIU/ml, and 147.9 mIU/ml, respectively. It is determined by the method of the present disclosure that samples 12, 13, and 14 are samples with concentrations that exceed the upper limit of the detection and needs to be diluted before detection.

Example 7: Use of the Method of the Present Disclosure in Anti-HCV Qualitative Reagent Kit Hepatitis C virus (HCV) antibody detection reagent kit (chemiluminescence) purchased from Shanghai Beyond Biotech Co., Ltd was used to measure a concentration of anti-HCV in a sample. The reagent kit included: a reference, a negative control, a positive control, a reagent 1 (light-emitting HCV antigen, namely light-emitting particles coated with an HCV antigen), and a reagent 2 (a biotin-labeled HCV antigen, namely an HCV antigen coated with biotin).

The reference, the negative control, the positive control: The reference was a standard substance with a known concentration and was as used as a reference for determining whether a sample to be detected was positive or negative. The negative and positive control each were a standard substance with a known concentration and were used for assessing validity of a test. Gradient dilution was performed on a high-concentration HBsAb. A high-concentration anti-HCV was gradiently diluted. Signal values with respect to samples having different concentrations of anti-HCV were detected by a conventional method and by a method of the present disclosure, respectively.

Detection by the Conventional Method:

A series of gradiently diluted anti-HCV samples, a reagent 1 (a light-emitting HCV antigen, namely light-emitting particles coated with an HCV antigen), and a reagent 2 (a biotin-labeled HCV antigen, namely an HCV antigen labeled with biotin) were added into a reaction vessel to form a mixture. The mixture was then incubated at 37° C. for 15 min, followed by addition of a general-purpose solution (light-sensitive particles labeled with streptavidin) and incubation at 37° C. for 10 min. A photon counter was used to read a signal value which was marked as RLU. Results were shown in Table 9.

Detection by a two-time-value-reading method of the present disclosure:

A series of gradiently diluted anti-HCV samples, a reagent 1 (a light-emitting HCV antigen, namely light-emitting particles coated with an HCV antigen), and a reagent 2 (a biotin-labeled HCV antigen, namely an HCV antigen labeled with biotin) were added into a reaction vessel to form a mixture. The mixture was then incubated at 37° C. for 15 min, followed by addition of a general-purpose solution (light-sensitive particles labeled with streptavidin) and incubation at 37° C. for 3 min, and a signal value RLU1 was read. After that, the mixture was incubated again at 37° C. for 7 min, and a signal value RLU2 was read. A growth rate from the first-time-read-value RLU1 to the second-time-read-value RLU2 was calculated based on equation A=(RLU2/RLU1−1)×100%. Results were shown in Table 9.

TABLE 9

Results of conventional detection and detection by the method of the present disclosure

| | | Conventional detection results | | | Detection results by method of the present discolsure | | | | |
|---|---|---|---|---|---|---|---|---|---|
| Samples | | RLU | S/CO | Results interpretation | RLU1 | RLU2 | Growth rate A | S/CO | Results interpretation |
| References | Cut off | 8666 | / | / | 7597 | 5497 | −28% | / | / |
| | Negative contorl | 2114 | 0.2 | − | 1849 | 1209 | −35% | 0.2 | − |
| | Positive control | 73593 | 8.5 | + | 66895 | 49895 | −25% | 8.8 | + |
| Samples | Dilution-fold | | | | | | | | |
| Sample 1 | 33500000 | 7219 | 0.8 | − | 6323 | 4518 | −29% | 0.8 | − |
| Sample 2 | 10000000 | 26240 | 3.0 | + | 24509 | 17799 | −27% | 3.2 | + |
| Sample 3 | 3350000 | 87461 | 10.1 | + | 83267 | 63218 | −24% | 11.0 | + |
| Sample 4 | 1000000 | 394790 | 45.6 | + | 353729 | 286326 | −19% | 46.6 | + |
| Sample 5 | 335000 | 1007623 | 116.3 | + | 941139 | 788127 | −16% | 123.9 | + |
| Sample 6 | 100000 | 1433764 | 165.4 | + | 1241174 | 1119498 | −10% | 163.4 | + |
| Sample 7 | 33500 | 1782108 | 205.6 | + | 1643897 | 1562180 | −5% | 216.4 | + |
| Sample 8 | 10000 | 1818732 | 209.9 | + | 1717605 | 1690209 | −2% | 226.1 | + |
| Sample 9 | 3350 | 1543275 | 178.1 | + | 1418948 | 1490332 | 5% | 186.8 | + |
| Sample 10 | 1000 | 1124849 | 129.8 | + | 1039330 | 1282719 | 23% | 136.8 | + |
| Sample 11 | 335 | 417289 | 48.2 | + | 382049 | 518552 | 36% | 50.3 | + |
| Sample 12 | 100 | 181511 | 20.9 | + | 172745 | 241657 | 40% | 22.7 | + |
| Sample 13 | 33 | 44905 | 5.2 | + | 42530 | 61166 | 44% | 5.6 | + |
| Sample 14 | 10 | 5429 | 0.6 | − | 5176 | 7630 | 47% | 0.7 | + |

As shown in Table 9, after the dilution-fold of antigen is reduced to 10000-fold, the signal value decreases with the increase of the concentration, and HD-Hook effect occurs. When the concentration continues to increase to a certain value (e.g. sample 14), RLU decreases to a value lower than cut off, in which case a false negative result is produced by the conventional method. By the method of the present disclosure, however, the growth rates A from the first-time-read-values to the second-time-read-value are observed first, and the growth rates A with respects to the samples are compared with a growth rate A with respect to the positive control (−25%), by way of which it can be determined whether concentrations of the samples are larger than or smaller than a concentration of the positive control. As shown in Table 9, the growth rate with respect to sample 14 (47%) is much larger than the growth rate of the positive control (−25%). This shows that the concentration of sample 14 is larger than that of the positive control, and therefore sample 14 is a positive sample. The reason for the low signal value with respect to sample 14 is HD-Hook effect and sample 14 needs to be diluted for verification.

Example 8: Detection of Insulin (INS) in Samples

Insulin (INS) detection reagent kit (chemiluminescence) purchased from Shanghai Beyond Biotech Co., Ltd was used to measure a concentration of INS (purchased from Fitzgerald, Catalog No: 30R-2704) in a sample.

Gradient dilution was performed on a high-concentration INS antigen. Signal values with respect to samples having different concentrations of INS were detected by a conventional method and by a method of the present disclosure, respectively.

Detection by the Conventional Method:

A sample to be detected with a known concentration, a reagent 1 (which was a light-emitting antibody, namely light-emitting particles coated with a mouse monoclonal antibody), and a reagent 2 (a biotin-labeled antibody, namely a mouse monoclonal antibody labeled with biotin) were added into a reaction vessel to form a mixture. The mixture was then incubated at 37° C. for 15 min, followed by addition of a general-purpose solution (light-sensitive particles labeled with streptavidin) and incubation at 37° C. for 10 min. A photon counter was used to read a signal value which was marked as RLU. Results were shown in Table 10.

Detection by a two-time-value-reading method of the present disclosure:

A sample to be detected with a known concentration, a reagent 1 (which was a light-emitting antibody, namely light-emitting particles coated with a mouse monoclonal antibody), and a reagent 2 (a biotin-labeled antibody, namely a mouse monoclonal antibody labeled with biotin) were added into a reaction vessel to form a mixture. The mixture was then incubated at 37° C. for 15 min, followed by addition of a general-purpose solution (light-sensitive particles labeled with streptavidin) and incubation at 37° C. for 3 min, and a signal value RLU1 was read. After that, the mixture was incubated again at 37° C. for 7 min, and a signal value RLU2 was read. A growth rate from the first-time-read-value RLU1 to the second-time-read-value RLU2 was calculated based on equation A=(RLU2/RLU1−1)×100%. Results were shown in Table 10.

TABLE 10

Results of conventional detection and
detection by the method of the present disclosure

| Concentration (μIU/ml) | Conventional detection results RLU | Detection results by method of the present discolsure | | |
|---|---|---|---|---|
| | | RLU1 | RLU2 | Growth Rate A |
| 3 | 3031 | 3132 | 2058 | −34% |
| 10 | 11328 | 9809 | 6631 | −32% |
| 33 | 33433 | 30397 | 21212 | −30% |
| 100 | 152385 | 117194 | 86069 | −27% |
| 335 | 732465 | 503568 | 449149 | −11% |
| 1,000 | 1797417 | 1342726 | 1446642 | 8% |
| 3,350 | 2441794 | 1857062 | 2100576 | 13% |
| 10,000 | 2470762 | 1880534 | 2247857 | 20% |
| 33,500 | 2033507 | 1482999 | 1958095 | 32% |
| 100,000 | 1209233 | 786883 | 1228586 | 56% |
| 335,000 | 464717 | 273591 | 483967 | 77% |
| 1,000,000 | 100765 | 58998 | 115157 | 95% |

Figure 16:
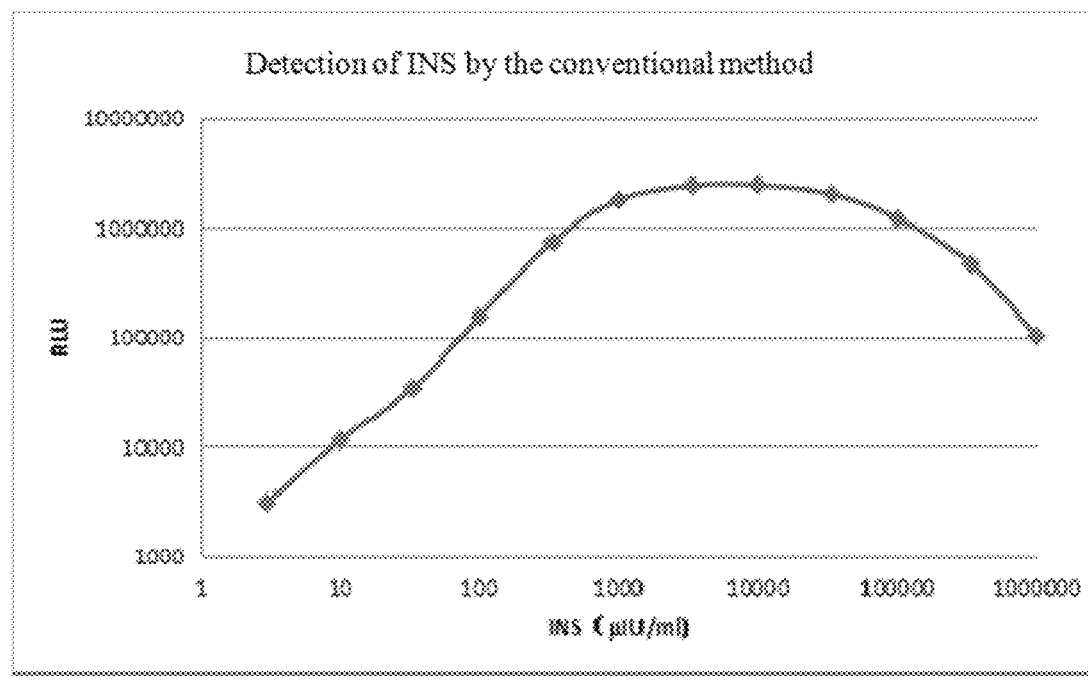
FIG. 16 is a curve showing a relationship between a signal value and a sample concentration in detection of INS by a conventional method.

As can be seen from Table 10 and FIG. 16, as the concentration increases from 3 μIU/ml to 10000 μIU/ml, the signal value increases with the increase of the concentration. As the concentration continues to increase, the signal value decreases with the increase of the concentration of INS. That is to say, when the concentration is larger than 10,000 μIU/ml, HD-Hook effect occurs. In a conventional detection, a sample with an antigen concentration larger than such a detection range would be detected as a sample with a low antigen concentration (the detected concentration would be smaller than 10,000 μIU/ml).

The method of the present disclosure, by means of two times of value reading, expands the detection range. Each sample is detected for two times to obtain two signal values RLU1 and RLU2. A growth rate A from the first-time-read-value to the second-time-read-value calculated based on the equation A=(RLU2/RLU1−1)×100% is used as an index for determining a concentration range of a sample. As can be seen from Table 10 and FIG. 17, the signal value continuously increases with the increase of the concentration before the concentration increases to 10,000 μIU/ml, after that, the signal value starts to decrease with the increase of the concentration, but the growth rate A increases continuously with the increase of the concentration.

Figure 17:
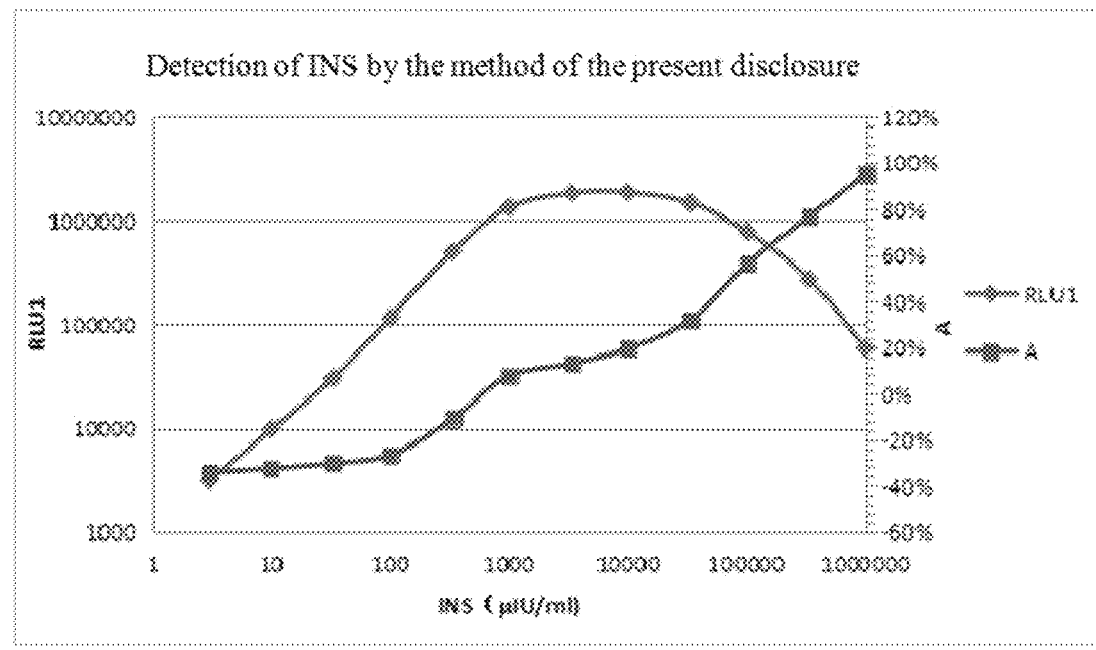
FIG. 17 is a curve showing a relationship between a first-time-read-value and a sample concentration and a relationship between a growth rate A and the sample concentration in detection of INS by a method of the present disclosure.

When concentrations of INS calibrators range from 3 μIU/ml to 1,000,000 μIU/ml, the method of the present disclosure is adopted to draw a calibration curve and a standard curve respectively based on RLU1 and growth rate A (as shown in FIG. 17). With the increase of the concentration, the growth rate A continuously increases. The curve of RLU1 consists of a rising section from 3 μIU/ml to 10,000 μIU/ml and a dropping section from 10,000 μIU/ml to 1,000,000 μIU/ml. RLU1, RLU2, and growth rate A with respect to the sample to be detected are obtained by the method of the present disclosure. A concentration of the analyte can be calculated by first determining, based on the growth rate A, whether the concentration of the analyte is located in the rising section from 3 μIU/ml to 10,000 μIU/ml or in the dropping section from 10,000 μIU/ml to 1,000,000 μIU/ml, and then putting the RLU1 of the analyte into a corresponding calibration curve.

As can be seen in Table 10, when the concentration of INS is 10,000 μIU/ml, the signal value reaches to its peak, and the corresponding growth rate A is 20%. If the growth rate with respect to the analyte is smaller than 20%, it is determined that the sample is not an HD-Hook-effect sample, and its concentration is calculated by putting its RLU1 into a section of the calibration curve where a concentration is smaller than 10,000 μIU/ml. If the growth rate with respect to the analyte is larger than or equal to 20%, it is determined that the sample is an HD-Hook-effect sample, and its concentration is calculated by putting its RLU1 into a section of the calibration curve where a concentration is larger than 10,000 μIU/ml. By way of this, the upper limit of the detection range is increased from 10,000 μIU/ml to 1,000,000 μIU/ml.

Example 9: Detection of Hepatitis B Virus Surface Antibody (HBsAb) in Samples

Hepatitis B Virus Surface Antibody (HBsAb) detection reagent kit (chemiluminescence) purchased from Shanghai Beyond Biotech Co., Ltd was used to measure a concentration of HBsAb (purchased from Beijing Genstars Biotech Co., Ltd, Clone No: M2201) in a sample.

Gradient dilution was performed on high-concentration HBsAb. Signal values of samples having different concentrations of HBsAb were detected by a conventional method and by a method of the present disclosure, respectively.

Detection by the Conventional Method:

Gradiently diluted HBsAb samples, a reagent 1 (light-emitting particles coated with HBsAg), and a reagent 2 (biotin-labeled HBsAg) were added into a reaction vessel to form a mixture. The mixture was then incubated at 37° C. for 15 min, followed by addition of a general-purpose solution (light-sensitive particles labeled with streptavidin) and incubation at 37° C. for 10 min. A photon counter was used to read a signal value which was marked as RLU.

Detection by a two-time-value-reading method of the present disclosure:

Gradiently diluted HBsAb samples, a reagent 1 (light-emitting particles coated with HBsAg), and a reagent 2 (biotin-labeled HBsAg) were added into a reaction vessel to form a mixture. The mixture was then incubated at 37° C. for 15 min, followed by addition of a general-purpose solution (light-sensitive particles labeled with streptavidin) and incubation at 37° C. for 3 min, and a signal value RLU1 was read. After that, the mixture was incubated again at 37° C. for 7 min, and a signal value RLU2 was read. A growth rate A from the first-time-read-value RLU1 to the second-time-read-value RLU2 was calculated based on equation A=(RLU2/RLU1−1)×100%. Results were shown in Table 11.

TABLE 11

Results of conventional detection and detection
by the method of the present disclosure

| Concentration (mIU/ml) | Conventional detection results RLU | Detection results by method of the present discolsure | | |
|---|---|---|---|---|
| | | RLU1 | RLU2 | Growth Rate A |
| 1 | 703 | 652 | 737 | 13.0% |
| 3 | 1257 | 1182 | 1424 | 20.5% |
| 10 | 3443 | 2876 | 3592 | 24.9% |
| 33 | 9387 | 7743 | 10124 | 30.8% |
| 100 | 31033 | 25555 | 33721 | 32.0% |
| 335 | 101781 | 79257 | 106917 | 34.9% |
| 1,000 | 341483 | 259926 | 352344 | 35.6% |
| 3,350 | 757906 | 570542 | 781231 | 36.9% |
| 10,000 | 1050237 | 775542 | 1066620 | 37.5% |
| 33,500 | 985422 | 753452 | 1039798 | 38.0% |
| 100,000 | 576535 | 415949 | 577782 | 38.9% |
| 335,000 | 258461 | 184878 | 259170 | 40.2% |

TABLE 11-continued

Results of conventional detection and detection
by the method of the present disclosure

| Concentration | Conventional detection results | Detection results by method of the present discolsure | | |
|---|---|---|---|---|
| (mIU/ml) | RLU | RLU1 | RLU2 | Growth Rate A |
| 1,000,000 | 107739 | 75811 | 109111 | 43.9% |
| 3,350,000 | 44514 | 33501 | 48374 | 44.4% |

Figure 18:
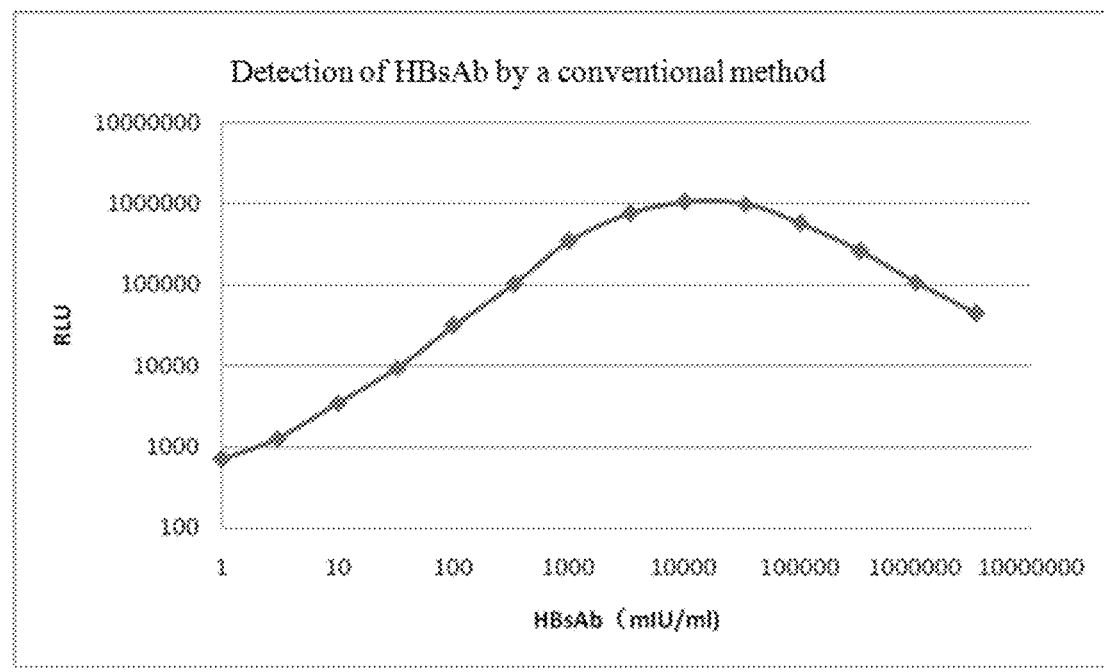
FIG. 18 is a curve showing a relationship between a signal value and a sample concentration in detection of HBsAb by a conventional method.

As can be seen from Table 11 and FIG. 18, as the concentration increases from 1 mIU/ml to 10000 mIU/ml, the signal value increases with the increase of the concentration. As the concentration continues to increase, the signal value decreases with the increase of the concentration of HBsAb. That is to say, when the concentration is larger than 10,000 mIU/ml, HD-Hook effect occurs. In a conventional detection, a sample with an antigen concentration larger than such a detection range would be detected as a sample with a low antigen concentration (the detected concentration would be smaller than 10,000 mIU/ml).

The method of the present disclosure, by means of two times of value reading, expands the detection range. Each sample is detected for two times to obtain two signal values RLU1 and RLU2. A growth rate A from the first-time-read-value to the second-time-read-value calculated based on the equation A=(RLU2/RLU1−1)×100% is used as an index for determining a concentration range of a sample. As can be seen from Table 11 and FIG. 19, the signal value continuously increases with the increase of the concentration before the concentration increases to 10,000 mIU/ml, after that, the signal value starts to decrease with the increase of the concentration, but the growth rate A increases continuously with the increase of the concentration.

Figure 19:
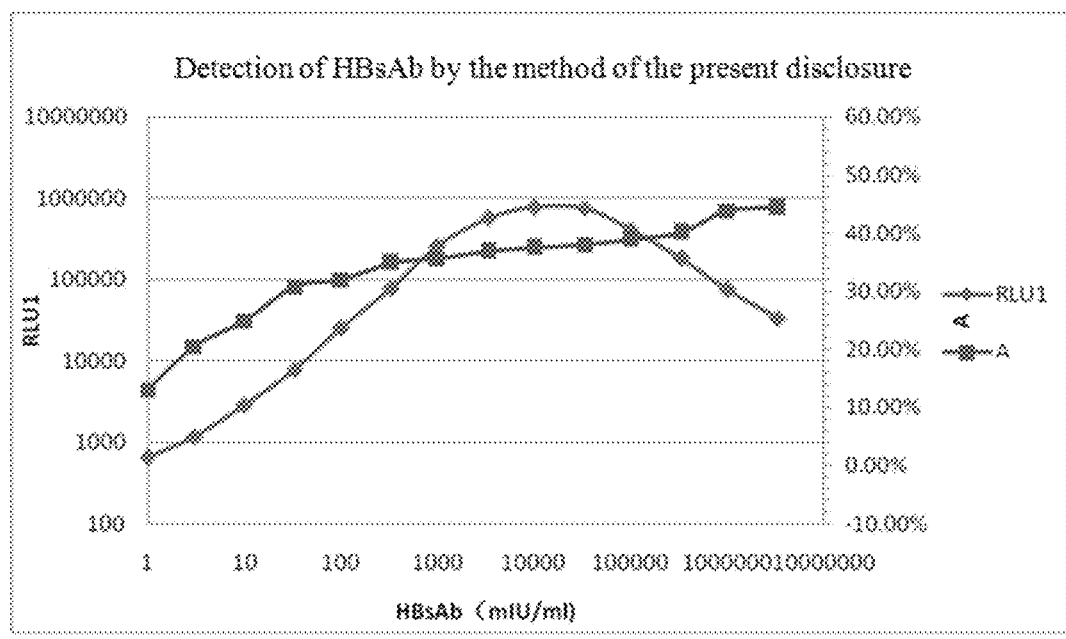
FIG. 19 is a curve showing a relationship between a first-time-read-value and a sample concentration and a relationship between a growth rate A and the sample concentration in detection of HBsAb by a method of the present disclosure.

When concentrations of HBsAb calibrators range from 1 mIU/ml to 3,350,000 mIU/ml, the method of the present disclosure is adopted to draw a calibration curve and a standard curve respectively based on RLU1 and growth rate A (as shown in FIG. 19). With the increase of the concentration, the growth rate A continuously increases. The curve of RLU1 consists of a rising section from 1 mIU/ml to 10,000 mIU/ml and a dropping section from 10,000 mIU/ml to 3,350,000 mIU/ml. RLU1, RLU2, and growth rate A with respect to the sample to be detected are obtained by the method of the present disclosure. A concentration of the analyte can be calculated by first determining, based on the growth rate A, whether the concentration of the analyte is located in the rising section from 1 mIU/ml to 10,000 mIU/ml or in the dropping section from 10,000 mIU/ml to 3,350,000 mIU/ml, and then putting the RLU1 of the analyte into a corresponding calibration curve.

As can be seen in Table 11, when the concentration of HBsAb is 10,000 μIU/ml, the signal value reaches to its peak, and the corresponding growth rate A is 37.5%. If the growth rate with respect to the analyte is smaller than 37.5%, it is determined that the sample is not an HD-Hook-effect sample, and its concentration is calculated by putting its RLU1 into a section of the calibration curve where a concentration is smaller than 10,000 mIU/ml. If the growth rate with respect to the analyte is larger than or equal to 37.5%, it is determined that the sample is an HD-Hook-effect sample, and its concentration is calculated by putting its RLU1 into a section of the calibration curve where a concentration is larger than 10,000 mIU/ml. By way of this, the upper limit of the detection range is increased from 10,000 mIU/ml to 3,350,000 mIU/ml.

Example 10: Detection of Alpha-Fetoprotein (AFP) in a Sample

Alpha-fetoprotein (AFP) detection reagent kit (chemiluminescence) purchased from Shanghai Beyond Biotech Co., Ltd was used to measure a concentration of AFP (purchased from Fitzgerald, Catalog No: 30-1370) in a sample.

Gradient dilution was performed on high-concentration AFP. Signal values of samples having different concentrations of AFP were detected by a conventional method and by a method of the present disclosure, respectively. Reference is made to Example 8 for description of the conventional detection method and the method of the present disclosure. Results of the detections were shown in Table 12.

TABLE 11

Results of conventional detection and
detection by the method of the present disclosure

| Concentration | Conventional detection results | Detection results by method of the present discolsure | | |
|---|---|---|---|---|
| (ng/ml) | RLU | RLU1 | RLU2 | Growth Rate |
| 5 | 6236 | 5240 | 3196 | −39% |
| 20 | 28026 | 21592 | 13538 | −37% |
| 100 | 192398 | 134766 | 103650 | −23% |
| 500 | 1075656 | 814013 | 829990 | 2% |
| 1,000 | 1729407 | 1342554 | 1508052 | 12% |
| 10,000 | 2817087 | 2132217 | 2513551 | 18% |
| 35,000 | 1874558 | 1443089 | 1761348 | 22% |
| 70,000 | 1280414 | 988315 | 1235805 | 25% |
| 100,000 | 1019883 | 766931 | 976572 | 27% |
| 350,000 | 327178 | 236131 | 306697 | 30% |
| 700,000 | 139241 | 97740 | 129928 | 33% |
| 1,000,000 | 58911 | 40668 | 54969 | 35% |

Figure 20:
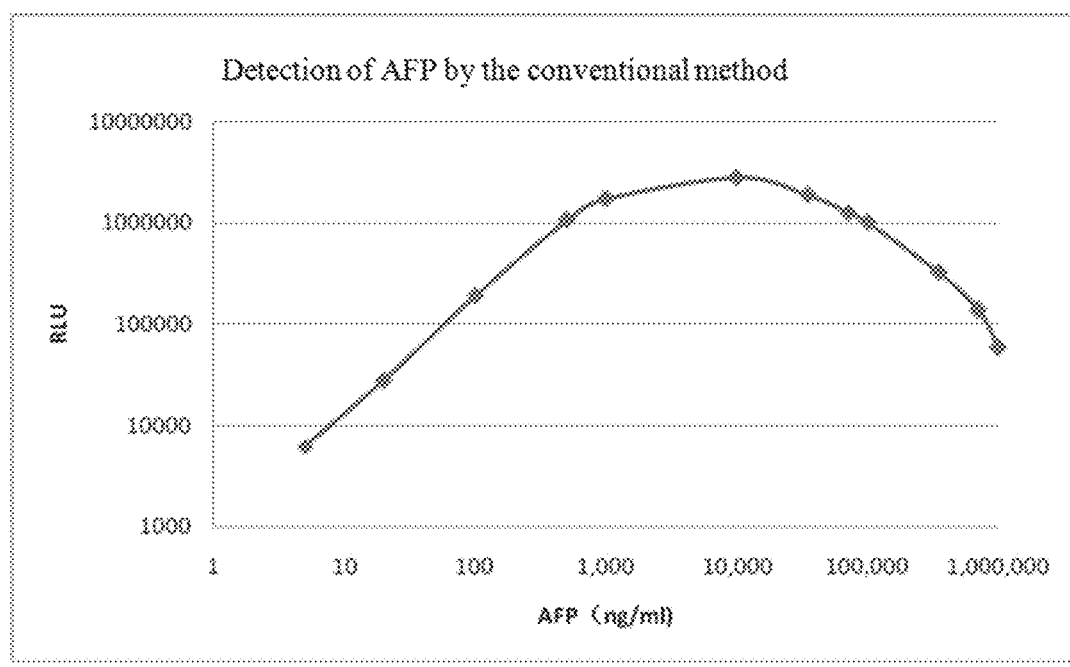
FIG. 20 is a curve showing a relationship between a signal value and a sample concentration in detection of AFP by a conventional method.

As can be seen from Table 12 and FIG. 20, as the concentration increases from 5 ng/ml to 10000 ng/ml, the signal value increases with the increase of the concentration. As the concentration continues to increase, the signal value decreases with the increase of the concentration of AFP. That is to say, when the concentration is larger than 10,000 ng/ml, HD-Hook effect occurs. In a conventional detection, a sample with an antigen concentration larger than such a detection range would be detected as a sample with a low antigen concentration (the detected concentration would be smaller than 10,000 ng/ml).

The method of the present disclosure, by means of two times of value reading, expands the detection range. Each sample is detected for two times to obtain two signal values RLU1 and RLU2. A growth rate A from the first-time-read-value to the second-time-read-value calculated based on the equation A=(RLU2/RLU1−1)×100% is used as an index for determining a concentration range of a sample. As can be seen from Table 12 and FIG. 21, the signal value continuously increases with the increase of the concentration before the concentration increases to 10,000 ng/ml, after that, the signal value starts to decrease with the increase of the concentration, but the growth rate A increases continuously with the increase of the concentration.

Figure 21:
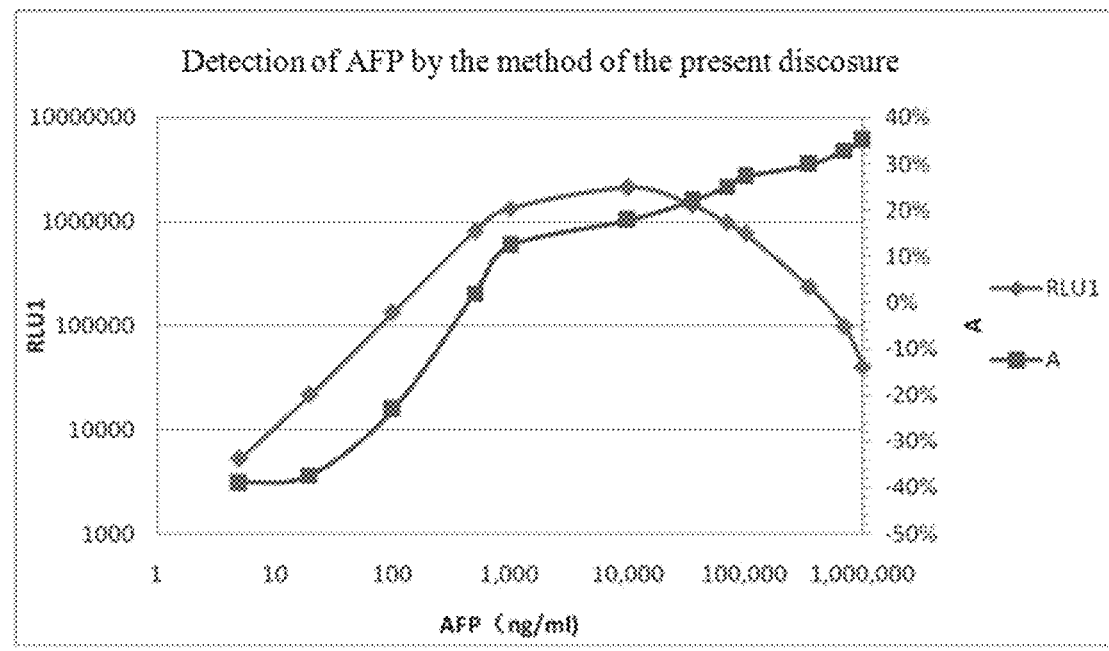
FIG. 21 is a curve showing a relationship between a first-time-read-value and a sample concentration and a relationship between a growth rate A and the sample concentration in detection of AFP by a method of the present disclosure.

When concentrations of AFP calibrators range from 5 ng/ml to 1,000,000 ng/ml, the method of the present disclosure is adopted to draw a calibration curve and a standard curve respectively based on R1U1 and growth rate A (as shown in FIG. 21). With the increase of the concentration, the growth rate A continuously increases. The curve of RLU1 consists of a rising section from 5 ng/ml to 10,000 ng/ml and a dropping section from 10,000 ng/ml to 1,000,000 ng/ml. RLU1, RLU2, and growth rate A with respect to the sample to be detected are obtained by the method of the present disclosure. A concentration of the analyte can be calculated by first determining, based on the growth rate A, whether the concentration of the analyte is located in the rising section from 5 ng/ml to 10,000 ng/ml or in the dropping section from 10,000 ng/ml to 1,000,000 ng/ml, and then putting the RLU1 of the analyte into a corresponding calibration curve.

As can be seen in Table 12, when the concentration of HFP is 10,000 ng/ml, the signal value reaches to its peak, and the corresponding growth rate A is 18%. If the growth rate with respect to the analyte is smaller than 18%, it is determined that the sample is not an HD-Hook-effect sample, and its concentration is calculated by putting its RLU1 into a section of the calibration curve where a concentration is smaller than 10,000 ng/ml. If the growth rate with respect to the analyte is larger than or equal to 18%, it is determined that the sample is an HD-Hook-effect sample, and its concentration is calculated by putting its RLU1 into a section of the calibration curve where a concentration is larger than 10,000 ng/ml. By way of this, the upper limit of the detection range is increased from 10,000 ng/ml to 1,000,000 ng/ml.

Example 11: Detection of Thyroid Stimulating Hormone (TSH) in a Sample

Thyroid stimulating hormone (TSH) detection reagent kit (chemiluminescence) purchased from Shanghai Beyond Biotech Co., Ltd was used to measure a concentration of AFP (purchased from Fitzgerald, Catalog No: 30R-AT009) in a sample.

Gradient dilution was performed on high-concentration TSH. Signal values of samples having different concentrations of TSH were detected by a conventional method and by a method of the present disclosure, respectively. Reference is made to Example 8 for description of the conventional detection method and the method of the present disclosure. Results of the detections were shown in Table 13.

TABLE 11

Results of conventional detection and detection by the method of the present disclosure

| Concentration (μIU/ml) | Conventional detection results RLU | Detection results by method of the present discolsure | | |
|---|---|---|---|---|
| | | RLU1 | RLU2 | Growth Rate A |
| 1 | 1103 | 945 | 907 | −4.0% |
| 3 | 2575 | 2164 | 2094 | −3.2% |
| 10 | 7819 | 6599 | 6531 | −1.0% |
| 33 | 21753 | 18402 | 18769 | 2.0% |
| 100 | 72245 | 56936 | 58935 | 3.5% |
| 335 | 211059 | 165014 | 179901 | 9.0% |
| 1,000 | 544987 | 431178 | 483676 | 12.2% |
| 3,350 | 927996 | 766522 | 887819 | 15.8% |
| 10,000 | 1105743 | 935888 | 1095402 | 17.0% |
| 33,500 | 1076776 | 908019 | 1069339 | 17.8% |
| 100,000 | 947465 | 759085 | 899887 | 18.5% |
| 335,000 | 584210 | 471532 | 563676 | 19.5% |
| 1,000,000 | 303719 | 249043 | 301106 | 20.9% |

Figure 22:
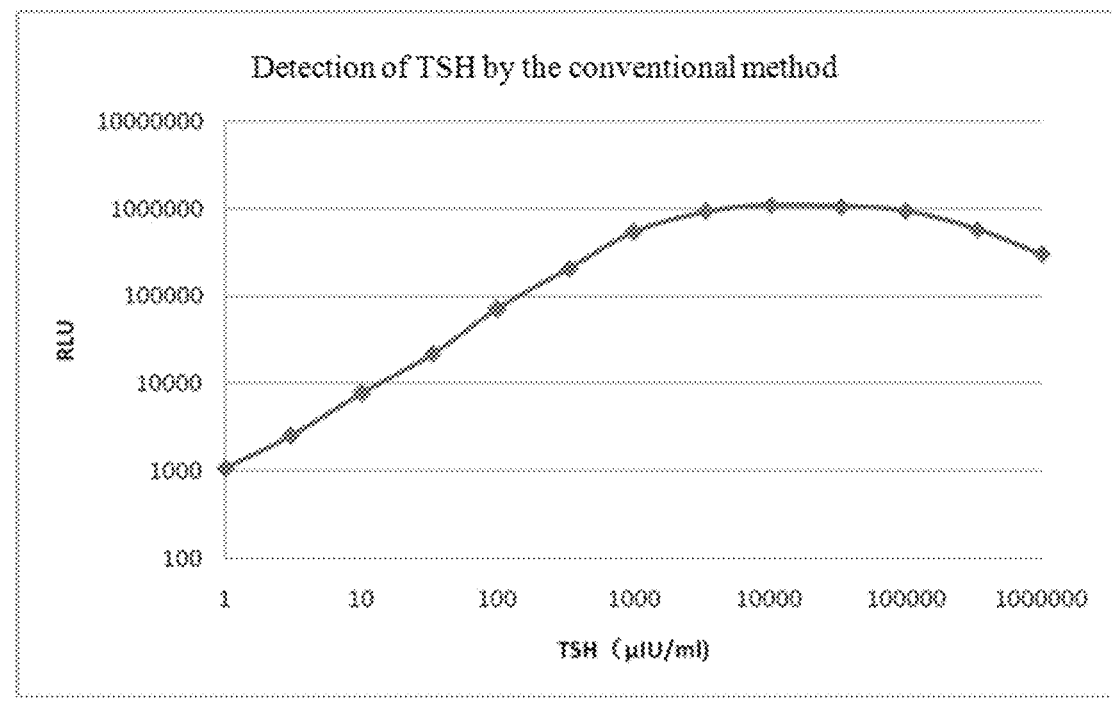
FIG. 22 is a curve showing a relationship between a signal value and a sample concentration in detection of TSH by a conventional method.

As can be seen from Table 13 and FIG. 22, as the concentration increases from 1 μIU/ml to 10000 μIU/ml, the signal value increases with the increase of the concentration. As the concentration continues to increase, the signal value decreases with the increase of the concentration of TSH. That is to say, when the concentration is larger than 10,000 μIU/ml, HD-Hook effect occurs. In a conventional detection, a sample with an antigen concentration larger than such a detection range would be detected as a sample with a low antigen concentration (the detected concentration would be smaller than 10,000 μIU/ml).

The method of the present disclosure, by means of two times of value reading, expands the detection range. Each sample is detected for two times to obtain two signal values RLU1 and RLU2. A growth rate A from the first-time-read-value to the second-time-read-value calculated based on the equation $A=(RLU2/RLU1-1)\times 100\%$ is used as an index for determining a concentration range of a sample. As can be seen from Table 12 and FIG. 21, the signal value continuously increases with the increase of the concentration before the concentration increases to 10,000 ng/ml, after that, the signal value starts to decrease with the increase of the concentration, but the growth rate A increases continuously with the increase of the concentration.

Figure 23:
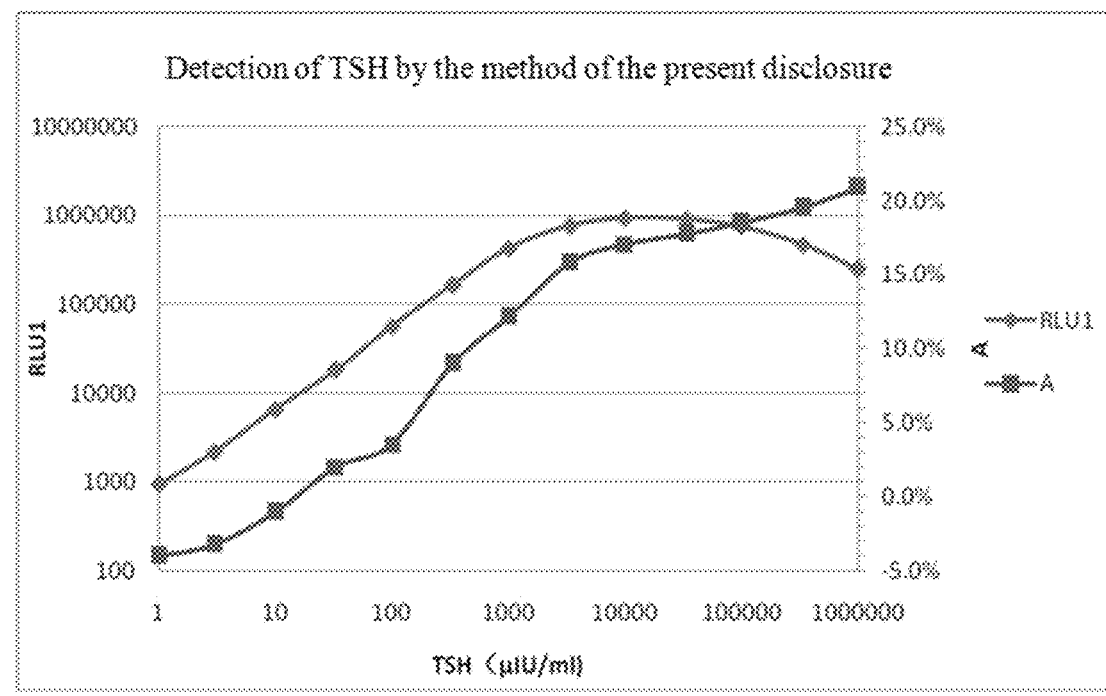
FIG. 23 is a curve showing a relationship between a first-time-read-value and a sample concentration and a relationship between a growth rate A and the sample concentration in detection of TSH by a method of the present disclosure.

When concentrations of TSH calibrators range from 1 μIU/ml to 1,000,000 μIU/ml, the method of the present disclosure is adopted to draw a calibration curve and a standard curve respectively based on R1U1 and growth rate A (as shown in FIG. 23). With the increase of the concentration, the growth rate A continuously increases. The curve of RLU1 consists of a rising section from 1 μIU/ml to 10,000 μIU/ml and a dropping section from 10,000 μIU/ml to 1,000,000 μIU/ml. RLU1, RLU2, and growth rate A with respect to the sample to be detected are obtained by the method of the present disclosure. A concentration of the analyte can be calculated by first determining, based on the growth rate A, whether the concentration of the analyte is located in the rising section 1 μIU/ml to 10,000 μIU/ml in the dropping section from 10,000 μIU/ml to 1,000,000 μIU/ml, and then putting the RLU1 of the analyte into a corresponding calibration curve.

As can be seen in Table 13, when the concentration of TSH is 10,000 μIU/ml, the signal value reaches to its peak, and the corresponding growth rate A is 17.0%. If the growth rate with respect to the analyte is smaller than 17.0%, it is determined that the sample is not an HD-Hook-effect sample, and its concentration is calculated by putting its RLU1 into a section of the calibration curve where a concentration is smaller than 10,000 μIU/ml. If the growth rate with respect to the analyte is larger than or equal to 17.0%, it is determined that the sample is an HD-Hook-effect sample, and its concentration is calculated by putting its RLU1 into a section of the calibration curve where a concentration is larger than 10,000 μIU/ml. By way of this, the upper limit of the detection range is increased from 10,000 μIU/ml to 1,000,000 μIU/ml.

Example 12: Detection of Hepatitis B Virus Surface Antigen (HBsAg) in Human Serum Samples A reagent kit related to an immunoassay method of the present disclosure was used to measure a concentration of HBsAg in a sample. The reagent kit included: calibrators 1 to 6, a peak-value calibrator, a reagent 1 (which was a light-emitting antibody, namely light-emitting particles coated with an antibody), and a reagent 2 (which was a biotin-labeled antibody, namely an antibody labeled with biotin).

Calibrators 1 to 6: samples from routine reagent kits each with a known concentration that was much smaller than a concentration of an HD-Hook-effect sample. The calibrators were used to plot a calibration curve for calculation of a concentration of an analyte.

Selection of the peak-value calibrator: Gradient dilution was performed on a known HD-Hook-effect sample. Signal values with respect to the diluted samples were detected by a conventional method. A sample having a largest signal value was selected as the peak-value calibrator. Samples with concentrations smaller than a concentration of the peak-value calibrator would not suffer from HD-Hook effect, but samples with concentrations larger than the concentration of the peak-value calibrator would suffer from HD-Hook effect. A growth rate A with respect to the peak calibrator was marked as R0 and was taken as a critical value used to determine whether a sample to be detected was an HD-Hook-effect sample.

Other components used: LiCA general-purpose solution (light-sensitive particles labeled with streptavidin) which is an auxiliary reagent produced by Beyond Biotech Co., Ltd for a light initiated chemiluminescent assay system, and was used together with an apparatus and a corresponding light initiated chemiluminescence detection reagent kit to detect an antigen or antibody.

Calibrators 1 to 6, a peak-value calibrator, and serum samples 1 to 15 to be detected were detected using the method of the present disclosure. Specifically, an analyte, a reagent 1 (light-emitting particles coated with an antibody), and a reagent 2 (a biotin-labeled antibody) were added into a reaction vessel to form a mixture. The mixture was then incubated at 37° C. for 15 min, followed by addition of a general-purpose solution (light-sensitive particles labeled with streptavidin) and incubation at 37° C. for 3 min, and a signal value RLU1 was read. After that, the mixture was incubated again at 37° C. for 7 min, and a signal value RLU2 was read. A growth rate from the first-time-read-value RLU1 to the second-time-read-value RLU2 was calculated based on equation $A=(RLU2/RLU1-1)\times 100\%$. Results were shown in Table 14.

TABLE 14

Detection resutls by the method of the present disclosure

|  | Smaples | RLU (1) | RLU (2) | Growht rate A | Concentration IU/ml |
|---|---|---|---|---|---|
| Calibrators | Calibrator 1 | 422 | 480 | 14% | 0.00 |
|  | Calibrator 2 | 837 | 963 | 15% | 0.10 |
|  | Calibrator 3 | 1810 | 2178 | 20% | 0.90 |
|  | Calibrator 4 | 36396 | 45223 | 24% | 27.56 |
|  | Calibrator 5 | 200089 | 250799 | 25% | 156.46 |
|  | Calibrator 6 | 396371 | 502928 | 27% | 336.56 |
|  | Peak-value calibrator | 1067534 | 1393208 | 31% |  |
| Samples to be detected | Sample 1 | 144451 | 202472 | 40% | HOOK |
|  | Sample 2 | 145010 | 206857 | 43% | HOOK |
|  | Sample 3 | 232678 | 318684 | 37% | HOOK |
|  | Sample 4 | 415121 | 534674 | 29% | 368.29 |
|  | Sample 5 | 349098 | 468840 | 34% | HOOK |
|  | Sample 6 | 83799 | 123879 | 48% | HOOK |
|  | Sample 7 | 171530 | 211953 | 24% | 137.07 |
|  | Sample 8 | 199010 | 251351 | 26% | 159.34 |
|  | Sample 9 | 375057 | 498512 | 33% | HOOK |
|  | Sample 10 | 325790 | 409503 | 26% | 250.82 |
|  | Sample 11 | 225486 | 282838 | 25% | 188.59 |
|  | Sample 12 | 97703 | 141949 | 45% | HOOK |

TABLE 14-continued

Detection resutls by the method of the present disclosure

| Smaples | RLU (1) | RLU (2) | Growht rate A | Concentration IU/ml |
|---|---|---|---|---|
| Sample 13 | 103552 | 150462 | 45% | HOOK |
| Sample 14 | 193000 | 263358 | 36% | HOOK |
| Sample 15 | 280822 | 370651 | 32% | HOOK |

Concentrations of serum samples 1 to 15 detected by the method of the present disclosure were shown in Table 14. HD-Hook-effect samples were firstly determined by comparing growth rates with respect to these samples with the growth rate R0 with respect to the peak-value calibrator. In other words, samples each with a growth rate A that was larger than 31% were determined as HD-Hook-effect samples which should be diluted before detection. Samples each with a growth rate A that was smaller than 31% were not HD-Hook-effect samples, and concentrations thereof could be calculated using a calibration curve.

Reliability of the above results was verified by gradiently diluting the samples and then detecting concentrations thereof. Specifically, two-fold dilution and four-fold dilution were performed on samples 1 to 15, and then a conventional detection method was used to detect the undiluted original samples, the samples after two-fold dilution, and the samples after four-fold dilution. By observing variations of the concentrations of the samples, it was determined whether a sample was an HD-Hook-effect sample or not. If a sample had an increased concentration after it was diluted, it was determined that the sample was an HD-Hook-effect sample. If a sample had a decreased concentration after it was diluted, it was determined that the sample was not an HD-Hook-effect sample. Results were shown in Table 15.

TABLE 15

Verification results after sample dilution

| Samples diluted and verified | Undiluted original samples | Samples after two-fold dilution | Samples after four-fold dilution | Concentrations IU/mL |
|---|---|---|---|---|
| Sample 1 | 128.79 | 262.17 | 474.22 | HOOK |
| Sample 2 | 135.81 | 249.87 | 417.08 | HOOK |
| Sample 3 | 228.96 | 388.23 | 642.69 | HOOK |
| Sample 4 | 369.11 | 222.22 | 124.14 | 369.11 |
| Sample 5 | 353.47 | 618.94 | 886.34 | HOOK |
| Sample 6 | 74.52 | 132.14 | 226.20 | HOOK |
| Sample 7 | 134.44 | 60.89 | 31.22 | 134.44 |
| Sample 8 | 154.76 | 72.45 | 36.50 | 154.76 |
| Sample 9 | 331.50 | 546.11 | 881.46 | HOOK |
| Sample 10 | 260.78 | 104.97 | 49.26 | 260.78 |
| Sample 11 | 174.00 | 97.86 | 51.41 | 174.00 |
| Sample 12 | 82.80 | 176.16 | 328.03 | HOOK |
| Sample 13 | 94.92 | 192.47 | 367.37 | HOOK |
| Sample 14 | 158.96 | 277.50 | 434.39 | HOOK |
| Sample 15 | 269.64 | 480.82 | 814.12 | HOOK |

As can be seen from Table 15, serum samples 1, 2, 3, 5, 6, 9, 12, 13, 14, and 15 are detected to have increased concentrations after they are diluted. This shows that these samples are HD-Hook-effect samples. Serum samples 4, 7, 8, 10, and 11 are detected to have reduced concentrations after they are diluted, which shows that these samples are not HD-Hook-effect samples. These results are consistent with those detected by the method of the present disclosure.

Example 13: Detection of CA125 in Human Serum Samples

A reagent kit related to an immunoassay method of the present disclosure was used to measure a concentration of CA125 in a sample. The reagent kit included: calibrators 1 to 6, a peak-value calibrator, a reagent 1 (which was a light-emitting antibody, namely light-emitting particles coated with an antibody), and a reagent 2 (which was a biotin-labeled antibody, namely an antibody labeled with biotin).

Calibrators 1 to 6: samples from routine reagent kits each with a known concentration that was much smaller than a concentration of an HD-Hook-effect sample. The calibrators were used to plot a calibration curve for calculation of a concentration of an analyte.

Selection of the peak-value calibrator: Gradient dilution was performed on a known HD-Hook-effect sample. Signal values with respect to the diluted samples were detected by a conventional method. A sample having a largest signal value was selected as the peak-value calibrator. Samples with concentrations smaller than a concentration of the peak-value calibrator would not suffer from HD-Hook effect, but samples with concentrations larger than the concentration of the peak-value calibrator would suffer from HD-Hook effect. A growth rate A with respect to the peak-value calibrator was marked as R0 and was taken as a critical value used to determine whether a sample to be detected was an HD-Hook-effect sample.

Calibrators 1 to 6, a peak-value calibrator, and serum samples 1 to 18 to be detected were detected using the method of the present disclosure. Specifically, an analyte, a reagent 1 (light-emitting particles coated with an antibody), and a reagent 2 (a biotin-labeled antibody) were added into a reaction vessel to form a mixture. The mixture was then incubated at 37° C. for 15 min, followed by addition of a general-purpose solution (light-sensitive particles labeled with streptavidin) and incubation at 37° C. for 3 min, and a signal value RLU1 was read. After that, the mixture was incubated again at 37° C. for 7 min, and a signal value RLU2 was read. A growth rate from the first-time-read-value RLU1 to the second-time-read-value RLU2 was calculated based on equation $A=(RLU2/RLU1-1)\times 100\%$. Results were shown in Table 16.

TABLE 16

Detection resutls by the method of the present disclosure

| | Smaples | RLU (1) | RLU (2) | Growth rate A | Concentration U/ml |
|---|---|---|---|---|---|
| Calibtrators | Calibrator 1 | 999 | 744 | −25.5% | 0 |
| | Calibrator 2 | 10857 | 8248 | −24.0% | 9.17 |
| | Calibrator 3 | 21563 | 17508 | −18.8% | 19.11 |
| | Calibrator 4 | 102708 | 88869 | −13.5% | 87.53 |
| | Calibrator 5 | 271593 | 259355 | −4.5% | 251.58 |
| | Calibrator 6 | 794718 | 853603 | 7.4% | 1043.74 |
| | Peak-value calibrator | 2537830 | 3012939 | 18.7% | |
| Samples to be detected | Sample 1 | 9665 | 7217 | −25.3% | 8.06 |
| | Sample 2 | 16130 | 12287 | −23.8% | 14.09 |
| | Sample 3 | 51059 | 42166 | −17.4% | 44.79 |
| | Sample 4 | 71055 | 59021 | −16.9% | 61.36 |
| | Sample 5 | 92952 | 80019 | −13.9% | 79.39 |
| | Sample 6 | 196716 | 178735 | −9.1% | 173.32 |
| | Sample 7 | 225436 | 213141 | −5.5% | 202.34 |
| | Sample 8 | 290252 | 281001 | −3.2% | 272.3 |
| | Sample 9 | 340529 | 345889 | 1.6% | 330.44 |
| | Sample 10 | 465955 | 478028 | 2.6% | 492.14 |

TABLE 16-continued

Detection resutls by the method of the present disclosure

| Smaples | RLU (1) | RLU (2) | Growth rate A | Concentration U/ml |
|---|---|---|---|---|
| Sample 11 | 513321 | 530012 | 3.3% | 560.23 |
| Sample 12 | 711508 | 760017 | 6.8% | 889.7 |
| Sample 13 | 908842 | 973276 | 7.1% | >1000.00 |
| Sample 14 | 1845773 | 2103378 | 14.0% | >1000.00 |
| Sample 15 | 2390350 | 2772269 | 16.0% | >1000.00 |
| Sample 16 | 688606 | 859340 | 24.8% | HOOK |
| Sample 17 | 560058 | 709209 | 26.6% | HOOK |
| Sample 18 | 453979 | 584179 | 28.7% | HOOK |

Concentrations of serum samples 1 to 18 detected by the method of the present disclosure were shown in Table 16. HD-Hook-effect samples were firstly determined by comparing growth rates with respect to these samples with the growth rate R0 with respect to the peak-value calibrator. In other words, samples each with a growth rate A that was larger than 18.7% were determined as HD-Hook-effect samples which should be diluted before detection. Samples each with a growth rate A that was smaller than 18.7% were not HD-Hook-effect samples, and concentrations thereof could be calculated directly using a calibration curve.

Reliability of the above results was verified by gradiently diluting the samples and then detecting concentrations thereof. Specifically, two-fold dilution and four-fold dilution were performed on samples 1 to 18, and then a conventional detection method was used to detect the undiluted original samples, the samples after two-fold dilution, and the samples after four-fold dilution. By observing variations of the concentrations of the samples, it was determined whether a sample was an HD-Hook-effect sample or not. If a sample had an increased concentration after it was diluted, it was determined that the sample was an HD-Hook-effect sample. If a sample had a decreased concentration after it was diluted, it was determined that the sample was not an HD-Hook-effect sample. Results were shown in Table 17.

TABLE 17

Verification results after sample dilution

| Samples diluted and verified | Detected concentrations | | | Concentration U/mL |
|---|---|---|---|---|
| | Undiluted original samples | Samples after two-fold dilution | Samples after four-fold dilution | |
| Sample 1 | 8.02 | 4.36 | 2.26 | 8.02 |
| Sample 2 | 13.42 | 7.21 | 3.32 | 13.42 |
| Sample 3 | 47.14 | 25.17 | 11.8 | 47.14 |
| Sample 4 | 66.49 | 30.09 | 16.19 | 66.49 |
| Sample 5 | 80.84 | 44.42 | 20.86 | 80.84 |
| Sample 6 | 167.73 | 81.77 | 41.22 | 167.73 |
| Sample 7 | 192.31 | 101.89 | 49.65 | 192.31 |
| Sample 8 | 300.92 | 154.39 | 78.77 | 300.92 |
| Sample 9 | 352.65 | 170.05 | 87.05 | 352.65 |
| Sample 10 | 528.74 | 260.36 | 127.31 | 528.74 |
| Sample 11 | 612.44 | 299.05 | 141.28 | 612.44 |
| Sample 12 | 901.35 | 447.07 | 213.5 | 901.35 |
| Sample 13 | >1000.00 | 559.3 | 258.1 | >1000.00 |
| Sample 14 | >1000.00 | >1000.00 | 551.3 | >1000.00 |
| Sample 15 | >1000.00 | >1000.00 | 771.9 | >1000.00 |
| Sample 16 | 830.97 | 992.82 | >1000.00 | HOOK |
| Sample 17 | 734.25 | 934.91 | >1000.00 | HOOK |
| Sample 18 | 550.42 | 778.12 | >1000.00 | HOOK |

As can be seen from Table 17, serum samples 16, 17, and 18 are detected to have increased concentrations after they are diluted. This shows that these samples are HD-Hook-effect samples. Serum samples 1 to 15 are detected to have reduced concentrations after they are diluted, which shows that these samples are not HD-Hook-effect samples. These results are consistent with those detected by the method of the present disclosure.

Example 14: Detection of Ferritin (Ferr) in Human Serum Samples

A reagent kit related to an immunoassay method of the present disclosure was used to measure a concentration of Ferr (purchased from Fitzgerald, Catalog No:30-AF10) in a sample. The reagent kit included: calibrators 1 to 6, a peak-value calibrator, a reagent 1 (which was a light-emitting antibody, namely light-emitting particles coated with an antibody), and a reagent 2 (which was a biotin-labeled antibody, namely an antibody labeled with biotin).

Calibrators 1 to 6: samples from routine reagent kits each with a known concentration that was much smaller than a concentration of an HD-Hook-effect sample. The calibrators were used to plot a calibration curve for calculation of a concentration of an analyte.

Selection of the peak-value calibrator: Gradient dilution was performed on a known HD-Hook-effect sample. Signal values with respect to the diluted samples were detected by a conventional method. A sample having a largest signal value (which was sample 9 in this detection) was selected as the peak-value calibrator. Samples with concentrations smaller than a concentration of the peak-value calibrator would not suffer from HD-Hook effect, but samples with concentrations larger than the concentration of the peak-value calibrator would suffer from HD-Hook effect. A growth rate A with respect to the peak-value calibrator was marked as R0 and was taken as a critical value used to determine whether a sample to be detected was an HD-Hook-effect sample.

Gradient dilution was performed on a high-concentration ferr antigen. Concentrations of samples having different concentrations of ferr were detected by a conventional method and by a method of the present disclosure, respectively.

Detection by the Conventional Method:

Calibrators 1 to 6, a peak-value calibrator or samples to be detected 1 to 15, a reagent 1 (which was a light-emitting antibody, namely light-emitting particles coated with a mouse monoclonal antibody), and a reagent 2 (a biotin-labeled antibody, namely a mouse monoclonal antibody labeled with biotin) were added into a reaction vessel to form a mixture. The mixture was then incubated at 37° C. for 15 min, followed by addition of a general-purpose solution (light-sensitive particles labeled with streptavidin) and incubation at 37° C. for 10 min. A photon counter was used to read a signal value which was marked as RLU. Results were shown in Table 18.

Detection by a two-time-value-reading method of the present disclosure:

Calibrators 1 to 6, a peak-value calibrator or samples to be detected 1 to 15, a reagent 1 (which was a light-emitting antibody, namely light-emitting particles coated with a mouse monoclonal antibody), and a reagent 2 (a biotin-labeled antibody, namely a mouse monoclonal antibody labeled with biotin) were added into a reaction vessel to form a mixture. The mixture was then incubated at 37° C. for 15 min, followed by addition of a general-purpose solution (light-sensitive particles labeled with streptavidin) and incubation at 37° C. for 3 min, and a signal value RLU1 was read. After that, the mixture was incubated again at 37° C. for 7 min, and a signal value RLU2 was read. A growth rate from the first-time-read-value RLU1 to the second-time-read-value RLU2 was calculated based on equation $A=(RLU2/RLU1-1)\times 100\%$. Results were shown in Table 18.

TABLE 18

Results of conventional detection and detection by the method of the present disclosure

|  | Samples | Real concentration Concentration ng/ml | Conventional detection results RLU | Conventional detection results Concentration ng/ml | Detection results by method of the present discolsure RLU (1) | Detection results by method of the present discolsure RLU (2) | Detection results by method of the present discolsure Growth rate A | Detection results by method of the present discolsure Concentration ng/ml |
|---|---|---|---|---|---|---|---|---|
| Calibrators | Calibrator 1 | 0 | 1504 | 0 | 1301 | 982 | −24.5% | 0 |
|  | Calibrator 2 | 19.91 | 9470 | 19.91 | 8419 | 5699 | −32.3% | 19.91 |
|  | Calibrator 3 | 101.02 | 46702 | 101.02 | 39701 | 31854 | −19.8% | 101.02 |
|  | Calibrator 4 | 502.74 | 201992 | 502.74 | 177904 | 152780 | −14.1% | 502.74 |
|  | Calibrator 5 | 994.36 | 382044 | 994.36 | 336189 | 299061 | −11.0% | 994.36 |
|  | Calibrator 6 | 2232.94 | 745316 | 2232.94 | 701657 | 662840 | −5.5% | 2232.94 |
|  | Peak calibtrator (sample 9) | 51000 | 2378260 | 51000 | 2113558 | 2407210 | 13.9% | 51000 |
| Smaples to be detected | Sample 1 | 20 | 10008 | 21.21 | 9010 | 6256 | −30.6% | 21.53 |
|  | Sample 2 | 200 | 83614 | 184.44 | 75542 | 63340 | −16.2% | 196.81 |
|  | Sample 3 | 2000 | 688675 | >2000 | 635950 | 595131 | −6.4% | >2000 |
|  | Sample 4 | 5100 | 1131402 | >2000 | 1083169 | 1077907 | −0.5% | >2000 |
|  | Sample 5 | 10200 | 1684984 | >2000 | 1448123 | 1526161 | 5.4% | >2000 |
|  | Sample 6 | 15300 | 1966033 | >2000 | 1776540 | 1926924 | 8.5% | >2000 |
|  | Sample 7 | 20400 | 2132659 | >2000 | 1907869 | 2132148 | 11.8% | >2000 |
|  | Sample 8 | 25500 | 2288952 | >2000 | 1999686 | 2251677 | 12.6% | >2000 |
|  | Sample 9 | 51000 | 2378260 | >2000 | 2113558 | 2407210 | 13.9% | >2000 |

TABLE 18-continued

Results of conventional detection and detection by the method of the present disclosure

| | Real concentration | Conventional detection results | | Detection results by method of the present discolsure | | | |
|---|---|---|---|---|---|---|---|
| Samples | Concentration ng/ml | RLU | Concentration ng/ml | RLU (1) | RLU (2) | Growth rate A | Concentration ng/ml |
| Sample 10 | 102000 | 2304238 | >2000 | 2094861 | 2392541 | 14.2% | HOOK |
| Sample 11 | 153000 | 2163232 | >2000 | 1903523 | 2210245 | 16.1% | HOOK |
| Sample 12 | 204000 | 1958628 | >2000 | 1740069 | 2031467 | 16.7% | HOOK |
| Sample 13 | 255000 | 1777808 | >2000 | 1615030 | 1899252 | 17.6% | HOOK |
| Sample 14 | 510000 | 1401282 | >2000 | 1162934 | 1398233 | 20.2% | HOOK |
| Sample 15 | 2550000 | 646266 | 1860.97 | 538637 | 668007 | 24.0% | HOOK |

Note:
A concentration range of ferr detected by a conventional method is 0-2000 ng/ml, and if the concentration exceeds an upper limit of detection, it is shown that a concentration of the sample is larger than 2000 ng/ml.

Figure 24:
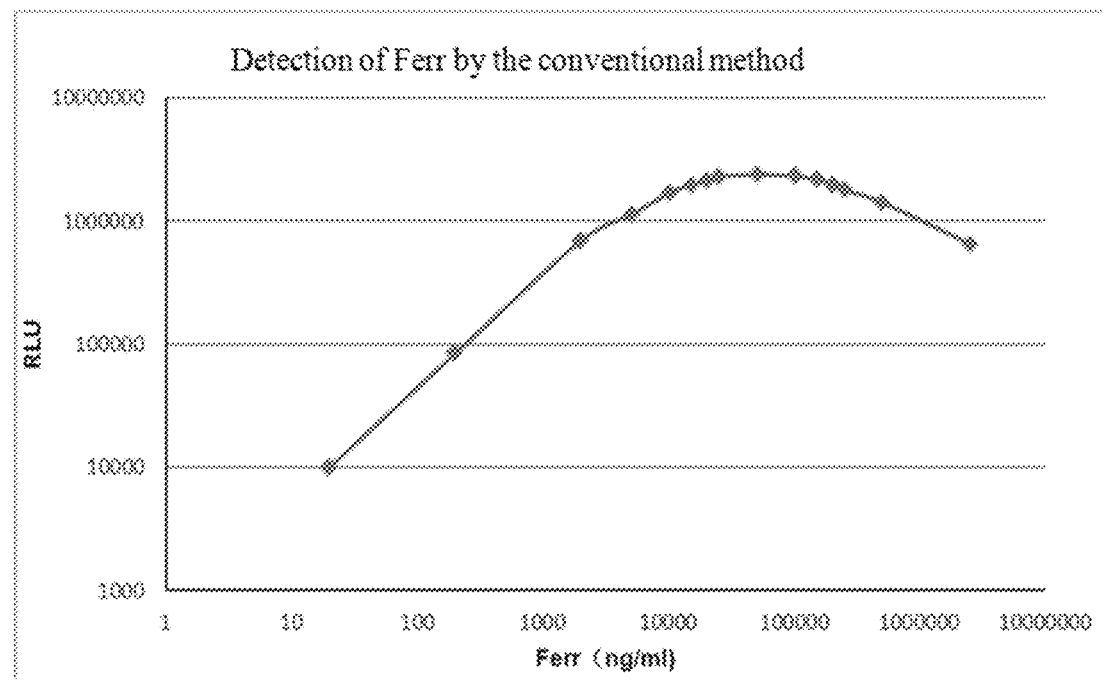
FIG. 24 is a curve showing a relationship between a signal value and a sample concentration in detection of Ferr by a conventional method.

As can be seen from Table 18 and FIG. 24, for gradiently diluted high-concentration antigen samples detected by the conventional method, before the concentration increases to 51000 ng/ml, the signal value increases with the increase of the concentration; when the concentration continues to increase, the signal value decreases with the increase of the concentration of ferr. That is to say, samples with concentrations larger than 51000 ng/ml are HD-Hook-effect samples. Sample 9 with a concentration of 51000 ng/ml is the peak-value calibrator, and R0 is 13.9%.

In the conventional detection, a concentration range detected is 0-2000 ng/ml, and if the concentration exceeds the upper limit of detection, it is shown that the concentration of the sample is larger than 2000 ng/ml. When the concentration of the HD-Hook-effect sample continues to increase and the signal value continues to decrease, a sample with a super high concentration would be detected as a sample with a low concentration, an example of which is sample 15. Therefore, in a conventional detection, it cannot be tell whether a result of the detected sample is a real concentration or a detected inaccurate low concentration caused by an effect of HD-Hook effect on the sample's super high concentration.

Figure 25:
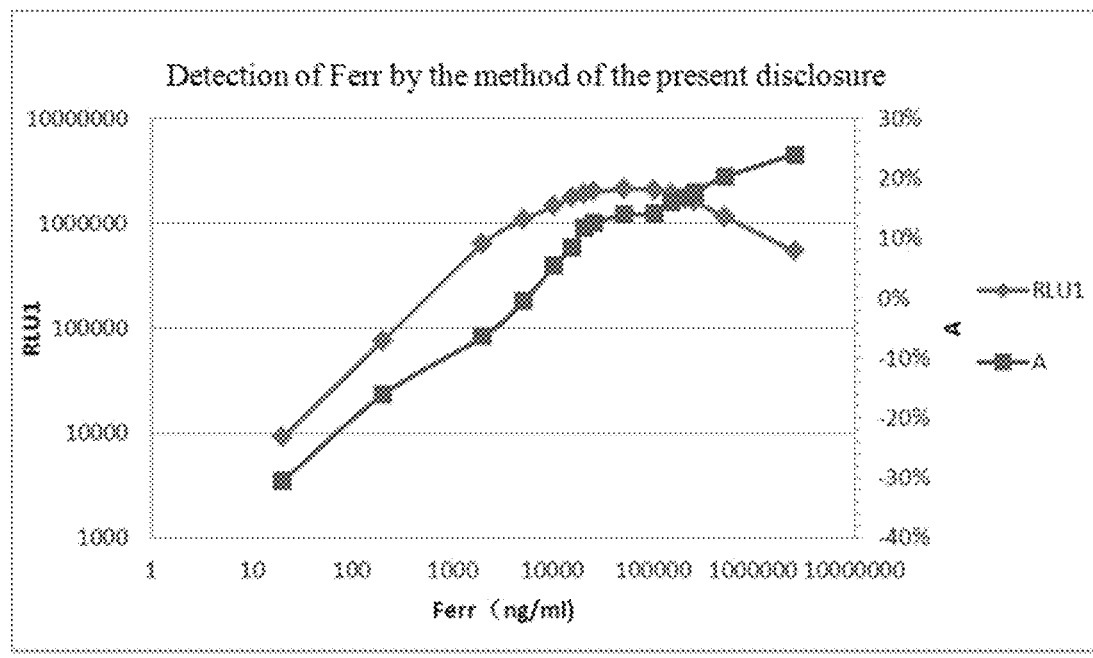
FIG. 25 is a curve showing a relationship between a first-time-read-value and a sample concentration and a relationship between a growth rate A and the sample concentration in detection of Ferr by a method of the present disclosure.

The method of the present disclosure determines an HD-Hook-effect sample by means of two times of value reading. Each sample is detected for two times to obtain two signal values RLU1 and RLU2. A growth rate A from the first-time-read-value to the second-time-read-value calculated based on the equation $A=(RLU2/RLU1-1) \times 100\%$ is used as an index for determining the concentration of the sample. As can be seen from Table 18 and FIG. 25, the signal value increases with the increase of the concentration before the concentration increases to 51000 ng/ml, and after that, the signal value decreases with the increase of the concentration but the growth rate A continues to increase with the increase of the concentration. The concentration of the sample and the concentration of the calibrator can therefore be compared with each other by directly comparing the growth rate A with respect to the sample and the growth rate A with respect to the calibrator. Growth rates A with respect to samples 10 to 15 are all larger than the growth rate R0 with respect the peak-value calibrator (13.9%). This shows that concentrations of Ferr in samples 10 to 15 are all larger than 51000 ng/ml and therefore samples 10 to 15 are HD-Hook-effect samples. This is consistent with the real concentrations. The signal value of sample 15 is smaller than that of calibrator 6, and a concentration of sample 15 detected by the conventional method is 1860.97 ng/ml. It is determined by the method of the present disclosure that sample 15 is an HD-Hook-effect sample and needs to be diluted before detection.

Example 15: Detection of C-Peptide (CP) in Samples

A reagent kit related to an immunoassay method of the present disclosure was used to measure a concentration of CP (purchased from Fitzgerald, Catalog No: 30-AC96) in a sample. The reagent kit included: calibrators 1 to 6, a peak-value calibrator, a reagent 1 (which was a light-emitting antibody, namely light-emitting particles coated with an antibody), and a reagent 2 (which was a biotin-labeled antibody, namely an antibody labeled with biotin).

Calibrators 1 to 6: samples from routine reagent kits each with a known concentration that was much smaller than a concentration of an HD-Hook-effect sample. The calibrators were used to plot a calibration curve for calculation of a concentration of an analyte.

Selection of the peak-value calibrator: Gradient dilution was performed on a known HD-Hook-effect sample. Signal values with respect to the diluted samples were detected by a conventional method. A sample having a largest signal value (which was sample 9 in this detection) was selected as the peak-value calibrator. Samples with concentrations smaller than a concentration of the peak-value calibrator would not suffer from HD-Hook effect, but samples with concentrations larger than the concentration of the peak-value calibrator would suffer from HD-Hook effect. A growth rate A with respect to the peak-value calibrator was marked as R0 and was taken as a critical value used to determine whether a sample to be detected was an HD-Hook-effect sample.

Gradient dilution was performed on a high-concentration CP antigen. Concentrations of samples having different concentrations of ferr were detected by a conventional method and by a method of the present disclosure, respectively.

Detection by the Conventional Method:

Calibrators 1 to 6, a peak-value calibrator or samples to be detected 1 to 15, a reagent 1 (which was a light-emitting antibody, namely light-emitting particles coated with a mouse monoclonal antibody), and a reagent 2 (a biotin-labeled antibody, namely a mouse monoclonal antibody labeled with biotin) were added into a reaction vessel to form a mixture. The mixture was then incubated at 37° C. for 15 min, followed by addition of a general-purpose solution (light-sensitive particles labeled with streptavidin) and incubation at 37° C. for 10 min. A photon counter was used to read a signal value which was marked as RLU. Results were shown in Table 19.

Detection by a two-time-value-reading method of the present disclosure:

Calibrators 1 to 6, a peak-value calibrator or samples to be detected 1 to 15, a reagent 1 (which was a light-emitting antibody, namely light-emitting particles coated with a mouse monoclonal antibody), and a reagent 2 (a biotin-labeled antibody, namely a mouse monoclonal antibody labeled with biotin) were added into a reaction vessel to form a mixture. The mixture was then incubated at 37° C. for 15 min, followed by addition of a general-purpose solution (light-sensitive particles labeled with streptavidin) and incubation at 37° C. for 3 min, and a signal value RLU1 was read. After that, the mixture was incubated again at 37° C. for 7 min, and a signal value RLU2 was read. A growth rate from the first-time-read-value RLU1 to the second-time-read-value RLU2 was calculated based on equation A=(RLU2/RLU1−1)×100%. Results were shown in Table 19.

the sample is larger than 30 ng/ml. When the concentration of the HD-Hook-effect sample continues to increase and the signal value continues to decrease, a sample with a super high concentration would be detected as a sample with a low concentration, examples of which are samples 16 and 17. Therefore, in a conventional detection, it cannot be tell whether a result of the detected sample is a real concentration or a detected inaccurate low concentration caused by an effect of HD-Hook effect on the sample's super high concentration.

Example 16: Detection of Hepatitis B Virus Surface Antibody (HBsAb) in Samples

A reagent kit related to an immunoassay method of the present disclosure was used to measure a concentration of HBsAb (purchased from Beijing Genstars Biotech Co., Ltd, Clone No: M2201) in a sample. The reagent kit included: calibrators 1 to 6, a peak-value calibrator, a reagent 1 (which was a light-emitting antibody, namely light-emitting par-

TABLE 19

Results of conventional detection and detection by the method of the present disclosure

| | | Real concentrations | Conventional detection results | | Detection results by method of the present discolsure | | | |
|---|---|---|---|---|---|---|---|---|
| | Samples | Concentration ng/ml | RLU | Concentration ng/ml | RLU (1) | RLU (2) | Growth rate A | Concentration ng/ml |
| Calibrators | Calibrator 1 | 0 | 304 | 0 | 302 | 331 | 9.6% | 0 |
| | Calibrator 2 | 0.59 | 2035 | 0.59 | 1778 | 1308 | −26.4% | 0.59 |
| | Calibrator 3 | 0.85 | 2539 | 0.85 | 2625 | 2016 | −23.2% | 0.85 |
| | Calibrator 4 | 6.02 | 11619 | 6.02 | 9717 | 8017 | −17.5% | 6.02 |
| | Calibrator 5 | 12.05 | 23261 | 12.05 | 21432 | 18465 | −13.8% | 12.05 |
| | Calibrator 6 | 33.31 | 55424 | 33.31 | 47809 | 45456 | −4.9% | 33.31 |
| | Peak calibtrator (sample 9) | 10000 | 3170807 | >30 | 2669419 | 3292270 | 23.3% | >30 |
| Samples to be detected | Sample 1 | 1 | 2912 | 1.06 | 2900 | 2251 | −22.4% | 0.93 |
| | Sample 2 | 3 | 6499 | 3.12 | 5729 | 4545 | −20.7% | 2.37 |
| | Sample 3 | 10 | 20345 | 10.54 | 16747 | 13986 | −16.5% | 10.13 |
| | Sample 4 | 33 | 56700 | >30 | 44852 | 42492 | −5.3% | >30 |
| | Sample 5 | 100 | 162356 | >30 | 132253 | 139349 | 5.4% | >30 |
| | Sample 6 | 335 | 435784 | >30 | 359060 | 409421 | 14.0% | >30 |
| | Sample 7 | 1000 | 1458246 | >30 | 1147167 | 1367003 | 19.2% | >30 |
| | Sample 8 | 3350 | 2610397 | >30 | 2305534 | 2785700 | 20.8% | >30 |
| | Sample 9 | 10000 | 3170807 | >30 | 2669419 | 3292270 | 23.3% | >30 |
| | Sample 10 | 33500 | 2998354 | >30 | 2376362 | 2986650 | 25.7% | HOOK |
| | Sample 11 | 100000 | 2165769 | >30 | 1717649 | 2233121 | 30.0% | HOOK |
| | Sample 12 | 335000 | 946947 | >30 | 742994 | 981144 | 32.1% | HOOK |
| | Sample 13 | 1000000 | 363059 | >30 | 297572 | 398779 | 34.0% | HOOK |
| | Sample 14 | 3350000 | 162871 | >30 | 135756 | 184090 | 35.6% | HOOK |
| | Sample 15 | 10000000 | 58143 | >30 | 46580 | 64473 | 38.4% | HOOK |
| | Sample 16 | 33500000 | 15674 | 8.15 | 12274 | 17359 | 41.4% | HOOK |
| | Sample 17 | 100000000 | 2379 | 0.76 | 1902 | 2693 | 41.6% | HOOK |

Note:
A concentration range of CP detected by a conventional method is 0-30 ng/ml, and if the concentration exceeds the upper limit of detection, it is shown that the concentration of the sample is larger than 30 ng/ml.

Figure 26:
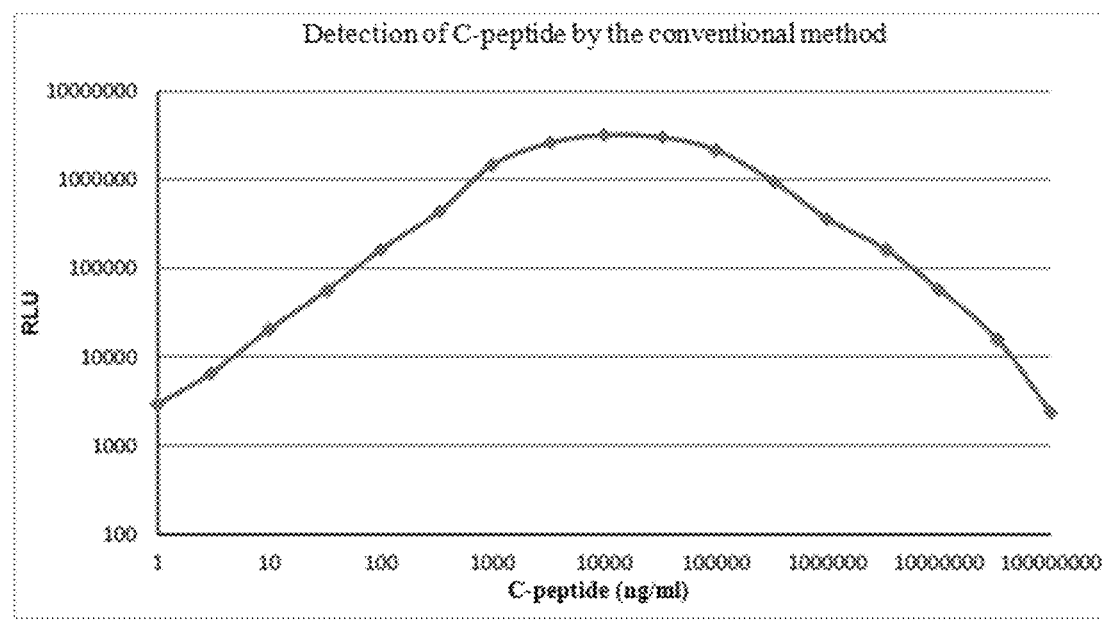
FIG. 26 is a curve showing a relationship between a signal value and a sample concentration in detection of C-peptide by a conventional method.
Figure 27:
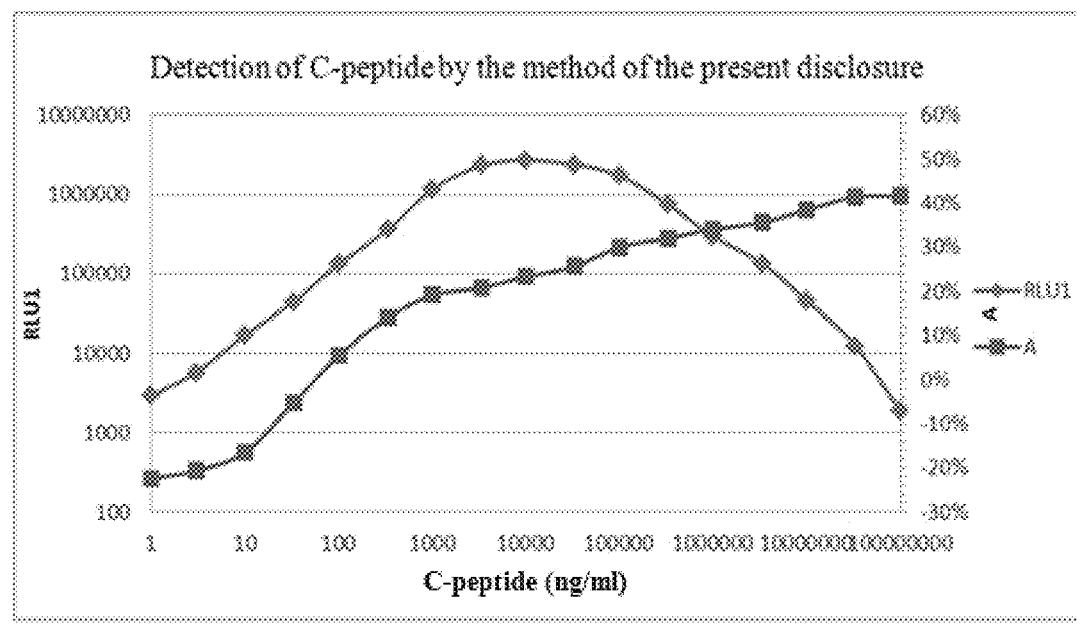
FIG. 27 is a curve showing a relationship between a first-time-read-value and a sample concentration and a relationship between a growth rate A and the sample concentration in detection of C-peptide by a method of the present disclosure.

As can be seen from Table 19 and FIG. 26, for gradiently diluted high-concentration antigen samples detected by the conventional method, before the concentration increases to 10000 ng/ml, the signal value increases with the increase of the concentration; when the concentration continues to increase, the signal value decreases with the increase of the concentration of CP. That is to say, samples with concentrations larger than 10000 ng/ml are HD-Hook-effect samples. Sample 9 with a concentration of 10000 ng/ml is the peak-value calibrator, and R0 is 23.3%.

In the conventional detection, a concentration range detected is 0-30 ng/ml, and if the concentration exceeds the upper limit of detection, it is shown that the concentration of ticles coated with an antibody), and a reagent 2 (which was a biotin-labeled antibody, namely an antibody labeled with biotin).

Calibrators 1 to 6: samples from routine reagent kits each with a known concentration that was much smaller than a concentration of an HD-Hook-effect sample. The calibrators were used to plot a calibration curve for calculation of a concentration of an analyte.

Selection of the peak-value calibrator: Gradient dilution was performed on a known HD-Hook-effect sample. Signal values with respect to the diluted samples were detected by a conventional method. A sample having a largest signal value (which was sample 9 in this detection) was selected as the peak-value calibrator. Samples with concentrations smaller than a concentration of the peak-value calibrator would not suffer from HD-Hook effect, but samples with concentrations larger than the concentration of the peak-value calibrator would suffer from HD-Hook effect. A mixture was incubated again at 37° C. for 7 min, and a signal value RLU2 was read. A growth rate from the first-time-read-value RLU1 to the second-time-read-value RLU2 was calculated based on equation $A=(RLU2/RLU1-1)\times100\%$. Results were shown in Table 20.

TABLE 20

Results of conventional detection and detection by the method of the present disclosure

| | Samples | Real concentration mIU/ml | Conventional detection results | | Detection results by method of the present discolsure | | | |
|---|---|---|---|---|---|---|---|---|
| | | | RLU | concentration mIU/ml | RLU1 | RLU2 | Growth rate A | concentration mIU/ml |
| Calibrators | Calibrator 1 | 0 | 524 | 0 | 498 | 523 | 5.0% | 0 |
| | Calibrator 2 | 10.23 | 3548 | 10.23 | 3188 | 4049 | 27.0% | 10.23 |
| | Calibrator 3 | 71.95 | 21493 | 71.95 | 17403 | 22854 | 31.3% | 71.95 |
| | Calibrator 4 | 213.65 | 64993 | 213.65 | 50526 | 67526 | 33.6% | 213.65 |
| | Calibrator 5 | 584.26 | 181544 | 584.26 | 133863 | 180954 | 35.2% | 584.26 |
| | Calibrator 6 | 1026.18 | 342125 | 1026.18 | 255651 | 347371 | 35.9% | 1026.18 |
| | Peak-value calibrator (smaple 9) | 10,000 | 1050237 | >1000 | 775542 | 1066620 | 37.5% | >1000 |
| Smaples to be detected | Sample 1 | 1 | 703 | 0.6 | 652 | 737 | 13.0% | 0.58 |
| | Sample 2 | 3 | 1257 | 2.48 | 1182 | 1424 | 20.5% | 2.58 |
| | Sample 3 | 10 | 3443 | 9.87 | 2876 | 3592 | 24.9% | 9.02 |
| | Sample 4 | 33 | 9387 | 30.24 | 7743 | 10124 | 30.8% | 28.78 |
| | Sample 5 | 100 | 31033 | 103.93 | 25555 | 33721 | 32.0% | 107.83 |
| | Sample 6 | 335 | 101781 | 332.87 | 79257 | 106917 | 34.9% | 341.56 |
| | Sample 7 | 1,000 | 341483 | >1000 | 259926 | 352344 | 35.6% | >1000 |
| | Sample 8 | 3,350 | 757906 | >1000 | 570542 | 781231 | 36.9% | >1000 |
| | Sample 9 | 10,000 | 1050237 | >1000 | 775542 | 1066620 | 37.5% | >1000 |
| | Sample 10 | 33,500 | 985422 | >1000 | 753452 | 1039798 | 38.0% | HOOK |
| | Sample 11 | 100,000 | 576535 | >1000 | 415949 | 577782 | 38.9% | HOOK |
| | Sample 12 | 335,000 | 258461 | 802.57 | 184878 | 259170 | 40.2% | HOOK |
| | Sample 13 | 1,000,000 | 107739 | 352.22 | 75811 | 109111 | 43.9% | HOOK |
| | Sample 14 | 3,350,000 | 44514 | 147.9 | 33501 | 48374 | 44.4% | HOOK |

Note:
A concentration range of HBsAb detected by a conventional method is 0-1000 mIU/ml, and if the concentration exceeds the upper limit of detection, it is shown that the concentration of the sample is larger than 1000 mIU/ml.

growth rate A with respect to the peak-value calibrator was marked as R0 and was taken as a critical value used to determine whether a sample to be detected was an HD-Hook-effect sample.

Gradient dilution was performed on a high-concentration HBsAb antigen. Concentrations of samples having different concentrations of HBsAb were detected by a conventional method and by a method of the present disclosure, respectively.

Detection by the Conventional Method:

Calibrators 1 to 6, a peak-value calibrator or samples to be detected 1 to 14, a reagent 1 (light-emitting particles coated with HBsAb), and a reagent 2 (biotin-labeled HBsAb) were added into a reaction vessel to form a mixture. The mixture was then incubated at 37° C. for 15 min, followed by addition of a general-purpose solution (light-sensitive particles labeled with streptavidin) and incubation at 37° C. for 10 min. A photon counter was used to read a signal value which was marked as RLU. Results were shown in Table 20.

Figure 28:
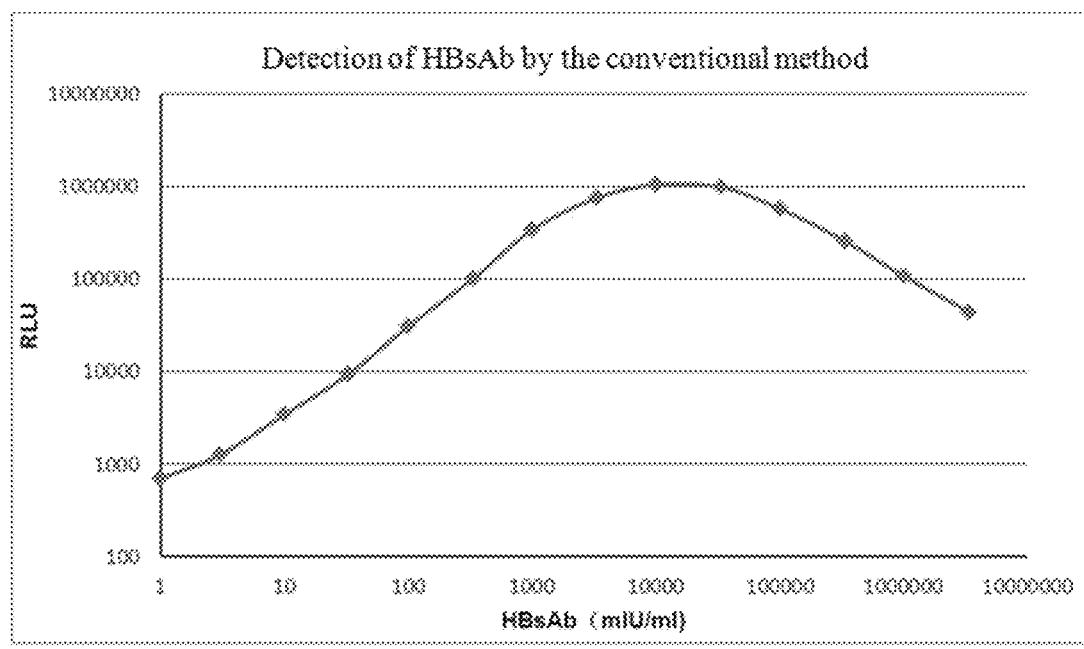
FIG. 28 is a curve showing a relationship between a signal value and a sample concentration in detection of HBsAb by a conventional method.

Detection by a two-time-value-reading method of the present disclosure:

Calibrators 1 to 6, a peak-value calibrator or samples to be detected 1 to 14, a reagent 1 (light-emitting particles coated with HBsAb), and a reagent 2 (biotin-labeled HBsAb) were added into a reaction vessel to form a mixture. The mixture was then incubated at 37° C. for 15 min, followed by addition of a general-purpose solution (light-sensitive particles labeled with streptavidin) and incubation at 37° C. for 3 min, and a signal value RLU1 was read. After that, the As can be seen from Table 20 and FIG. 28, for gradiently diluted high-concentration HBsAb samples detected by the conventional method, before the concentration increases to 10000 mIU/ml, the signal value increases with the increase of the concentration; when the concentration continues to increase, the signal value decreases with the increase of the concentration of HBsAb. That is to say, samples with concentrations larger than 10000 mIU/ml are HD-Hook-effect samples. Sample 9 with a concentration of 10000 mIU/ml is the peak-value calibrator, and R0 is 37.5%.

In the conventional detection, a concentration range detected is 0-1000 mIU/ml, and if the concentration exceeds the upper limit of detection, it is shown that the concentration of the sample is larger than 1000 mIU/ml. When the concentration of the HD-Hook-effect sample continues to increase and the signal value continues to decrease, a sample with a super high concentration would be detected as a sample with a low concentration, examples of which are samples 12, 13, and 14. Therefore, in a conventional detection, it cannot be tell whether a result of the detected sample is a real concentration or a detected inaccurate low concentration caused by an effect of HD-Hook effect on the sample's super high concentration.

Figure 29:
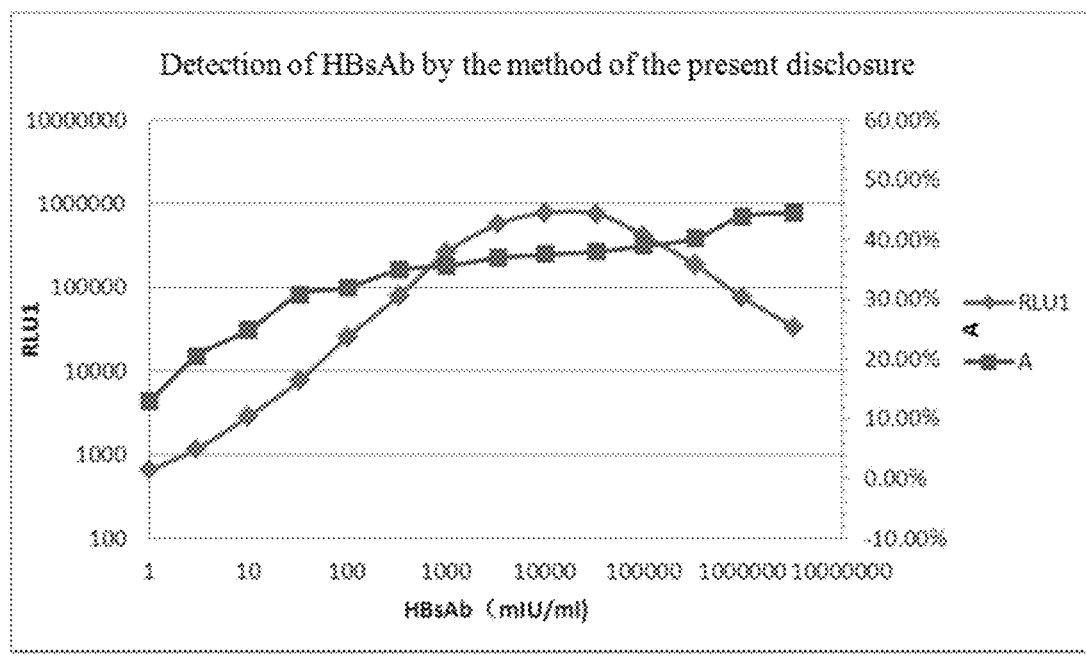
FIG. 29 is a curve showing a relationship between a first-time-read-value and a sample concentration and a relationship between a growth rate A and the sample concentration in detection of HBsAb by a method of the present disclosure.

The method of the present disclosure determines an HD-Hook-effect sample by means of two times of value reading. Each sample is detected for two times to obtain two signal values RLU1 and RLU2. A growth rate A from the first-time-read-value to the second-time-read-value calculated based on the equation $A=(RLU2/RLU1-1)\times100\%$ is used as an index for determining the concentration of the sample. As can be seen from Table 20 and FIG. 29, the signal value increases with the increase of the concentration before the concentration increases to 10000 mIU/ml, and after that, the signal value decreases with the increase of the concentration but the growth rate A continues to increase with the increase of the concentration. The concentration of the sample and the concentration of the calibrator can therefore be compared with each other by directly comparing the growth rate A with respect to the sample and the growth rate A with respect to the calibrator. Growth rates A with respect to samples 10 to 14 are all larger than the growth rate R0 with respect the peak-value calibrator (37.5%). This shows that concentrations of HBsAb in samples 10 to 14 are all larger than 10000 mIU/ml and therefore samples 10 to 14 are HD-Hook-effect samples. This is consistent with the real concentrations. The signal values with respect to samples 12, 13, and 14 are smaller than that of the calibrator 6, and concentrations of samples 12, 13, and 14 detected by the conventional method are 802.57 mIU/ml, 352.22 mIU/ml, and 147.9 mIU/ml, respectively. It is determined by the method of the present disclosure that samples 12, 13, and 14 are HD-Hook-effect samples and need to be diluted before detection.

The above examples serve as illustrations of the principles and effects of the present disclosure, and are not intended to restricting the present disclosure. Any one skilled in the art can make revisions or variations to the above examples without departing from the spirit and scope of the present disclosure. All equivalent revisions or variations made by those skilled in the art without departing from the spirit and scope of the present disclosure fall within the protection scope of the claims of the present application.

The invention claimed is:

1. A chemiluminescence immunoassay method, comprising:
   (a1) mixing a sample containing a target antigen to be detected with light-emitting particles coated with a primary antibody directed to the target antigen and a labeled secondary antibody directed to the target antigen to form a first sample mixture, and incubating the first sample mixture to form double-antibody sandwich complexes in the first sample mixture;
   (a2) adding light-sensitive particles labeled with a binding conjugate specific to the label of the secondary antibody into the first sample mixture obtained in step (a1) to form a second sample mixture; incubating the second sample mixture for a first period of time sufficient to allow the binding conjugate attached to the light-sensitive particles to bind the label of the secondary antibody in the complexes formed in the first sample mixture; detecting the amount of high energy level light emitted by the complexes that bound to the binding conjugate attached to the light sensitive particles in the second sample mixture; and reading a first signal value with a photon counter and marking the value as Relative Light Unit (RLU)1 to thus, perform a first-time-value-reading;
   (a3) incubating the second sample mixture for a second period of time after the first-time-value-reading in step (a2) then irradiating the second sample mixture and detecting the amount of high energy level light emitted by the complexes that bound to the binding conjugate attached to the light sensitive particles in the second sample mixture; and reading a second signal value with a photon counter and marking the value as RLU2 to thus perform a second-time-value-reading, wherein the second period of time is 7-minute longer than the first period of time;
   (a4) calculating a growth rate A from the signal value obtained at the first-time-value-reading to the signal value obtained at the second-time-value-reading with respect to the sample based on equation A=(RLU2/RLU1−1)×100%;
   (a5) plotting a standard curve based on a growth rate A' from the first-time-read-values to the second-time-read-values with respect to a series of standard substances containing known concentrations of the target antigen, wherein the concentrations of the target antigen in the series of standard substances are lower than the concentration at which HD-Hook effect occurs; and
   (a6) diluting the sample before detection if the growth rate A from the first-time-read-value to the second-time-read-value with respect to the sample containing the target antigen to be detected is larger than a maximum value of the standard curve; wherein the concentrations of the target antigen in the series of standard substances are lower than a concentration at which High Dose Hook (HD-Hook) effect occurs, and the series of standard substances are used in a positive control.

2. A chemiluminescence immunoassay method, comprising:
   (a1) mixing a sample containing a target antigen to be detected with light-emitting particles coated with a primary antibody directed to the target antigen and a labeled secondary antibody directed to the target antigen to form a first sample mixture, and incubating the first sample mixture to form double-antibody sandwich complexes in the first sample mixture;
   (a2) adding light-sensitive particles labeled with a binding conjugate specific to the label of the secondary antibody into the first sample mixture obtained in step (a1) to form a second sample mixture; incubating the second sample mixture for a first period of time sufficient to allow the binding conjugate attached to the light-sensitive particles to bind the label of the secondary antibody in the complexes formed in the first sample mixture; detecting the amount of high energy level light emitted by the complexes that bound to the binding conjugate attached to the light sensitive particles in the second sample mixture; and reading a first signal value with a photon counter and marking the value as RLU1 to thus, perform a first-time-value-reading;
   (a3) incubating the second sample mixture for a second period of time after the first-time-value-reading in step (a2); then irradiating the second sample mixture and detecting the amount of high energy level light emitted by the complexes that bound to the binding conjugate attached to the light sensitive particles in the second sample mixture; and reading a second signal value with a photon counter and marking the value as RLU2 to thus perform a second-time-value-reading, wherein the second period of time is 7-minute longer than the first period of time;
   (a4) calculating a growth rate A from the signal value obtained at the first-time-value-reading to the signal value obtained at the second-time-value-reading with respect to the sample based on equation A=(RLU2/RLU1−1)×100%; and
   (a5) comparing the growth rate A from the first-time-read-value to the second-time-read-value with respect to the sample containing the target antigen to be detected with a growth rate A", wherein if the growth rate A is larger than the growth rate A", it is determined that the concentration of the target antigen in sample is larger than the concentration of the target antigen in a standard substance; wherein the growth rate A" is obtained from the first-time-read-value to the second-time-read-value with respect to the standard substance containing known concentration of the target antigen;

the standard substance is used as a positive control.

3. A chemiluminescence immunoassay method, comprising:
(a1) mixing a sample containing a target antigen to be detected with light-emitting particles coated with a primary antibody directed to the target antigen and a labeled secondary antibody directed to the target antigen to form a first sample mixture, and incubating the first sample mixture to form double-antibody sandwich complexes in the first sample mixture;
(a2) adding light-sensitive particles labeled with a binding conjugate specific to the label of the secondary antibody into the first sample mixture obtained in step (d1) to form a second sample mixture; incubating the second sample mixture for a first period of time sufficient to allow the binding conjugate attached to the light-sensitive particles to bind the label of the secondary antibody in the complexes formed in the first sample mixture; detecting the amount of high energy level light emitted by the complexes that bound to the binding conjugate attached to the light sensitive particles in the second sample mixture; and reading a first signal value with a photon counter and marking the value as RLU1 to thus, perform a first-time-value-reading;
(a3) incubating the second sample mixture for a second period of time after the first-time-value-reading in step (a2) then irradiating the second sample mixture and detecting the amount of high energy level light emitted by the complexes that bound to the binding conjugate attached to the light sensitive particles in the second sample mixture; and reading a second signal value with a photon counter and marking the value as RLU2 to thus perform a second-time-value-reading, wherein the second period of time is 7-minute longer than the first period of time;
(a4) calculating a growth rate A from the signal value obtained at the first-time-value-reading to the signal value obtained at the second-time-value-reading with respect to the sample based on equation A=(RLU2/RLU1−1)×100%; and
(a5) comparing the growth rate A from the first-time-read-value to the second-time-read-value with respect to the sample to be detected containing the target antigen to be detected with a growth rate A", wherein if the growth rate A is larger than the growth rate A" and the first-time-read-value with respect to the sample to be detected is smaller than the first-time-read-value with respect to a standard substance, the sample is diluted before being detected; wherein the growth rate A" is obtained from the first-time-read-value to the second-time-read-value with respect to the standard substance containing known concentration of the target antigen;

the standard substance is used as a positive control.

4. A chemiluminescence immunoassay method, comprising:
(a1) mixing a sample containing a target antigen to be detected with light-emitting particles coated with a primary antibody directed to the target antigen and a labeled secondary antibody directed to the target antigen to form a first sample mixture, and incubating the first sample mixture to form double-antibody sandwich complexes in the first sample mixture;
(a2) adding light-sensitive particles labeled with a binding conjugate specific to the label of the secondary antibody into the first sample mixture obtained in step (a1) to form a second sample mixture; incubating the second sample mixture for a first period of time sufficient to allow the binding conjugate attached to the light-sensitive particles to bind the label of the secondary antibody in the complexes formed in the first sample mixture; detecting the amount of high energy level light emitted by the complexes that bound to the binding conjugate attached to the light sensitive particles in the second sample mixture; and reading a first signal value with a photon counter and marking the value as RLU1 to thus, perform a first-time-value-reading;
(a3) incubating the second sample mixture for a second period of time after the first-time-value-reading in step (a2) then irradiating the second sample mixture and detecting the amount of high energy level light emitted by the complexes that bound to the binding conjugate attached to the light sensitive particles in the second sample mixture; and reading a second signal value with a photon counter and marking the value as RLU2 to thus perform a second-time-value-reading, wherein the second period of time is 7-minute longer than the first period of time;
(a4) calculating a growth rate A from the signal value obtained at the first-time-value-reading to the signal value obtained at the second-time-value-reading with respect to the sample based on equation A=(RLU2/RLU1−1)×100%;
(a5) plotting a standard curve based on a growth rates A' from the first-time-read-values to the second-time-read-values with respect to a series of standard substances containing known concentrations of the target antigen; and
(a6) determining, based on the growth rate A, whether the concentration of the target antigen in sample to be detected is located in a rising section or in a dropping section of the standard curve, and then calculating the concentration of the target antigen in sample by putting the RLU1 of the sample to be detected in a corresponding calibration curve thereof,
wherein the calibration curve is a curve plotted based on the first-time-read-values with respect to the series of standard substances containing known concentration of the target antigen;

the concentrations of the target antigen in the series of standard substances are lower than a concentration at which High Dose Hook (HD-Hook) effect occurs, and the series of standard substances are used in a positive control.

5. A chemiluminescence immunoassay method, comprising:
(a1) mixing a sample containing a target antibody to be detected with light-emitting particles coated with a primary antigen directed to the target antibody and a labeled secondary antigen directed to the target antibody to form a first sample mixture, and incubating the first sample mixture to form double-antigen sandwich complexes in the first sample mixture;
(a2) adding light-sensitive particles labeled with a binding conjugate specific to the label of the secondary antigen into the first sample mixture obtained in step (a1) to form a second sample mixture; incubating the second sample mixture for a first period of time sufficient to allow the binding conjugate attached to the light-sensitive particles to bind the label of the secondary antigen in the complexes formed in the first sample mixture; detecting the amount of high energy level light emitted by the complexes that bound to the binding conjugate attached to the light sensitive particles in the second sample mixture; and reading a first signal value with a photon counter and marking the value as Relative Light Unit (RLU)1 to thus, perform a first-time-value-reading;

(a3) incubating the second sample mixture for a second period of time after the first-time-value-reading in step (a2) then irradiating the second sample mixture and detecting the amount of high energy level light emitted by the complexes that bound to the binding conjugate attached to the light sensitive particles in the second sample mixture; and reading a second signal value with a photon counter and marking the value as RLU2 to thus perform a second-time-value-reading, wherein the second period of time is 7-minute longer than the first period of time;

(a4) calculating a growth rate A from the signal value obtained at the first-time-value-reading to the signal value obtained at the second-time-value-reading with respect to the sample based on equation A=(RLU2/RLU1−1)×100%;

(a5) plotting a standard curve based on a growth rate A' from the first-time-read-values to the second-time-read-values with respect to a series of standard substances containing known concentrations of the target antibody, wherein the concentrations of the target antibody in the series of standard substances are lower than the concentration at which HD-Hook effect occurs; and (a6) diluting the sample before detection if the growth rate A from the first-time-read-value to the second-time-read-value with respect to the sample containing the target antibody to be detected is larger than a maximum value of the standard curve; wherein the concentrations of the target antibody in the series of standard substances are lower than a concentration at which High Dose Hook (HD-Hook) effect occurs, and the series of standard substances are used in a positive control.

* * * * *